(12) United States Patent
Zhang et al.

(10) Patent No.: US 11,529,394 B2
(45) Date of Patent: Dec. 20, 2022

(54) POLYPEPTIDE CONJUGATES AND METHODS OF USES

(71) Applicant: BEIJING QL BIOPHARMACEUTICAL CO., LTD., Beijing (CN)

(72) Inventors: Yuanyuan Zhang, Beijing (CN); Xinle Wu, Beijing (CN); Haixia Zou, Beijing (CN); Peng Zhai, Beijing (CN); Yaoguang Jin, Beijing (CN); Bo Wu, Beijing (CN); Xu Chen, Beijing (CN); Wei Guo, Beijing (CN); Xinyu Zhao, Beijing (CN); Zuobin Wang, Beijing (CN); Lingli Zeng, Beijing (CN)

(73) Assignee: BEIJING QL BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/562,014

(22) Filed: Dec. 27, 2021

(65) Prior Publication Data
US 2022/0133856 A1    May 5, 2022

Related U.S. Application Data

(63) Continuation-in-part of application No. PCT/CN2021/122075, filed on Sep. 30, 2021.

(30) Foreign Application Priority Data

Sep. 30, 2020  (WO) ............... PCT/CN2020/119335
Jun. 9, 2021   (WO) ............... PCT/CN2021/099030

(51) Int. Cl.
| A61K 38/26 | (2006.01) |
| A61K 47/65 | (2017.01) |
| A61P 3/04  | (2006.01) |
| A61P 3/06  | (2006.01) |
| A61P 3/10  | (2006.01) |

(52) U.S. Cl.
CPC .............. *A61K 38/26* (2013.01); *A61K 47/65* (2017.08); *A61P 3/04* (2018.01); *A61P 3/06* (2018.01); *A61P 3/10* (2018.01)

(58) Field of Classification Search
None
See application file for complete search history.

(56) References Cited

U.S. PATENT DOCUMENTS

| 5,208,020 | A  | 5/1993  | Chari et al.      |
| 6,191,102 | B1 | 2/2001  | DiMarchi et al.   |
| 6,268,343 | B1 | 7/2001  | Knudsen et al.    |
| 6,441,163 | B1 | 8/2002  | Chari et al.      |
| 6,458,924 | B2 | 10/2002 | Knudsen et al.    |
| 6,737,236 | B1 | 5/2004  | Pieken et al.     |
| 7,083,970 | B2 | 8/2006  | Schultz et al.    |
| 7,211,557 | B2 | 5/2007  | DiMarchi et al.   |
| 7,226,990 | B2 | 6/2007  | Knudsen et al.    |
| 7,235,627 | B2 | 6/2007  | Knudson et al.    |
| 7,271,149 | B2 * | 9/2007 | Glaesner ............... A61P 3/04 530/308 |
| 7,576,059 | B2 | 8/2009  | Jonassen et al.   |
| 7,893,017 | B2 | 2/2011  | Lau et al.        |
| 8,097,698 | B2 | 1/2012  | Knudsen et al.    |
| 8,129,343 | B2 | 3/2012  | Lau et al.        |
| 8,445,433 | B2 | 5/2013  | Werbitzky et al.  |
| 8,536,122 | B2 | 9/2013  | Lau et al.        |
| 8,563,521 | B2 | 10/2013 | Skerra et al.     |
| 8,603,972 | B2 | 12/2013 | Lau et al.        |
| 8,648,041 | B2 | 2/2014  | Garibay et al.    |
| 8,673,860 | B2 | 3/2014  | Schellenberger et al. |
| 8,895,694 | B2 | 11/2014 | Spetzler et al.   |
| 8,957,021 | B2 | 2/2015  | Schellenberger et al. |
| 9,006,178 | B2 | 4/2015  | Kofoed et al.     |
| 9,067,977 | B2 | 6/2015  | Spetzler et al.   |
| 9,498,534 | B2 | 11/2016 | Caggiano et al.   |
| 9,527,900 | B2 | 12/2016 | Linderoth et al.  |
| 9,550,819 | B2 | 1/2017  | Lindhout et al.   |
| 9,657,079 | B2 | 5/2017  | Spetzler et al.   |
| 9,708,383 | B2 | 7/2017  | Madsen et al.     |
| 9,732,137 | B2 | 8/2017  | Lau et al.        |
| 9,758,560 | B2 | 9/2017  | Lau et al.        |
| 10,000,542 | B2 | 6/2018 | Kofoed et al.     |
| 10,005,827 | B2 | 6/2018 | Spetzler et al.   |
| 10,010,614 | B2 | 7/2018 | Reedtz-Runge et al. |
| 10,308,700 | B2 | 6/2019 | Lau et al.        |
| 10,370,426 | B2 | 8/2019 | Oh et al.         |

(Continued)

FOREIGN PATENT DOCUMENTS

| CN | 1232470 A   | 10/1999 |
| CN | 100444898 C | 12/2008 |

(Continued)

OTHER PUBLICATIONS

Yu et al., Adv Drug Del Reviews 130 (2018) 113-130 (Year: 2018).*
Wang et al., "Expanding the Genetic Code of *Escherichia coli*", Science 292: 498-500, Apr. 20, 2001.
Wang and Schultz et al., "An Expanded Eukaryotic Genetic Code", Science 301: 964-967, Aug. 15, 2003.
Altschul et al., "Basic Local Alignment Search Tool", J. Mol. Biol., 215:403-410 (1990).

(Continued)

*Primary Examiner* — Fred H Reynolds
*Assistant Examiner* — Joseph Fischer
(74) *Attorney, Agent, or Firm* — Jun He Law Offices P.C.; James J. Zhu

(57) ABSTRACT

The present disclosure provides a polypeptide conjugates comprising GLP-1 receptor agonist and a peptide linker, and pharmaceutical compositions comprising the same. Methods of using such for treating diseases are also provided.

10 Claims, 18 Drawing Sheets

Specification includes a Sequence Listing.

(56) References Cited

U.S. PATENT DOCUMENTS

| | | | |
|---|---|---|---|
| 10,392,428 B2 | 8/2019 | Kofoed | |
| 10,398,782 B2 | 9/2019 | Gao et al. | |
| 10,400,020 B2 | 9/2019 | Oh et al. | |
| 10,604,554 B2 | 3/2020 | Kofoed et al. | |
| 10,689,429 B2 | 6/2020 | Linderoth et al. | |
| 10,946,074 B2 | 3/2021 | Kofoed et al. | |
| 11,130,794 B2 | 9/2021 | Tornoee et al. | |
| 2003/0027996 A1 | 2/2003 | Staby | |
| 2003/0119023 A1* | 6/2003 | Choo | C12N 15/8216 435/325 |
| 2003/0199672 A1 | 10/2003 | Knudsen et al. | |
| 2004/0265952 A1 | 12/2004 | Deiters et al. | |
| 2007/0042956 A1 | 2/2007 | Johansen et al. | |
| 2007/0093417 A1 | 4/2007 | Hansen et al. | |
| 2007/0203058 A1* | 8/2007 | Lau | A61P 1/04 514/9.9 |
| 2007/0203068 A1 | 8/2007 | Nielsen | |
| 2008/0081038 A1 | 4/2008 | Cho et al. | |
| 2008/0214439 A1 | 9/2008 | Grabstein et al. | |
| 2009/0005312 A1 | 1/2009 | Hansen et al. | |
| 2009/0092582 A1 | 4/2009 | Bogin et al. | |
| 2009/0156478 A1 | 6/2009 | Lau et al. | |
| 2010/0239554 A1 | 9/2010 | Schellenberger et al. | |
| 2010/0260706 A1 | 10/2010 | Bogin et al. | |
| 2010/0317057 A1 | 12/2010 | Lau et al. | |
| 2011/0166321 A1* | 7/2011 | Garibay | A61P 1/04 530/323 |
| 2011/0213131 A1 | 9/2011 | Christensen et al. | |
| 2011/0312881 A1 | 12/2011 | Silverman et al. | |
| 2012/0000418 A1 | 1/2012 | Huang | |
| 2013/0244931 A1 | 9/2013 | Lau et al. | |
| 2015/0017188 A1 | 1/2015 | Eigenbrot, Jr. et al. | |
| 2015/0152157 A1 | 6/2015 | Kofoed et al. | |
| 2015/0210745 A1 | 7/2015 | Kofoed et al. | |
| 2015/0266943 A1 | 9/2015 | Chhabra et al. | |
| 2015/0273069 A1 | 10/2015 | Bjerregaard et al. | |
| 2016/0143998 A1 | 5/2016 | Reedtz-Runge et al. | |
| 2016/0158321 A1 | 6/2016 | Cleland et al. | |
| 2016/0199454 A1 | 7/2016 | Liu et al. | |
| 2017/0037088 A1 | 2/2017 | Schellenberger et al. | |
| 2017/0058014 A1 | 3/2017 | Wieczorek et al. | |
| 2017/0145069 A1 | 5/2017 | Lau et al. | |
| 2017/0240614 A1 | 8/2017 | Baldwin et al. | |
| 2017/0320927 A1 | 11/2017 | Sauerberg et al. | |
| 2018/0051063 A1 | 2/2018 | Cleland et al. | |
| 2018/0125988 A1 | 5/2018 | Yang et al. | |
| 2018/0127512 A1 | 5/2018 | Doronina et al. | |
| 2018/0291076 A1* | 10/2018 | Kjeldsen | C07K 14/62 |
| 2019/0083577 A1 | 3/2019 | Schellenberger et al. | |
| 2019/0153115 A1 | 5/2019 | Schellenberger et al. | |
| 2020/0087379 A1 | 3/2020 | Schellenberger et al. | |
| 2020/0231645 A1 | 7/2020 | Tornoee et al. | |
| 2020/0392195 A1 | 12/2020 | Schellenberger et al. | |
| 2022/0009989 A1 | 1/2022 | Muenzel et al. | |

FOREIGN PATENT DOCUMENTS

| | | |
|---|---|---|
| CN | 101712722 A | 5/2010 |
| CN | 103619175 A | 3/2014 |
| WO | 1991011457 A1 | 8/1991 |
| WO | 1996029342 A1 | 9/1996 |
| WO | 1998008871 A1 | 3/1998 |
| WO | WO-9808871 A1 * | 3/1998 ........... A61K 31/426 |
| WO | 1999043341 A1 | 9/1999 |
| WO | 1999043705 A1 | 9/1999 |
| WO | 1999043706 A1 | 9/1999 |
| WO | 1999043707 A1 | 9/1999 |
| WO | 2007103515 A2 | 9/2007 |
| WO | 2011123813 A2 | 10/2011 |
| WO | 2016131893 A1 | 8/2016 |
| WO | 2020207477 A1 | 10/2020 |

OTHER PUBLICATIONS

Altschul et al., "Gapped BLAST and PSI-BLAST: a new generation of protein database search programs", Nucleic Acids Research, 1997, vol. 25, No. 17, 3389-3402.

Higgins et al., "Using Clustal for Multiple Sequence Alignments", Methods in Enzymology, 266:383-402 (1996).

Larkin et al., "Clustal W and Clustal X version 2.0", Bioinformatics (Oxford, England), 23(21): 2947-8 (2007).

Lau et al., "The discovery of the once weekly glucagon like peptide 1 (GLP-1) analog semaglutide", J. Med. Chem. 2015, 58, 7370-7380.

Dennis et al., "Albumin Binding as a General Strategy for Improving the Pharmacokinetics of Proteins", J. Biol Chem. 277, 38 (2002) 35035-35043.

Batzer et al., "Enhanced evolutionary PCR using oligonucleotides with inosine at the 3'-terminus", Nucleic Acids Research (1991), vol. 19, No. 18, 5081.

Ohtsuka et al., "An Alternative Approach to Deoxyoligonucleotides as Hybridization Probes by Insertion of Deoxyinosine at Ambiguous Codon Positions*", J. Biol. Chem. 260: 2605-2608 (1985).

Rossolini et al., "Use of deoxyinosine-containing primers vs degenerate primers for polymerase chain reaction based on ambiguous sequence information", Mol. Cell. Probes 8:91-98 (1994).

Carter et al., "High Level Escherichia coli Expression and Production of a Bivalent Humanized Anitbody Fragment", Bio/Technology 10:163-167 (1992).

Carlsson et al., "Protein Thiolation and Reversible Protein-Protein Conjugation N-Succinimidyl 3-(2-Pyridyldithio)Propionate, a New Heterobifunctional Reagent", BIochem. J. (1978) 173, 723-737.

Kim,Y.et al.,"Novel AGLP-1 albumin fusion protein as a long-lasting agent for type 2 diabetes", BMB Reports, Dec. 31, 2013(Dec. 31, 2013) No. 12, vol. 46, 606-610.

Jiang,Y.N.et al.,"Application of new fusion sequence in long-term GLP-1 drugs development", Chinese Doctoral Dissertations & Master's Theses Full-text Database (Master) Medicine and Health Sciences, Feb. 15, 2018(Feb. 15, 2018) No. 02.

McBrayer,D.N et al., "Recent Advances in GLP-1 Receptor Agonists for Use in Diabetes Mellitus", Drug Dev Res., Sep. 30, 2017(Sep. 30, 2017) No. 6, vol. 78, abstract, pp. 292-299.

Deiters et al., "Adding Amino Acids with Novel Reactivity to the Genetic Code of Saccharomyces cerevisiae", J. Am. Chem. Soc. 2003, 125, 11782-11783.

Zhang et al., "A New Strategy for the Synthesis of Glycoproteins", Science 303:371-373, 2004.

The first office action of the corresponding Chinese application 202180006277.3, dated Aug. 26, 2022.

* cited by examiner

GLP-1

| SEQ ID NO | GLP-1 Sequence |
|---|---|
| 1 | HAEGTFTSDVSSYLEGQAAKEFIAWLVKGRG |
| 2 | $X_7X_8$EGTFTSDVSSYLE$X_{22}X_{23}$AA$X_{26}X_{27}$FI$X_{30}$WLV$X_{34}$G$X_{36}$G |
| 3 | HAib-EGTFTSDVSSYLEGQAAKEFIAWLVRGGG |
| 4 | HAib-EGTFTSDVSSYLEGQAACEFIAWLVRGGG |
| 5 | HAib-EGTFTSDVSSYLEGQAARKFIAWLVRGGG |
| 6 | HAib-EGTFTSDVSSYLEGQAAKCFIAWLVRGGG |
| 7 | HAib-EGTFTSDVSSYLEGQAAREFIAWLVRGGG |
| 8 | HAib-EGTFTSDVSSYLEEQAAKEFIAWLVRGGG |
| 9 | HAib-EGTFTSDVSSYLEEQAACEFIAWLVRGGG |
| 10 | HAib-EGTFTSDVSSYLEEQAARKFIAWLVRGGG |
| 11 | HAib-EGTFTSDVSSYLEEQAAKCFIAWLVRGGG |
| 12 | HAib-EGTFTSDVSSYLEEQAAREFIAWLVRGGG |
| 13 | HAib-EGTFTSDVSSYLEGQAAKEFIAWLVRGRG |
| 14 | HAib-EGTFTSDVSSYLEGQAACEFIAWLVRGRG |
| 15 | HAib-EGTFTSDVSSYLEGQAARKFIAWLVRGRG |
| 16 | HAib-EGTFTSDVSSYLEGQAAKCFIAWLVRGRG |
| 17 | HAib-EGTFTSDVSSYLEGQAAREFIAWLVRGRG |
| 18 | HAib-EGTFTSDVSSYLEEQAAKEFIAWLVRGRG |

Figure 4A

| 19 | HAib-EGTFTSDVSSYLEEQAACEFIAWLVRGRG |
| 20 | HAib-EGTFTSDVSSYLEEQAARKFIAWLVRGRG |
| 21 | HAib-EGTFTSDVSSYLEEQAAKCFIAWLVRGRG |
| 22 | HAib-EGTFTSDVSSYLEEQAAREFIAWLVRGRG |
| 23 | HGEGTFTSDVSSYLEGQAAKEFIAWLVRGGG |
| 24 | HGEGTFTSDVSSYLEGQAACEFIAWLVRGGG |
| 25 | HGEGTFTSDVSSYLEGQAARKFIAWLVRGGG |
| 26 | HGEGTFTSDVSSYLEGQAAKCFIAWLVRGGG |
| 27 | HGEGTFTSDVSSYLEGQAAREFIAWLVRGGG |
| 28 | HGEGTFTSDVSSYLEEQAAKEFIAWLVRGGG |
| 29 | HGEGTFTSDVSSYLEEQAACEFIAWLVRGGG |
| 30 | HGEGTFTSDVSSYLEEQAARKFIAWLVRGGG |
| 31 | HGEGTFTSDVSSYLEEQAAKCFIAWLVRGGG |
| 32 | HGEGTFTSDVSSYLEEQAAREFIAWLVRGGG |
| 33 | HGEGTFTSDVSSYLEGQAAKEFIAWLVRGRG |
| 34 | HGEGTFTSDVSSYLEGQAACEFIAWLVRGRG |
| 35 | HGEGTFTSDVSSYLEGQAAREFIAWLVRGRG |
| 36 | HGEGTFTSDVSSYLEEQAAKEFIAWLVRGRG |
| 37 | HGEGTFTSDVSSYLEEQAACEFIAWLVRGRG |
| 38 | HGEGTFTSDVSSYLEEQAARKFIAWLVRGRG |

Figure 4B

| | |
|---|---|
| 39 | HGEGTFTSDVSSYLEEQAAKCFIAWLVRGRG |
| 40 | HGEGTFTSDVSSYLEEQAAREFIAWLVRGRG |
| 41 | HGEGTFTSDVSSYLEEQAAKEFIAWLVKGGG |
| 42 | HGEGTFTSDVSSYLEGQAAKEFIAWLVKGGG |
| 43 | HGEGTFTSDVSSYLEEQAAKEFIAWLVKGRG |
| 44 | HGEGTFTSDVSSYLEGQAAKEFIAWLVKGRG |
| 184 | HAib-EGTFTSDVSSYLEEQAACEFIAWLVRGGG |

Linker Repeats

| SEQ ID NO | Linker Repeat Sequence |
|---|---|
| 45 | GQEPGAQP |
| 46 | GAQPGAQP |
| 47 | GQEP |
| 48 | GAQP |
| 49 | GAQPGQEPGAQP |
| 50 | GAQPGQEP |
| 51 | GEQP |
| 52 | GPQE |
| 53 | GPEQ |
| 54 | GSEP |

Figure 4C

| 55 | GESP |
| --- | --- |
| 56 | GPSE |
| 57 | GPES |
| 58 | GQAP |
| 59 | GPAQ |
| 60 | GPQA |
| 61 | GSQP |
| 62 | GASP |
| 63 | GPAS |
| 64 | GPSA |
| 65 | GGGS |
| 66 | GSGS |
| 67 | GGGGS |
| 68 | GQEPGQAP |
| 69 | GQAPGQEP |
| 70 | SEPATSGSETPGTSESATPESGPGTSTEPSEG |
| 71 | SEPATS |
| 72 | GSETPG |
| 73 | TSESAT |
| 74 | PESGPG |

Figure 4D

| | 75 | TSTEPS |
|---|---|---|

Linkers

| SEQ ID NO | Linker Sequence |
|---|---|
| 76 | GAQPGAQPGAQPGAQPGAQPGAQPGAQPGAQPGAQPGQAP |
| 77 | GAQPGAQPGAQPGAQPGAQPGAQPGAQPGAQPGAQPGAQPGAQPGAQPGAQPGAQPGAQPGAQPGAQPGQAP |
| 78 | GAQPGAQPGAQPGAQPGAQPGAQPGAQPGAQPGAQPGAQPGAQPGAQPGAQPGQAP |
| 79 | GAQPGAQPGAQPGAQPGAQPGAQPGAQPGAQPGAQPGAQPGAQPGQAP |
| 80 | GAQPGAQPGAQPGAQPGAQPGAQPGAQPGQAP |
| 81 | GAQPGAQPGAQPGAQPGAQPGQAP |
| 82 | GAQPGAQPGQAP |
| 83 | GAQPGAQPGAQPGAQPGAQPGAQPGAQPGAQPGAQPGAQP |
| 84 | GAQPGAQPGAQPGAQPGAQPGAQPGAQPGAQPGAQPGAQPGAQPGAQPGAQPGAQPGAQPGAQPGAQPGAQP |
| 85 | GAQPGAQPGAQPGAQPGAQPGAQPGAQPGAQPGAQPGAQPGAQPGAQPGAQPGAQP |
| 86 | GAQPGAQPGAQPGAQPGAQPGAQPGAQPGAQPGAQPGAQPGAQPGAQP |
| 87 | GAQPGAQPGAQPGAQPGAQPGAQPGAQPGAQP |
| 88 | GAQPGAQPGAQPGAQPGAQPGAQP |
| 89 | GAQPGAQPGAQP |

Figure 4E

| SEQ ID NO | Linker Sequence |
|---|---|
| 90 | GAQPGAQPGAQPGAQPGAQPGAQPGAQPGAQPGAQPGQKP |
| 91 | GAQPGAQPGAQPGAQPGAQPGAQPGAQPGAQPGAQPGAQPGAQPGAQPGAQPGAQPGAQPGAQPGAQPGQKP |
| 92 | GAQPGAQPGAQPGAQPGAQPGAQPGAQPGAQPGAQPGAQPGAQPGAQPGAQPGAQPGAQPGQKP |
| 93 | GAQPGAQPGAQPGAQPGAQPGAQPGAQPGAQPGAQPGAQPGAQPGQKP |
| 94 | GAQPGAQPGAQPGAQPGAQPGAQPGAQPGAQPGQKP |
| 95 | GAQPGAQPGAQPGAQPGAQPGQKP |
| 96 | GAQPGAQPGQKP |
| 97 | GAQPGAQPGAQPGAQPGAQPGAQPGAQPGAQPGAQPGAKP |
| 98 | GAQPGAQPGAQPGAQPGAQPGAQPGAQPGAQPGAQPGAQPGAQPGAQPGAQPGAQPGAQPGAQPGAKP |
| 99 | GAQPGAQPGAQPGAQPGAQPGAQPGAQPGAQPGAQPGAQPGAQPGAQPGAQPGAQPGAKP |
| 100 | GAQPGAQPGAQPGAQPGAQPGAQPGAQPGAQPGAQPGAQPGAQPGAKP |
| 101 | GAQPGAQPGAQPGAQPGAQPGAQPGAQPGAQPGAKP |
| 102 | GAQPGAQPGAQPGAQPGAQPGAKP |
| 103 | GAQPGAQPGAKP |
| 104 | GAQPGAQPGAQPGAQPGAQPGAQPGAQPGAQPGAQPGQCP |
| 105 | GAQPGAQPGAQPGAQPGAQPGAQPGAQPGAQPGAQPGAQPGAQPGAQPGAQPGAQPGAQPGAQPGQCP |
| 106 | GAQPGAQPGAQPGAQPGAQPGAQPGAQPGAQPGAQPGAQPGAQPGAQPGAQPGAQPGQCP |
| 107 | GAQPGAQPGAQPGAQPGAQPGAQPGAQPGAQPGAQPGAQPGAQPGQCP |
| 108 | GAQPGAQPGAQPGAQPGAQPGAQPGAQPGQCP |

Figure 4F

| 109 | GAQPGAQPGAQPGAQPGAQPGQCP |
|---|---|
| 110 | GAQPGAQPGQCP |
| 111 | GAQPGAQPGAQPGAQPGAQPGAQPGAQPGAQPGAQPGACP |
| 112 | GAQPGAQPGAQPGAQPGAQPGAQPGAQPGAQPGAQPGAQPGAQPGAQPGAQPGAQPGAQPGAQPGAQPGACP |
| 113 | GAQPGAQPGAQPGAQPGAQPGAQPGAQPGAQPGAQPGAQPGAQPGAQPGAQPGAQPGACP |
| 114 | GAQPGAQPGAQPGAQPGAQPGAQPGAQPGAQPGAQPGAQPGACP |
| 115 | GAQPGAQPGAQPGAQPGAQPGAQPGAQPGACP |
| 116 | GAQPGAQPGAQPGAQPGAQPGACP |
| 117 | GAQPGAQPGACP |
| 175 | GAQPGAQPGAQPGAQPGAQPGAQPGAQPGAQPGAQPGAQK |
| 176 | GAQPGAQPGAQPGAQPGAQPGAQPGAQPGAQPGAQK |

Fusion Polypeptide

| SEQ ID NO | Fusion Polypeptide Sequence |
|---|---|
| 118 | HAib-EGTFTSDVSSYLEGQAAKEFIAWLVRGGGGAQPGAQPGAQPGAQPGAQPGAQPGAQPGAQPGAQPGQKP |
| 119 | HAib-EGTFTSDVSSYLEGQAAREFIAWLVRGGGGAQPGAQPGAQPGAQPGAQPGAQPGAQPGAQPGAQPGQKP |
| 120 | HAib-EGTFTSDVSSYLEGQAAKEFIAWLVRGGGGAQPGAQPGAQPGAQPGAQPGAQPGAQPGAQPGAQPGAQPGAQPGAQPGAQPGAQPGAQPGQKP |

Figure 4G

| 121 | HAib-EGTFTSDVSSYLEGQAAKEFIAWLVRGGGGAQPGAQPGAQPGAQPGAQPGAQPGAQPGAQPGAQPGAQPGAQPGAQPGAQPGQKP |
|---|---|
| 122 | HAib-EGTFTSDVSSYLEGQAAKEFIAWLVRGGGGAQPGAQPGAQPGAQPGAQPGAQPGAQPGAQPGAQPGAQPGAQPGQKP |
| 123 | HAib-EGTFTSDVSSYLEGQAAKEFIAWLVRGGGGAQPGAQPGAQPGAQPGAQPGAQPGAQPGQKP |
| 124 | HAib-EGTFTSDVSSYLEGQAAKEFIAWLVRGGGGAQPGAQPGAQPGAQPGAQPGQKP |
| 125 | HAib-EGTFTSDVSSYLEGQAAKEFIAWLVRGGGGAQPGAQPGQKP |
| 126 | HAib-EGTFTSDVSSYLEGQAAREFIAWLVRGGGGAQPGAQPGAQPGAQPGAQPGAQPGAQPGQKP |
| 127 | HAib-EGTFTSDVSSYLEGQAAREFIAWLVRGGGGAQPGAQPGAQPGAQPGAQPGAQPGQKP |
| 128 | HAib-EGTFTSDVSSYLEGQAAREFIAWLVRGGGGAQPGAQPGQKP |
| 129 | HAib-EGTFTSDVSSYLEEQAAKEFIAWLVRGGGGAQPGAQPGAQPGAQPGAQPGAQPGAQPGAQPGQKP |
| 130 | HAib-EGTFTSDVSSYLEEQAAKEFIAWLVRGGGGAQPGAQPGAQPGAQPGAQPGAQPGAQPGAQPGAQPGAQPGAQPGAQPGAQPGAQPGAQPGQKP |
| 131 | HAib-EGTFTSDVSSYLEEQAAKEFIAWLVRGGGGAQPGAQPGAQPGAQPGAQPGAQPGAQPGAQPGAQPGAQPGAQPGAQPGQKP |
| 132 | HAib-EGTFTSDVSSYLEEQAAKEFIAWLVRGGGGAQPGAQPGAQPGAQPGAQPGAQPGAQPGAQPGAQPGAQPGAQPGQKP |

Figure 4H

| | |
|---|---|
| 133 | HAib-EGTFTSDVSSYLEEQAAKEFIAWLVRGGGGAQPGAQPGAQPGAQPGAQPGAQPGAQPGQKP |
| 134 | HAib-EGTFTSDVSSYLEEQAAKEFIAWLVRGGGGAQPGAQPGAQPGAQPGAQPGQKP |
| 135 | HAib-EGTFTSDVSSYLEEQAAKEFIAWLVRGGGGAQPGAQPGQKP |
| 136 | HAib-EGTFTSDVSSYLEEQAAREFIAWLVRGGGGAQPGAQPGAQPGAQPGAQPGAQPGAQPGQKP |
| 137 | HAib-EGTFTSDVSSYLEEQAAREFIAWLVRGGGGAQPGAQPGAQPGAQPGAQPGAQPGQKP |
| 138 | HAib-EGTFTSDVSSYLEEQAAREFIAWLVRGGGGAQPGAQPGAQPGAQPGAQPGQKP |
| 139 | HAib-EGTFTSDVSSYLEEQAAREFIAWLVRGGGGAQPGAQPGQKP |
| 140 | HGEGTFTSDVSSYLEEQAAKEFIAWLVRGGGGAQPGAQPGAQPGAQPGAQPGAQPGAQPGAQPGQKP |
| 141 | HGEGTFTSDVSSYLEEQAAKEFIAWLVRGGGGAQPGAQPGAQPGAQPGAQPGAQPGAQPGAQPGAQPGAQPGAQPGAQPGQKP |
| 142 | HGEGTFTSDVSSYLEEQAAKEFIAWLVRGGGGAQPGAQPGAQPGAQPGAQPGAQPGAQPGAQPGAQPGAQPGQKP |
| 143 | HGEGTFTSDVSSYLEEQAAKEFIAWLVRGGGGAQPGAQPGAQPGAQPGAQPGAQPGAQPGQKP |
| 144 | HGEGTFTSDVSSYLEEQAAKEFIAWLVRGGGGAQPGAQPGAQPGAQPGAQPGAQPGQKP |
| 145 | HGEGTFTSDVSSYLEEQAAKEFIAWLVRGGGGAQPGAQPGAQPGAQPGQKP |

Figure 4I

| 146 | HGEGTFTSDVSSYLEEQAAKEFIAWLVRGGGGAQPGAQPGQKP |
| --- | --- |
| 147 | HGEGTFTSDVSSYLEEQAAREFIAWLVRGGGGAQPGAQPGAQPGAQPGAQPGAQPGAQPGAQPGAQPGQKP |
| 148 | HGEGTFTSDVSSYLEEQAAREFIAWLVRGGGGAQPGAQPGAQPGAQPGAQPGAQPGAQPGQKP |
| 149 | HGEGTFTSDVSSYLEEQAAREFIAWLVRGGGGAQPGAQPGAQPGAQPGAQPGQKP |
| 150 | HGEGTFTSDVSSYLEEQAAREFIAWLVRGGGGAQPGAQPGQKP |
| 151 | HAib-EGTFTSDVSSYLEGQAACEFIAWLVRGGGGAQPGAQPGAQPGAQPGAQPGAQPGAQPGAQPGAQPGAQPGAQPGAQPGAQPGAQPGAQPGQCP |
| 152 | HAib-EGTFTSDVSSYLEGQAACEFIAWLVRGGGGAQPGAQPGAQPGAQPGAQPGAQPGAQPGAQPGAQPGAQPGAQPGQCP |
| 153 | HAib-EGTFTSDVSSYLEGQAACEFIAWLVRGGGGAQPGAQPGAQPGAQPGAQPGAQPGAQPGAQPGAQPGQCP |
| 154 | HAib-EGTFTSDVSSYLEGQAACEFIAWLVRGGGGAQPGAQPGAQPGAQPGAQPGAQPGAQPGQCP |
| 155 | HAib-EGTFTSDVSSYLEGQAACEFIAWLVRGGGGAQPGAQPGAQPGAQPGAQPGAQPGQCP |
| 156 | HAib-EGTFTSDVSSYLEGQAACEFIAWLVRGGGGAQPGAQPGAQPGAQPGAQPGQCP |
| 157 | HAib-EGTFTSDVSSYLEGQAACEFIAWLVRGGGGAQPGAQPGQCP |
| 158 | HAib-EGTFTSDVSSYLEGQAAREFIAWLVRGGGGAQPGAQPGAQPGAQPGAQPGAQPGAQPGQCP |

Figure 4J

| | |
|---|---|
| 159 | HAib-EGTFTSDVSSYLEGQAAREFIAWLVRGGGGAQPGAQPGAQPGAQPGAQPGAQPGQCP |
| 160 | HAib-EGTFTSDVSSYLEGQAAREFIAWLVRGGGGAQPGAQPGAQPGAQPGAQPGQCP |
| 161 | HAib-EGTFTSDVSSYLEGQAAREFIAWLVRGGGGAQPGAQPGQCP |
| 162 | HGEGTFTSDVSSYLEEQAACEFIAWLVRGGGGAQPGAQPGAQPGAQPGAQPGAQPGAQPGAQPGAQPGQCP |
| 163 | HGEGTFTSDVSSYLEEQAACEFIAWLVRGGGGAQPGAQPGAQPGAQPGAQPGAQPGAQPGAQPGAQPGAQPGAQPGAQPGAQPGAQPGQCP |
| 164 | HGEGTFTSDVSSYLEEQAACEFIAWLVRGGGGAQPGAQPGAQPGAQPGAQPGAQPGAQPGAQPGAQPGAQPGAQPGAQPGQCP |
| 165 | HGEGTFTSDVSSYLEEQAACEFIAWLVRGGGGAQPGAQPGAQPGAQPGAQPGAQPGAQPGAQPGQCP |
| 166 | HGEGTFTSDVSSYLEEQAACEFIAWLVRGGGGAQPGAQPGAQPGAQPGAQPGAQPGQCP |
| 167 | HGEGTFTSDVSSYLEEQAACFIAWLVRGGGGAQPGAQPGAQPGAQPGAQPGQCP |
| 168 | HGEGTFTSDVSSYLEEQAACEFIAWLVRGGGGAQPGAQPGQCP |
| 169 | HGEGTFTSDVSSYLEEQAAREFIAWLVRGGGGAQPGAQPGAQPGAQPGAQPGAQPGAQPGAQPGQCP |
| 170 | HGEGTFTSDVSSYLEEQAAREFIAWLVRGGGGAQPGAQPGAQPGAQPGAQPGAQPGQCP |
| 171 | HGEGTFTSDVSSYLEEQAAREFIAWLVRGGGGAQPGAQPGAQPGAQPGAQPGQCP |

Figure 4K

| | |
|---|---|
| 172 | HGEGTFTSDVSSYLEEQAAREFIAWLVRGGGGAQPGAQPGQCP |
| 173 | HAib-EGTFTSDVSSYLEEQAAKEFIAWLVRGGGGAQPGAQPGAQPGAQPGAQPGAQPGAQPGAQPGAQK |
| 174 | HAib-EGTFTSDVSSYLEEQAAKEFIAWLVRGGGGAQPGAQPGAQPGAQPGAQPGAQPGAQK |
| 177 | HAib-EGTFTSDVSSYLEEQAACEFIAWLVRGGGGAQPGAQPGAQPGAQPGAQPGAQPGAQPGAQPGAQPGAQPGAQPGAQPGAQPGQCP |
| 178 | HAib-EGTFTSDVSSYLEEQAACEFIAWLVRGGGGAQPGAQPGAQPGAQPGAQPGAQPGAQPGAQPGAQPGAQPGAQPGQCP |
| 179 | HAib-EGTFTSDVSSYLEEQAACEFIAWLVRGGGGAQPGAQPGAQPGAQPGAQPGAQPGAQPGAQPGAQPGAQPGQCP |
| 180 | HAib-EGTFTSDVSSYLEEQAACEFIAWLVRGGGGAQPGAQPGAQPGAQPGAQPGAQPGAQPGAQPGQCP |
| 181 | HAib-EGTFTSDVSSYLEEQAACEFIAWLVRGGGGAQPGAQPGAQPGAQPGAQPGAQPGQCP |
| 182 | HAib-EGTFTSDVSSYLEEQAACEFIAWLVRGGGGAQPGAQPGAQPGAQPGAQPGQCP |
| 183 | HAib-EGTFTSDVSSYLEEQAACEFIAWLVRGGGGAQPGAQPGQCP |
| 185 | HAib-EGTFTSDVSSYLEGQAAKEFIAWLVRGGGGAQPGAQPGAQPGAQPGAQPGAQPGAQPGAQPGQCP |
| 186 | HAib-EGTFTSDVSSYLEGQAAKEFIAWLVRGGGGAQPGAQPGAQPGAQPGAQPGAQPGAQPGQCP |

Figure 4L

| | |
|---|---|
| 187 | HAib-EGTFTSDVSSYLEGQAAKEFIAWLVRGGGGAQPGAQPGAQPGAQPGAQPGQCP |
| 188 | HAib-EGTFTSDVSSYLEEQAAKEFIAWLVRGGGGAQPGAQPGAQPGAQPGAQPGAQPGAQPGAQPGQCP |
| 189 | HAib-EGTFTSDVSSYLEEQAAKEFIAWLVRGGGGAQPGAQPGAQPGAQPGAQPGAQPGQCP |
| 190 | HAib-EGTFTSDVSSYLEEQAAKEFIAWLVRGGGGAQPGAQPGAQPGAQPGAQPGQCP |

POLYPEPTIDE CONJUGATES AND METHODS OF USES

FIELD OF THE INVENTION

The present invention relates to polypeptide conjugates, pharmaceutical compositions thereof, and methods of using such to prevent and/or treat diseases.

BACKGROUND

Major biologically active fragment of Glucagon-Like Peptide-1 (GLP-1) is a 30 or 31 amino acid peptide fragment (amino acid 7-36 or 7-37 of GLP-1) deriving from the posttranslational processing of the proglucagon peptide. The initial GLP-1 product GLP-1 stimulates insulin synthesis and secretion and has been shown to prevent hyperglycemia in diabetics, especially type 2 diabetes. However, endogenous GLP-1 only has a half-life of approximately 2 minutes, which results in fasting plasma levels of GLP-1 of only 0-15 pmol/L.

Metabolic disorders are commonly associated with insulin resistance, visceral adiposity, atherogenic dyslipidemia, etc., which pose major and escalating public health and clinical challenge worldwide. However, existing treatment for metabolic diseases faces problems such as short half-life and/or low efficacy.

Furthermore, existing GLP-1 compounds are mainly administered by injection, and patients can have fear of injecting themselves if the dosing frequency is too often.

Therefore, there is a need for an improved therapeutic solution for treating metabolic diseases, and also to reduce the dosing frequency.

SUMMARY OF THE INVENTION

Provided herein are polypeptide conjugates, and pharmaceutical compositions comprising the same and methods of use for treating/preventing metabolic disorders.

In a first aspect, the present disclosure provides a polypeptide conjugate comprising: a single biologically active peptide attached to N-terminus of a peptide linker, and a first clearance-reducing moiety (CRM) conjugated to a first CRM residue in the peptide linker, wherein the biologically active peptide comprises a GLP-1 receptor agonist, and the first CRM residue is at least 5 amino acid residues (exclusive of the CRM residue) away from the C-terminal amino acid residue of the GLP-1 receptor agonist.

In some embodiments, the first CRM residue is at least 10, 15, 20, 21, 22, 23, 24, 25, 26, 27, 28, 29, 30, 31, 32, 35, 38, 40, 45, 46, 50, 55, 58, 60, 65, 70, 75, 78 amino acid residues (exclusive of the CRM residue) away from the C-terminal amino acid of the biologically active peptide.

In certain embodiments, the GLP-1 receptor agonist in the polypeptide conjugate has a length of no more than 70, 60, or 50 amino acid residues. In certain embodiments, the GLP-1 receptor agonist in the polypeptide conjugate has a length of no more than 49, 48, 47, 46, 45, 44, 43, 42, 41, 40, 39, 38, 37, 36, 35, 34, 33, 32, 31, or 30 amino acid residues.

In some embodiments, the GLP-1 receptor agonist comprises GLP-1.

In some embodiments, the biologically active peptide has no conjugated CRM.

In certain embodiments, the polypeptide conjugate provided herein is mono-conjugated, and has the CRM conjugated to the peptide linker but not to the biologically active peptide (e.g. GLP-1). In some of these embodiments, such mono-conjugated polypeptide conjugates provided herein has increased GLP-1 receptor agonist activity in the presence of human serum albumin (HSA), compared with a comparative polypeptide conjugate without the peptide linker and having a CRM conjugated on the GLP-1. In certain embodiments, the mono-conjugated polypeptide conjugates provided herein activates GLP-1 receptor in the presence of HSA at an EC50 no more than 50% (or no more than 40%, 30%, 20%, 10%, 5%, or 3%) of that of semaglutide in the presence of HSA, as determined in the same or comparable assay. In certain embodiments, the mono-conjugated polypeptide conjugates provided herein activates GLP-1 receptor in the absence of HSA at an EC50 comparable to (e.g. from about 20% to about 300% of) that of semaglutide in the absence of HSA, as determined in the same or comparable assay.

In certain embodiments, HSA is present in the in vitro assay for GLP-1 receptor activation at a suitable amount that allows assessment of impact of HSA binding to the GLP-1 receptor activation.

In certain embodiments, the mono-conjugated polypeptide conjugates provided herein binds to HSA at a binding affinity (KD) comparable to (e.g, from about 70% to about 500% of) that of semaglutide, as determined in the same or comparable assay.

In certain embodiments, the mono-conjugated polypeptide conjugates provided herein has at least comparable terminal half life compared to a comparative polypeptide conjugate without the peptide linker and having a CRM conjugated on the GLP-1, such as semaglutide, as determined under comparable in vivo study conditions and in the same type of experimental animals.

In some embodiments, the polypeptide conjugate is a double-conjugated polypeptide conjugate and further comprises a second CRM conjugated to a second CRM residue.

In some embodiments, the second CRM residue is in the biologically active peptide or in the peptide linker. In certain embodiments, the second CRM residue is at K26 of the GLP-1 peptide.

In some of these embodiments, the double-conjugated polypeptide conjugates provided herein has a comparable or acceptable GLP-1 receptor agonist activity in the presence of HSA, compared to a comparative polypeptide conjugate without the peptide linker and having a CRM conjugated on the GLP-1. In certain embodiments, the double-conjugated polypeptide conjugates provided herein activates GLP-1 receptor in the presence of HSA at an EC50 of no more than 2000% (or no more than 1500%, 1000%, 900%, 800%, 700%, 600%, or 500%) than that of a comparative polypeptide conjugate without the peptide linker and having a CRM conjugated on the GLP-1, such as semaglutide in the presence of HSA, as determined in the same or comparable assay. In certain embodiments, the double-conjugated polypeptide conjugates provided herein activates GLP-1 receptor in the absence of HSA at an EC50 comparable to (e.g. no more than 500% 400%, 300%, or 200% of, or even less than) that of a comparative polypeptide conjugate without the peptide linker and having a CRM conjugated on the GLP-1, such as semaglutide in the presence of HSA, as determined in the same or comparable assay. In certain embodiments, the double-conjugated polypeptide conjugates provided herein activates GLP-1 receptor at a first EC50 in the presence HSA, and at a second EC50 in the absence of HSA, and the first EC50 is higher of that the second EC50 but is no more than 1000-fold of that of the second EC50, for example, the first EC50 (in the presence of HSA) is no more than 900-fold, 800-fold, 700-fold, 600-fold, or 500-fold of the second EC50 (in the absence of HSA). In certain embodiments, HSA is present in the in vitro assay for GLP-1 receptor activation at a suitable amount that allows assessment of impact of HSA binding to the GLP-1 receptor activation.

In certain embodiments, the double-conjugated polypeptide conjugates provided herein binds to HSA at a higher binding affinity, represented by a KD value significantly lower than (e.g. no more than 50%, 40%, 30%, or 20% of) that of a comparative polypeptide conjugate without the peptide linker and having a CRM conjugated on the GLP-1, such as semaglutide, as determined in the same or comparable assay.

In certain embodiments, the double-conjugated polypeptide conjugates provided herein has an increase in terminal half-life by at least 50%, 60%, 70%, 80%, 90%, 100%, 120%, 150%, 180%, 200%, 300%, 400% than that of a comparative polypeptide conjugate without the peptide linker and having a CRM conjugated on the GLP-1, such as semaglutide, as determined under comparable in vivo study conditions and in the same type of experimental animals.

In certain embodiments, the double-conjugated polypeptide conjugates provided herein has blood or plasma or serum concentrations that remain within therapeutic window for the polypeptide conjugate for a period at least about 50% longer (60%, 70%, 80%, 90%, 100%, 120%, 150%, 180%, 200%, 300%, or 400% longer) that of a comparative polypeptide conjugate without the peptide linker and having a CRM conjugated on the GLP-1, such as semaglutide, as determined under comparable in vivo study conditions and in the same type of experimental animals.

In certain embodiments, the double-conjugated polypeptide conjugates provided herein provides for an extended duration of therapeutic efficacy in comparison with a comparative polypeptide conjugate without the peptide linker and having a CRM conjugated on the GLP-1, such as semaglutide, as determined under comparable in vivo study conditions and in the same type of experimental animals. In certain embodiments, the extended duration of therapeutic efficacy can be characterized by area under curve (AUC) for time-response curve and/or by the duration of the therapeutic response.

In certain embodiments, the therapeutic response comprises reduction in body weight, reduction in food intake, or reduction in glucose level (fasting glucose level or non-fasting glucose level). In certain embodiments, the double-conjugated polypeptide conjugates provided herein has an increase in the AUC for the time-response curve by at least 50%, 60%, 70%, 80%, 90%, 100%, 120% 150%, 180%, 200% than that of a comparative polypeptide conjugate without the peptide linker and having a CRM conjugated on the GLP-1, such as semaglutide, as determined under comparable in vivo study conditions and in the same type of experimental animals. In certain embodiments, the double-conjugated polypeptide conjugates provided herein has an increase in duration of the therapeutic response by at least 50%, 60%, 70%, 80%, 90%, 100%, 120%, 150%, 180%, 200%, 300%, or 400% than that of a comparative polypeptide conjugate without the peptide linker and having a CRM conjugated on the GLP-1, such as semaglutide, as determined under comparable in vivo study conditions and in the same type of experimental animals.

In some embodiments, the GLP-1 comprises an amino acid sequence having at least 70% sequence identity to SEQ ID NO: 1 while retaining substantial biological activity of SEQ ID NO: 1.

In some embodiments, the GLP-1 comprises no more than 9, 8, 7, 6, 5, or 4 mutations relative to SEQ ID NO: 1 while retaining substantial biological activity of SEQ ID NO: 1.

In some embodiments, the GLP-1 comprises or consists of one or more mutations at a position selected from the group consisting of: A8, G22, Q23, E27, K26, A30, K34, R36, and H7, or any combination thereof, relative to SEQ ID NO: 1.

In some embodiments, the GLP-1 comprises or consists of one or more substitutions selected from the group consisting of: A8Aib, G22E, K26R, K34R and R36G, or any combination thereof.

In some embodiments, the first CRM residue is lysine residue, and the polypeptide conjugate comprises only one lysine residue.

In some embodiments, the first and the second CRM residues are both lysine residues, and the polypeptide conjugate comprises only two lysine residues.

In some embodiments, the second lysine residue is in the GLP-1, and is optionally selected from the group consisting of K23, K26, K27, K30 and K34.

In some embodiments, all lysine residue(s) other than the CRM residue(s) in the GLP-1 are substituted to a non-lysine residue, optionally selected from the group consisting of Arginine (R), Glutamine (Q), Alanine (A), Glycine (G), Histidine (H), Serine (S), and Threonine (T).

In some embodiments, the first CRM residue is cysteine residue, and the polypeptide conjugate comprises only one cysteine residue.

In some embodiments, the first and the second CRM residues are both cysteine residues, and the polypeptide conjugate comprises only two cysteine residues.

In some embodiments, the second cysteine residue is in the GLP-1, and is optionally selected from the group consisting of C23, C26, C27, C30 and C34.

In some embodiments, the first CRM residue is a non natural amino acid residue, and the polypeptide conjugate comprises only one non-natural amino acid residue as the CRM residue.

In some embodiments, the first and the second amino acid residues are non-natural amino acid residues, and the polypeptide conjugate comprises only two non-natural amino acid residues as the CRM residues.

In some embodiments, the GLP-1 comprises an amino acid sequence of $X_7X_8$EGTFTSDVSSYLEX$_{22}$ $X_{23}$AAX$_{26}$X$_{27}$FI X$_{30}$WLVX$_{34}$GX$_{36}$G (SEQ ID NO: 2), wherein: the $X_7$ is H, imidazole-4-acetate (IA), or imidazolepropionic acid (IPA); the $X_8$ is A, G, S, V, Aib, T, I, or L; the $X_{22}$ is G, or E; the $X_{23}$ is Q, C or K, the $X_{26}$ is K, R, or C; the $X_{27}$ is E, K, or C; the $X_{30}$ is A, C or K the $X_{34}$ is R, K, or C, and the $X_{36}$ is R or G.

In some embodiments, the $X_7$ is H, $X_8$ is G or Aib, the $X_{22}$ is G or E; the $X_{23}$ is Q, C or K, the $X_{26}$ is K, R or C; the $X_{27}$ is E, K, or C; the $X_{30}$ is A, C or K, the $X_{34}$ is K, R or C, and the $X_{36}$ is R or G.

In some embodiments, the GLP-1 comprises an amino acid sequence selected from the group consisting of: SEQ ID NOs: 1, 3, 5, 7, 8, 10, 12, 13, 15, 17, 18, 20, 22, 23, 25, 27, 28, 30, 32, 33, 35, 36, 38 and 40-44.

In some embodiments, the GLP-1 comprises an amino acid sequence selected from the group consisting of: SEQ ID NOs:3-6, 8-11, 13-16, 18-21, 23-26, 28-31, 33, 34, 36-39 and 184.

In some embodiments, the polypeptide linker has a length of at least 10 amino acid residues (e.g. at least 12, 24, 32, 40, 48, 60, or 80 amino acid resides).

In some embodiments, the polypeptide linker has a length of 12-80 amino acid residues.

In some embodiments, the peptide linker consists of amino acid residues selected from the group consisting of G, Q, A, E, P, S and T, except for the CRM residue.

In some embodiments, the polypeptide linker comprises or consists of one or more repeats of a repeating sequence, except for the CRM residue.

In some embodiments, the repeating sequence consists of a sequence selected from the group consisting of: SEQ ID NO: 45 (GQEPGAQP), SEQ ID NO: 46 (GAQPGAQP), SEQ ID NO: 47 (GQEP), SEQ ID NO: 48 (GAQP), SEQ ID NO: 49 (GAQPGQEPGAQP), SEQ ID NO: 50 (GAQPGQEP), SEQ ID NO: 51 (GEQP), SEQ ID NO: 52 (GPQE), SEQ ID NO: 53 (GPEQ), SEQ ID NO: 54 (GSEP), SEQ ID NO: 55 (GESP), SEQ ID NO: 56 (GPSE), SEQ ID NO: 57 (GPES), SEQ ID NO: 58 (GQAP), SEQ ID NO: 59 (GPAQ), SEQ ID NO: 60 (GPQA), SEQ ID NO: 61 (GSQP), SEQ ID NO: 62 (GASP). SEQ ID NO: 63 (GPAS), SEQ ID NO: 64 (GPSA), SEQ ID NO: 65 (GGGS), SEQ ID NO: 66 (GSGS), SEQ ID NO: 67 (GGGGS), SEQ ID NO: 68 (GQEPGQAP), SEQ ID NO: 69: (GQAPGQEP), SEQ ID NO: 70 (SEPATSGSETPGTSESATPESGPGTSTEPSEG), SEQ ID NO: 71 (SEPATS), SEQ ID NO: 72 (GSETPG), SEQ ID NO: 73 (TSESAT), SEQ ID NO: 74 (PESGPG), SEQ ID NO: 75 (TSTEPS) and GS.

In some embodiments, the polypeptide linker comprises (Repeat1)r(Repeat2)s(Repeat3)x(Repeat4)y, wherein Repeat1, Repeat2, Repeat3 and Repeat4 are linked via a peptide bond or via one or more amino acid residues, Repeat1 Repeat2, Repeat3 and Repeat4 independently, comprise or consist of a sequence selected from the group consisting of: SEQ ID NO: 45 (GQEPGAQP), SEQ ID NO: 46 (GAQPGAQP), SEQ ID NO: 47 (GQEP), SEQ ID NO: 48 (GAQP), SEQ ID NO: 49 (GAQPGQEPGAQP), SEQ ID NO: 50 (GAQPGQEP), SEQ ID NO: 51 (GEQP), SEQ ID NO: 52 (GPQE), SEQ ID NO:53 (GPEQ), SEQ ID NO: 54 (GSEP), SEQ ID NO: 55 (GESP), SEQ ID NO: 56 (GPSE), SEQ ID NO: 57 (GPES), SEQ ID NO: 58 (GQAP), SEQ ID NO: 59 (GPAQ), SEQ ID NO: 60 (GPQA), SEQ ID NO: 61 (GSQP), SEQ ID NO: 62 (GASP), SEQ ID NO: 63 (GPAS), SEQ ID NO: 64 (GPSA), SEQ ID NO: 65 (GGGS), SEQ ID NO: 66 (GSGS), SEQ ID NO: 67 (GGGGS), SEQ ID NO: 68 (GQEPGQAP), SEQ ID NO: 69 (GQAPGQEP), SEQ ID NO: 70 (SEPATSGSETPGTSESATPESGPGTSTEPSEG), SEQ ID NO: 71 (SEPATS), SEQ ID NO: 72 (GSETPG), SEQ ID NO: 73 (TSESAT), SEQ ID NO: 74 (PESGPG), SEQ ID NO: 75 (TSTEPS) and GS, and r, s, x and y are independently an integer selected from 0 to 30 or 0 to 20, provided that r, s, x and y are not 0 at the same time.

In some embodiments, x and y are 0, r, and s are independently an integer selected from 1 to 30, and Repeat1 and Repeat2 are a combination selected from the group consisting of:
a) Repeat1 comprises or consists of a sequence of SEQ ID NO: 45, Repeat2 comprises or consists of a sequence of SEQ ID NO: 48;
b) Repeat1 comprises or consists of a sequence of SEQ ID NO: 47, Repeat2 comprises or consists of a sequence of SEQ ID NO: 48;
c) Repeat1 comprises or consists of a sequence of SEQ ID NO: 48, Repeat2 comprises or consists of a sequence of SEQ ID NO: 47;
d) Repeat1 comprises or consists of a sequence of SEQ ID NO: 48, Repeat2 comprises or consists of a sequence of SEQ ID NO: 45;
e) Repeat1 comprises or consists of a sequence of SEQ ID NO: 49, Repeat2 comprises or consists of a sequence of SEQ ID NO: 48;
f) Repeat1 comprises or consists of a sequence of SEQ ID NO: 70, Repeat2 comprises or consists of a sequence of SEQ ID NO: 48;
g) Repeat1 comprises or consists of a sequence of SEQ ID NO: 48, Repeat2 comprises or consists of a sequence of SEQ ID NO: 68 and
h) Repeat1 comprises or consists of a sequence of SEQ ID NO: 70, Repeat2 comprises or consists of a sequence of SEQ ID NO: 47.

In some embodiments, r, x and y are 0, s is an integer selected from 1 to 30 or 0 to 20, and Repeat1 comprises or consists of a sequence of SEQ ID NO: 45.

In some embodiments, y is 0, r, s and x are independently an integer selected from 1 to 30, and Repeat1 Repeat2, and Repeat 3 are a combination selected from the group consisting of:
a) Repeat1 comprises or consists of a sequence of SEQ ID NO: 48, Repeat2 comprises or consists of a sequence of SEQ ID NO: 49; and Repeat3 comprises or consists of a sequence of SEQ ID NO: 48;
b) Repeat1 comprises or consists of a sequence of SEQ ID NO: 48, Repeat2 comprises or consists of a sequence of SEQ ID NO: 47; and Repeat3 comprises or consists of a sequence of SEQ ID NO: 48;
c) Repeat1 comprises or consists of a sequence of SEQ ID NO: 70, Repeat2 comprises or consists of a sequence of SEQ ID NO: 47; Repeat3 comprises or consists of a sequence of SEQ ID NO: 48;
d) Repeat1 comprises or consists of a sequence of SEQ ID NO: 70, Repeat2 comprises or consists of a sequence of SEQ ID NO: 48; Repeat3 comprises or consists of a sequence of SEQ ID NO: 47,
e) Repeat1 comprises or consists of a sequence of SEQ ID NO: 45, Repeat2 comprises or consists of a sequence of SEQ ID NO: 58; Repeat3 comprises or consists of a sequence of SEQ ID NO: 48,
f) Repeat1 comprises or consists of a sequence of SEQ ID NO: 48, Repeat2 comprises or consists of a sequence of SEQ ID NO: 68; Repeat3 comprises or consists of a sequence of SEQ ID NO: 45,
g) Repeat1 comprises or consists of a sequence of SEQ ID NO: 48, Repeat2 comprises or consists of a sequence of SEQ ID NO: 45; Repeat3 comprises or consists of a sequence of SEQ ID NO: 48, and
h) Repeat1 comprises or consists of a sequence of SEQ ID NO: 48, Repeat2 comprises or consists of a sequence of SEQ ID NO: 45; Repeat3 comprises or consists of a sequence of SEQ ID NO: 68.

In some embodiments, r, s, x and y are independently an integer selected from 1 to 30 or 0 to 20, and Repeat1, Repeat2, Repeat 3 and Repeat 4 are a combination selected from the group consisting of:
a) Repeat1 comprises or consists of a sequence of SEQ ID NO: 48, Repeat2 comprises or consists of a sequence of SEQ ID NO: 50; Repeat3 comprises or consists of a sequence of SEQ ID NO: 47, and Repeat4 comprises or consists of a sequence of SEQ ID NO: 48,
b) Repeat1 comprises or consists of a sequence of SEQ ID NO: 45, Repeat2 comprises or consists of a sequence of SEQ ID NO: 68; Repeat3 comprises or consists of a sequence of SEQ ID NO: 45, and Repeat4 comprises or consists of a sequence of SEQ ID NO: 48.
c) Repeat1 comprises or consists of a sequence of SEQ ID NO: 48, Repeat2 comprises or consists of a sequence of SEQ ID NO: 68; Repeat3 comprises or consists of a sequence of SEQ ID NO; 45, and Repeat4 comprises or consists of a sequence of SEQ ID NO: 48,
d) Repeat1 comprises or consists of a sequence of SEQ ID NO: 48, Repeat2 comprises or consists of a sequence of SEQ ID NO: 58; Repeat3 comprises or consists of a sequence of SEQ ID NO: 48, and Repeat4 comprises or consists of a sequence of SEQ ID NO: 45, and
e) Repeat1 comprises or consists of a sequence of SEQ ID NO; 48, Repeat2 comprises or consists of a sequence of SEQ ID NO: 45; Repeat3 comprises or consists of a sequence of SEQ ID NO: 69, and Repeat4 comprises or consists of a sequence of SEQ ID NO: 68.

In some embodiments, the peptide linker comprises an amino acid sequence selected from the group consisting of SEQ ID NOs: 76-89, except that one residue is substitute by the CRM residue.

In some embodiments, the peptide linker comprises an amino acid sequence selected from the group consisting of SEQ ID NOs: 90-117, 175, and 176.

In some embodiments, the polypeptide conjugate comprises or consists of an amino acid sequence selected from the group consisting of SEQ ID NOs; 118-174, 177-183; and 185-190.

In some embodiments, the CRM comprises a plasma protein-binding moiety, a polymer, Fc, HSA (albumin), Xten sequence, or PAS sequence.

In some embodiments, the CRM comprises an albumin-binding moiety.

In some embodiments, the albumin-binding moiety comprises a structure of: *-A-B-C-D-E, wherein A, B, C, D and E are interconnected via amide bonds, and the * end of A is connected to a reactive group of the CRM residue in the polypeptide complex, and wherein:

A is selected from a bond,

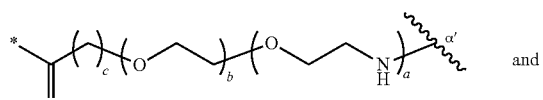

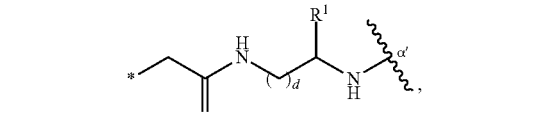

a, b, c and d are independently an integer from 0 to 4, $R^1$ is hydrogen or —COOH;

B is selected from a bond,

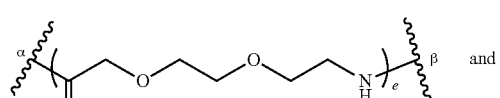

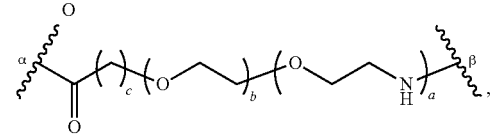

wherein position α is linked to position α', e is an integer from 1 to 4,

C is a bond or

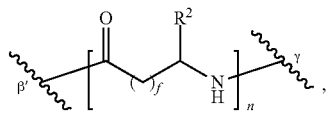

$R^2$ is —CH$_2$SO$_3$H or —COOH, f is an integer from 1 to 4, n is an integer from 1 to 25, wherein when B is not bond, then position β' is linked to position β, or when B is bond, then position β' is linked to position α';

D is selected from a bond,

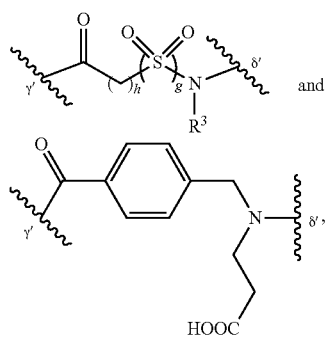

g and h are independently 0 or 1, and $R^3$ is H or —CH$_2$COOH, wherein:
when B is not a bond and C is a bond, then position γ' is linked to position β;
when C is not a bond, then position γ' is linked to position γ; and
when B is a bond and C is a bond, then position γ' is linked to position α;

E is an acidic group having a formula:

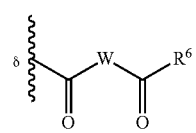

(I)

wherein W represents —(CR$^4$R$^5$)$_f$—,
$R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide,
$R^6$ is selected from hydroxyl or NR$^7$R$^8$;
$R^7$ and $R^8$ are independently selected from the group consisting of hydrogen, alkyl, hydroxyl, and

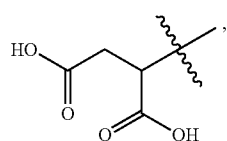 [SMILES: *C(CC(=O)O)C(=O)O]

and
I is an integer from 10 to 20, from 10 to 18, from 10 to 16, for example, 12, 14, 16, or 18 and wherein:
when D is not a bond, then position δ is linked to position δ',
when C is not a bond and D is a bond, then position δ is linked to position γ,
when B is not a bond, C is a bond and D is a bond, then position δ is linked to position β,
when A is not a bond, and all of B, C, and D are bond, then position δ is linked to position α',
or a pharmaceutically acceptable salt thereof.

In some embodiments, wherein the CRM is conjugated to a lysine residue.

In some embodiments, A is a bond.

In some embodiments, A is a bond, and B is a bond or

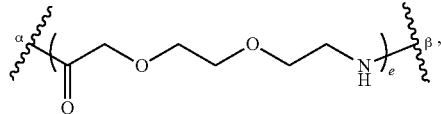

wherein e is 1, 2 or 3.

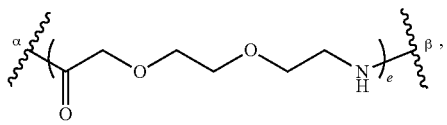

In some embodiments, A is a bond, B is and C is

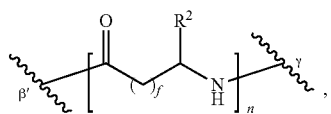

wherein position β' is linked to position β, wherein e is 1, 2 or 3, f is 1, 2, or 3, and n is 1 or 2. In certain embodiments, D is a bond, and E is an acidic group having a formula:

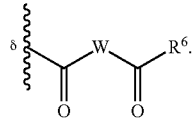

In certain embodiments, $R^2$ is —COOK and $R^6$ is hydroxyl. In certain embodiments, W represents —$(CR^4R^5)_I$—, $R^4$ and $R^5$ are independently hydrogen, I is an integer from 10 to 20, from 10 to 18, from 10 to 16, for example, 12, 14, 16, or 18.

In some embodiments, A is a bond, B is a bond, and C is a bond.

In some embodiments, A is a bond, B is a bond, and C is

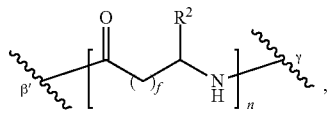

wherein f is 1, 2, or 3, and n is 1 or 2.

In some embodiments, A is

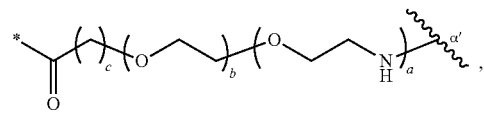

wherein a is 1, 2 or 3, b is, 2 or 3, and c is 1 or 2.

In some embodiments, A is

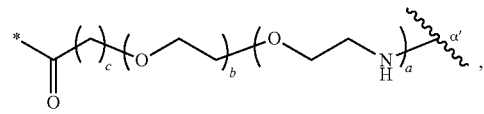

and B is

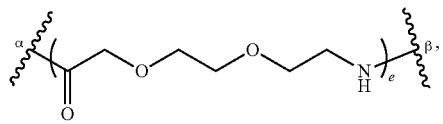

wherein position α is linked to position α', wherein a is 1, 2 or 3, b is 1, 2 or 3, c is 1 or 2, and e is 1, 2 of 3.

In some embodiments, A is

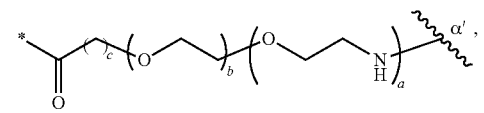

B is

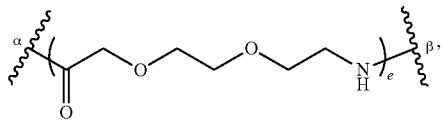

and C is

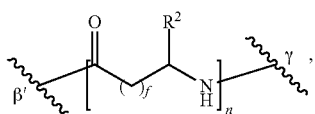

wherein position α is linked to position α' and position β' is linked to position β, wherein a is 1, 2 or 3, b is 1, 2 or 3, c is 1 or 2, e is 1, 2 or 3, f is 1, 2, or 3, and n is 1 or 2.

In some embodiments, A is

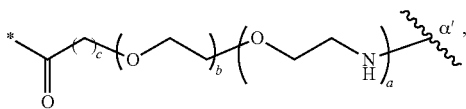

B is

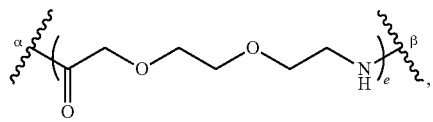

and C is bond, wherein position α is linked to position α', wherein a is 1, 2 or 3, b is 1, 2 or 3, c is 1 or 2, and e is 1, 2 or 3.

In some embodiments, A is

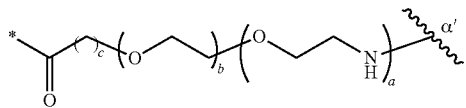

and B is a bond, wherein a is 1, 2 or 3, b is 1, 2 or 3, and c is 1 or 2.

In some embodiments, A is

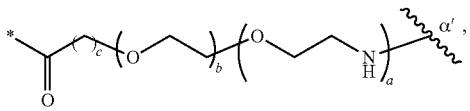

B is a bond, and C is

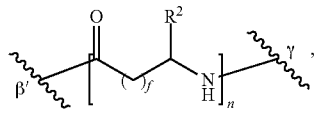

wherein position β' is linked to position α', wherein a is 1, 2 or 3, b is 1, 2 or 3, c is 1 or 2, f is 1, 2, or 3, and n is 1 or 2.

In some embodiments, A is

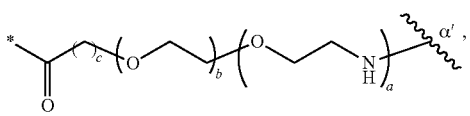

B is a bond, and C is a bond, wherein a is 1, 2 or 3, b is 1, 2 or 3, and c is 1 or 2.

In some embodiments, D is a bond.
In some embodiments, A is

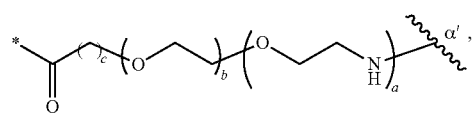

B is

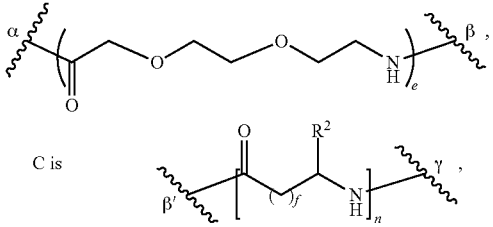

C is 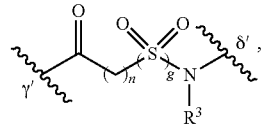

and D is a bond, wherein position α is linked to position α' and position β' is linked to position β, wherein a is 1, 2 or 3, b is 1, 2 or 3, c is 1 or 2, e is 1, 2 or 3, f is 1, 2, or 3, and n is 1 or 2.

In some embodiments, D is

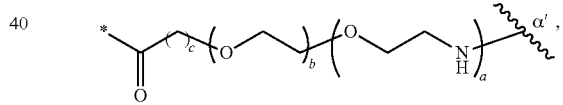

wherein g is 0 or 1, and h is 0 or 1.
In some embodiments, A is

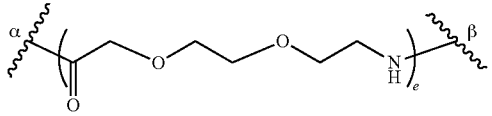

B is

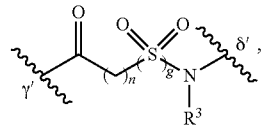

or a bond, C is a bond, and D is

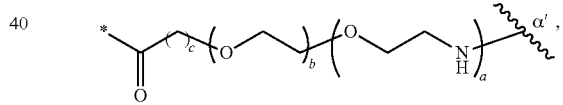

wherein a is 1, 2 or 3, b is 1, 2 or 3, c is 1 or 2, e is 1, 2 or 3, g is 0 or 1, and h is 0 or 1, wherein when B is not a bond, then position α is linked to position α' and position γ' is linked to position β, wherein when B is a bond, then position γ' is linked to position α'.

In some embodiments, D is

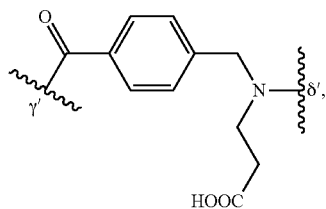 [SMILES: *C(=O)c1ccc(CN(*)CCC(=O)O)cc1]

In some embodiments, A is

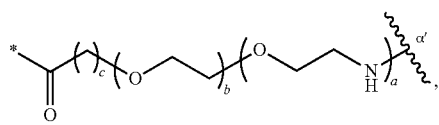

B is

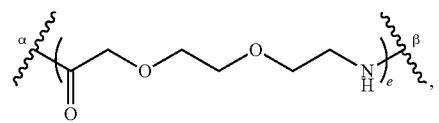

C is a bond or

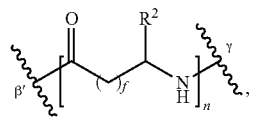

and D is

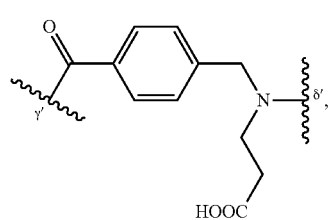 [SMILES: *C(=O)c1ccc(CN(*)CCC(=O)O)cc1]

wherein when C is a bond, then position α is linked to position α' and position γ' is linked to position β, or when C is not a bond, then position α is linked to position α', position β' is linked to position β, and position γ' is linked to position γ, wherein a is 1, 2 or 3, b is 1, 2 or 3, c is 1 or 2, e is 1, 2 or 3, f is 1, 2, or 3, and n is 1 or t.

In some embodiments, the CRM comprises the structure of below formula:

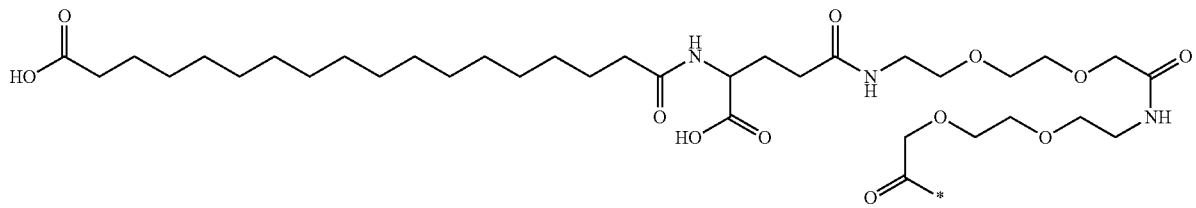 [SMILES: *C(=O)COCCOCCNC(=O)COCCOCCNC(=O)CCC(NC(=O)CCCCCCCCCCCCCCCCC(=O)O)C(=O)O]

In some embodiments, the CRM is conjugated to a cysteine residue.

In some embodiments, A is

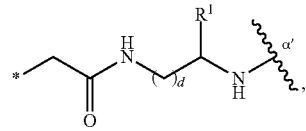

and B is

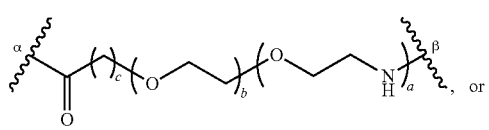

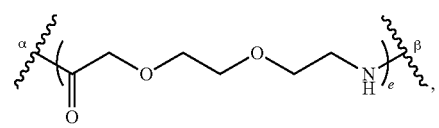

wherein position α is linked to position α'.

In some embodiments, A is

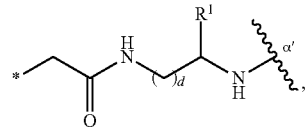

B is

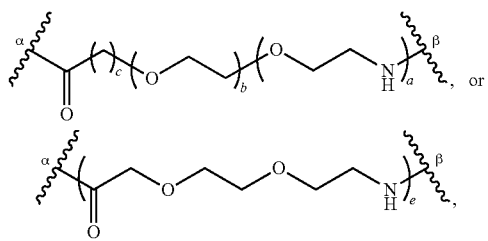, or and C is

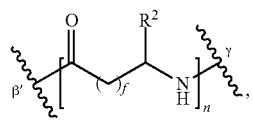, wherein position α is linked to position α' and position β' is linked to position β, wherein a is 1, 2 or, b is 1, 2 or 3, c is 1 or 2, d is 1, 2, or 3, f is 1, 2, or 3, and n is 1 or 2. In certain embodiments, D is a bond, and E is an acidic group having a formula:

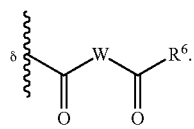

In certain embodiments, $R^2$ is —COOH, and $R^6$ is hydroxyl. In certain embodiments, W represents —$(CR^4R^5)_I$—, $R^4$ and $R^5$ are independently hydrogen, I is an integer from 10 to 20, from 10 to 18, from 10 to 16, for example, 12, 14, 16, or 18.

In some embodiments, A is

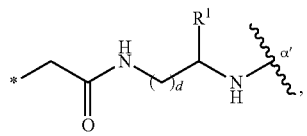

B is

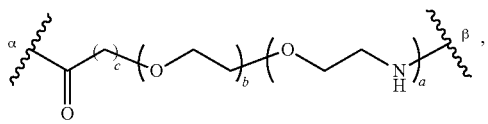,

C is

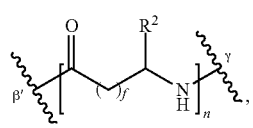, and D is a bond, wherein position α is linked to position α' and position β' is linked to position β, wherein a is 1, 2 or 3, b is 1, 2 or 3, c is 1 or 2, d is 1, 2, or 3, f is 1, 2, or 3, and n is 1 or 2.

In some embodiments, A is

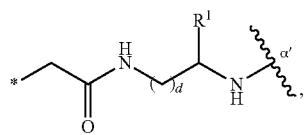, and B is

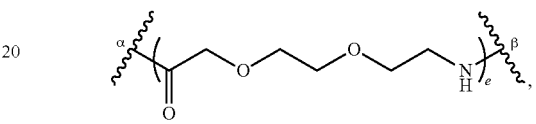, wherein position α is linked to position α', wherein d is 1, 2, or 3, and e is 1, 2 or 3.

In some embodiments, A is

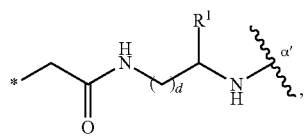,

B is

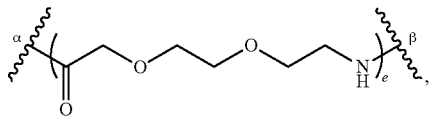, and C is a bond, wherein position α is linked to position α', wherein d is 1, 2, or 3, and e is 1, 2 or 3.

In some embodiments, A is

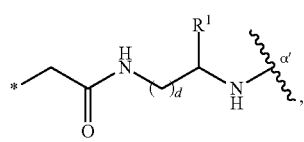,

B is

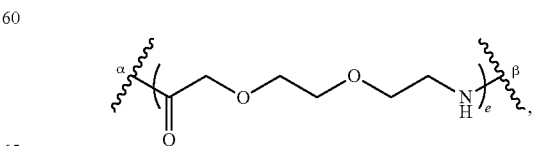,

C is a bond, and D is

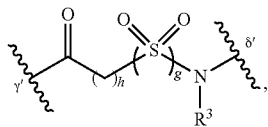

wherein position α is linked to position α' and position γ' is linked to position β, wherein d is 1, 2, or 3, e is 1, 2 or 3, g is 0 or 1, and h is 0 or 1.

In some embodiments, the CRM comprises the structure of below formula:

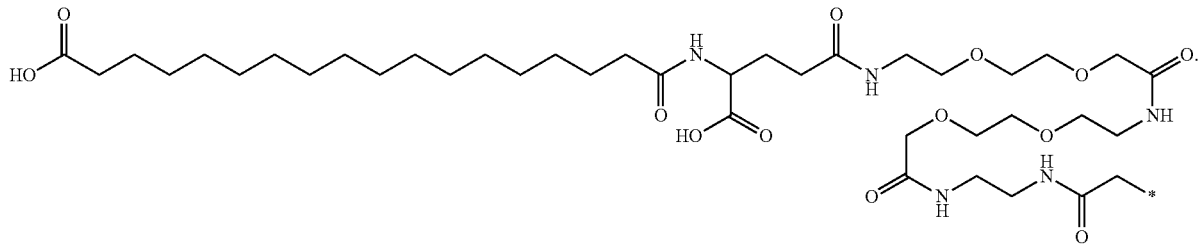 [SMILES: *CC(=O)NCCNC(=O)COCCOCCNC(=O)COCCOCCNC(=O)CCC(NC(=O)CCCCCCCCCCCCCCCCC(=O)O)C(=O)O]

In a second aspect, the present disclosure provides a polynucleotide encoding the polypeptide portion (or fragment thereof) of the polypeptide conjugate of the first aspect.

In a third aspect, the present disclosure provides a vector comprising the polynucleotide of the second aspect.

In a fourth aspect, the present disclosure provides a host cell comprising the vector of the third aspect.

In some embodiments, the host cell is a prokaryotic cell or eukaryotic cell.

In a fifth aspect, the present disclosure provides a method of producing the polypeptide conjugate of the first aspect, comprising culturing the host cell of the fourth aspect under a condition that allows expression of the polynucleotide of the second aspect to obtain the polypeptide portion of the polypeptide conjugate.

In some embodiments, the host cell is prokaryotic cell or a eukaryotic cell.

In some embodiments, the polypeptide portion is expressed as soluble proteins.

In some embodiments, the method further comprises conjugating the CRM to the polypeptide portion.

In a sixth aspect, the present disclosure provides a pharmaceutical composition comprising the polypeptide conjugate according to the first aspect and a pharmaceutically acceptable salt.

In a seventh aspect, the present disclosure provides a method of preventing or treating a metabolic disorder in a subject in need thereof, comprising administering a therapeutically effective amount of the polypeptide conjugate of the first aspect.

In an eighth aspect, the present disclosure provides a method of managing body weight in a subject in need thereof, comprising administering a therapeutically effective amount of the polypeptide conjugate provided herein, thereby managing body weight of the subject.

In a ninth aspect, the present disclosure provides a method of reducing food intake in a subject in need thereof, comprising administering a therapeutically effective amount of the polypeptide conjugate provided herein, thereby reducing food intake of the subject.

In a tenth aspect, the present disclosure provides a method of reducing body weight in a subject in need thereof, comprising administering a therapeutically effective amount of the polypeptide conjugate provided herein, thereby reducing body weight of the subject.

In certain embodiments, the metabolic disorder is diabetes, obesity, overweight, non-alcoholic steatohepatitis (NASH), cardiovascular like dyslipidemia, artherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

In certain embodiments, the diabetes can any form of diabetes, including without limitation, hyperglycemia, type 2 diabetes, impaired glucose tolerance, type 1 diabetes, non-insulin dependent diabetes, MODY (maturity onset diabetes of the young), gestational diabetes, and elevated level of HbA1C.

In certain embodiments, the subject is human.

In certain embodiments, the subject has a fasting blood glucose level of 125 mg/dL or greater.

In certain embodiments, the subject has a body mass index (BMI) of at least or higher than 25.

In certain embodiments, the polypeptide conjugate is administered at a dosing regimen that is no more frequently than once daily, once every 3 days, or once weekly, once every two weeks, once every three weeks, or once monthly.

In certain embodiments, the polypeptide conjugate is administered twice-weekly, once-weekly, once bi-weekly, once every three weeks, once monthly, or once every two months.

In certain embodiments, the dosing regimen has a dosing interval ranging from about once every 3 days to about once per month, or from about once weekly to about once per month.

In certain embodiments, the polypeptide conjugate is administered subcutaneously or intravenously or orally.

Throughout the present disclosure, the articles "a," "an," and "the" are used herein to refer to one or to more than one (i.e., to at least one) of the grammatical object of the article. By way of example, "a fusion polypeptide" means one fusion polypeptide or more than one fusion polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

BRIEF DESCRIPTION OF THE FIGURES

FIG. 1A shows body weight loss after Molecule 001 treatment from Day 1 to Day 8. FIG. 1B shows body weight loss after Molecule 002 treatment from Day 1 to Day 8. FIG. 1C shows body weight loss after Molecule 012 or Molecule 001 treatment from Day 1 to Day 8.

FIG. 2A shows fasting glucose after Molecule 001 single dose treatment. FIG. 2B shows fasting glucose after Molecule 002 single dose treatment. Data are indicated as mean values and standard error (SEM). FIG. 2C shows non-fasting glucose after Molecule 012 single dose treatment. FIG. 2D shows non-fasting glucose after Molecule 019 single dose treatment, and FIG. 2E shows area under the curve for 0-48 hours for non-fasting glucose after Molecule 019 single dose treatment. To evaluate the glucose, 10-week old male db/db mice were administered subcutaneously with the designated GLP-1 polypeptide conjugates at the indicated dosage. Fasting glucose (FIGS. 2A and 2B) or non-fasting glucose (FIG. 2C) was measured on different times and five animals were used for each group. Delta blood glucose is glucose subtracted by baseline level. Data are indicated as mean values and standard error (SEM).

FIG. 3A shows body weight change with dose titrations of Molecule 012 at 10, 30 and 100 nmol/kg. FIG. 3B shows fasting glucose change upon treatment. Data are expressed as mean values and standard error (SEM).

FIGS. 4A-4M show all the sequences disclosed in the present disclosure.

DETAILED DESCRIPTION

Figure 1A:
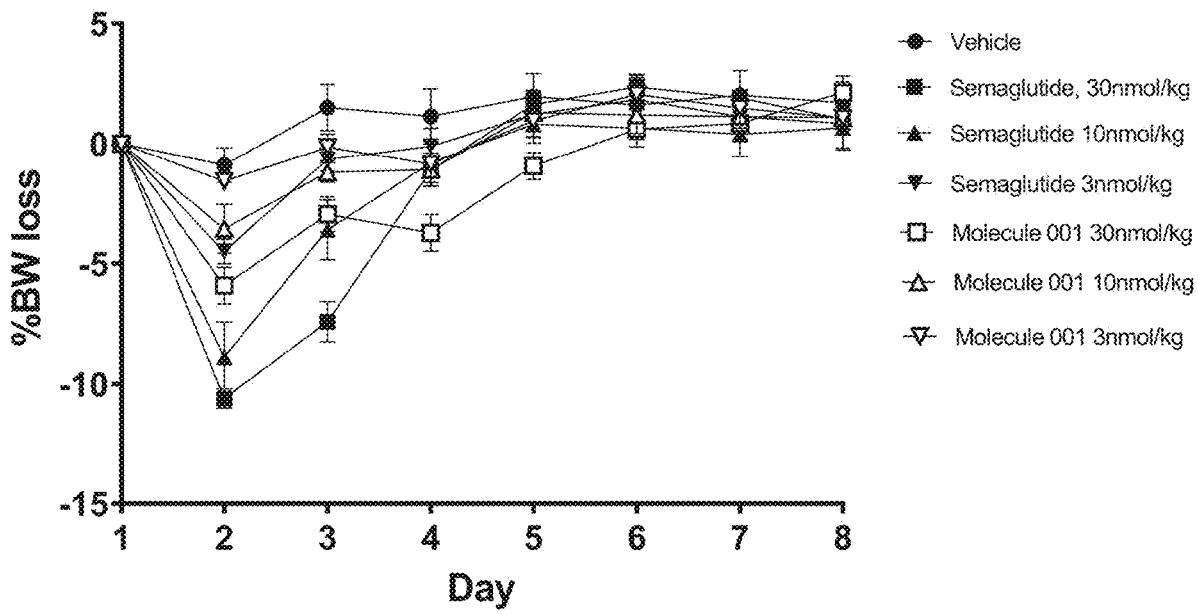
FIGS. 1A to 1C show in vivo activities of Molecule 001, 002 and 012 in C57BL/6 mice. To evaluate the body weight, 10-week old male C57BL/6 mice were dosed subcutaneously with testing drug substances once.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

The term "amino acid" as used herein refers to an organic compound containing amine ($-NH_2$) and carboxyl ($-COOH$) functional groups, along with a side chain specific to each amino acid.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Tip or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, γ-carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofarnesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (Tle), b-alanine, 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl)carboxylic acid, and (1-aminocyclooctyl)carboxylic acid.

Introduction of non-natural amino acids into a polypeptide may be realized by the technology described in Wang et al., Science 292:498-500, 2001; Deiters et al., J Am Chem Sac 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons; such as a four-base codon (e.g. AGGA, AGGU, CGGU; CGCU, CGAU, CCCU; CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice. For another example, non-natural amino acid can be chemically synthesized and inserted into or attached to a polypeptide by chemical reaction such as acylation.

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology; 266:383-402 (1996); Larkin M. A. et al; Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gin), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional form" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide. A variant may differ from the parent peptide by one or more amino acid residues. For example, a variant may have substitutions, additions, deletions, insertions, or truncations of one more amino acid residue of the parent polypeptide.

The term "fragment" as used herein refers to partial sequence of the parent polypeptide of any length. A fragment can still retain at least partial function of the parent polypeptide.

The term "derivative" as used herein refers to a chemically modified polypeptide or fusion polypeptide, in which one or more well-defined number of substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker, Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on, Polypeptide Conjugates In one aspect, the present disclosure provides a polypeptide conjugate comprising: a single biologically active peptide attached to N-terminus of a peptide linker, and a first clearance-reducing moiety (CRM) conjugated to a first CRM residue in the peptide linker, wherein: the biologically active peptide comprises a GLP-1 receptor agonist, and the first CRM residue is at least 5 amino acid residues (exclusive of the CRM residue) away from the C-terminal amino acid residue of the GLP-1 receptor agonist.

The term "peptide" and "polypeptide" are used interchangeably herein and refer a polymer of amino acid residues linked by covalent bonds such as peptide bonds. A peptide or polypeptide as provided herein can comprise naturally occurring or non-natural amino acid residues, or both. Polypeptides and peptides provided herein can comprise any suitable length of amino acid residues, for example, from at least 5, 10, 20, 30, 40, 50, 60, 70, 80, 90, 100, 200, 300, 400, 500, 600, 700, 800, 900, 1000, or more amino acid residues in length.

The polypeptide conjugate comprise a single, i.e., only one, biologically active peptide. "Single" with respect to biologically active peptide is intended to mean that the polypeptide conjugate does not contain two or more different biologically active peptides which are attached respectively to the peptide linker. The single biologically active peptide, however, can include fragments or portions from different biologically active peptides fused together, for example, as a hybrid or chimera, as long as these portions are integrated as one peptide and are not respectively attached to the linker. If, however, two different biologically active peptides are attached respectively to the N-terminus and the C-terminus of the linker, then that is not a single biologically active peptide as used in the present disclosure.

The term "biologically active peptide" as used herein means a peptide having a biological function or activity, for example, a physiological function, or a therapeutic function. In certain embodiments, the biologically active peptide is therapeutically active. A peptide which, when stand alone, does not have biological function is not a biologically active peptide. For example, a peptide linker is not a biologically active peptide unless it has its own biological function or activity, for example when used alone.

The biologically active peptide comprises a Glucagon-like peptide-1 (GLP-1) receptor agonist.

The term "Glucagon-like peptide-1 (GLP-1) receptor" (also referred to as GLP1R) is a receptor protein found on beta cells on the pancreas and on neurons of the brain, comprising one extracellular domain and one transmembrane domain. The extracellular domain can bind to the C-terminal helix of GLP-1, and the transmembrane domain can bind to the N-terminal regions of GLP-1. The GLP-1 receptor is involved in the control of blood sugar level by enhancing insulin secretion. When expressed in the brain, the GLP-1 receptor can also be involved in the control of appetite.

The term "Glucagon-like peptide-1 (GLP-1) receptor agonist" or "GLP-1 receptor agonist" as used herein refers to a molecule which is capable of binding to and activating the GLP-1 receptor. A GLP-1 receptor agonist may elicit a magnitude of GLP-1 receptor response that is similar to or partial of a natural ligand.

The term "clearance-modifying moiety" or "CRM" as used herein refers to moiety that can alter one or more pharmacokinetic (PK) properties (for example, to increase the half-life in vivo). Examples of CRMs can include, without limitation, fatty acid, polyethylene glycol (PEG), glucuronic acid or other sugar based linkers, polar, positively or negatively charged groups that can increase the rates of hydrolysis of a succinimidyl ring and reduce or minimize the rate of reverse Michael reaction, therefore reduce or minimize the rate of loss of drug and the linker group from the biologically active peptide to other thiol-containing proteins and small molecules.

"CRM residue" as used herein refers to the amino acid residue that is conjugated to a CRM.

The term "conjugate" as used herein refers to a compound as a result of two or more molecules joined together to form one physical entity. For example, the conjugate of the present disclosure means a compound as a result of the polypeptide and one or more clearance-modifying moieties joined together. The molecules may attach together by covalent, non-covalent bonds, linkers, chemical modification, or protein fusion or by any means known to one skilled in the art. Preferably, the molecules may attach together by covalent bonds. The joining may be permanent or reversible. In some embodiments, certain cleavable or non-cleavable linkages may be included.

While conjugation of a CRM to a GLP-1 receptor agonist may extend half-life of the GLP-1 receptor agonist, it could also adversely affect the biological activity of the GLP-1 receptor agonist, rendering it less active than the unconjugated counterpart. For example, semaglutide, a conjugated GLP-1 derivative, has a significantly extended half-life, but suffers from a 939-fold loss in GLP-1 receptor binding in presence of human serum albumin (HSA) relative to its unconjugated counterpart (J. Med. Chem. 2015, 58, 7370-7380).

However, it is unexpectedly found by the inventors that, certain CRM-conjugated polypeptide comprising GLP-1 receptor agonist can have both an extended half-life and retained biological activity, if the CRM is conjugated outside of the GLP-1 receptor agonist on a peptide linker attached to its C-terminus. Interestingly, the distance between the C-terminus of the GLP-1 receptor agonist and the conjugation site has been found by the inventors to be of particular importance. If the CRM conjugation on the peptide linker is at a position close to the C-terminus of the GLP-1 receptor agonist, it would significantly reduce biological activity, which could be even much lower than conjugation on the GLP-1 receptor agonist itself. However, if the conjugation is at a position sufficiently farther away from the C-terminus of the GLP-1 receptor agonist, then the CRM-conjugated GLP-1 receptor agonist could have both extended half-life and retained biological activity. Such unexpected effects are found with certain GLP-1 receptor agonists and certain CRMs.

In certain embodiments, the first CRM residue is at least 10, 15, 20, 21, 22, 23, 24, 25, 26, 27, 28, 29, 30, 31, 32, 35, 38, 40, 45, 46, 50, 55, 58, 60, 65, 70, 75, or 78 amino acid residues (exclusive of the CRM residue) away from the C-terminal amino acid residue of the GLP-1 receptor agonist. In certain embodiments, the distance between the first CRM residue and the C-terminal amino acid of the GLP-1 receptor agonist is between 10 to 120, 15 to 120, 20 to 120, 25 to 120, 30 to 120, 31 to 120, 32 to 120, 33 to 120, 34 to 120, 35 to 120, 36 to 120, 37 to 120, 38 to 120, 39 to 120, 40 to 120, 30 to 80, 31 to 80, 32 to 80, 33 to 80, 34 to 80, 35 to 80, 36 to 80, 37 to 80, 38 to 80, 39 to 80, or 40 to 80.

In certain embodiments, the GLP-1 receptor agonist in the polypeptide conjugate has a length of no more than 70, 60, or 50 amino acid residues. In certain embodiments, the GLP-1 receptor agonist in the polypeptide conjugate has a length of no more than 49, 48, 47, 46, 45, 44, 43, 42, 41, 40, 39, 38, 37, 36, 35, 34, 33, 32, 31, or 30 amino acid residues.

In certain embodiments, the GLP-1 receptor agonist in the polypeptide conjugate comprises or is GLP-1 as provided in the present disclosure. In some embodiments, the GLP-1 in the polypeptide conjugates provided herein comprises an amino acid sequence selected from the group consisting of: SEQ ID NOs: 1, 3, 5, 7, 8, 10, 12, 13, 15, 17, 18, 20, 22, 23, 25, 27, 28, 30, 32, 33, 35, 36, 38, 40-44, and 184. In certain embodiments, the GLP-1 in the polypeptide conjugates comprises or consists of an amino acid sequence of SEQ ID NO: 3 (8Aib, 34R, 36G), or SEQ ID NO: SEQ ID NO: 8 (8Aib, 22E, 34R, 36G).

Without wishing to be bound by any theory, it is believed that CRM (or fatty acid) conjugation to GLP-1 can reduce its activity in the presence of HSA. For example, the reduction in GLP-1 activity has been reported for semaglutide, which has a fatty acid conjugated to K26 of GLP-1 (8Aib, 36R) and showed significant reduction in activity compared to its non-conjugated counterpart in the presence of HSA. Since HSA is present in human blood and is unavoidable under physiological conditions, reduction in GLP-1 receptor agonist activity in the presence of HSA is believed to compromise therapeutic activity of the protein conjugates. However, some of the polypeptide conjugates provided herein can retain most of the GLP-1 activity in the presence of HSA despite of CRM conjugation. In such embodiments, the polypeptide conjugates provided herein is mono-conjugated, and has the CRM conjugated to the peptide linker but not to the biologically active peptide (e.g. GLP-1).

In some of these embodiments, such mono-conjugated polypeptide conjugates provided herein has increased GLP-1 receptor agonist activity in the presence of HSA, compared to a comparative polypeptide conjugate without the peptide linker and having a CRM conjugated on the GLP-1. In certain embodiments, the GLP-1 receptor agonist activity in the presence of HSA can be determined in an in vitro assay for GLP-1 receptor activation, either in a cell free assay such as cAMP assay or in a cell-based assay such as reporter cell assay, as known in the art. In certain embodiments, the comparative polypeptide conjugate is semaglutide. In certain embodiments, the mono-conjugated polypeptide conjugates provided herein activates GLP-1 receptor in the presence of human serum albumin (HSA) at an EC50 no more than 50% (or no more than 40%, 30%, 20%, 10%, 5%, or 3%) than that of semaglutide in the presence of HSA, as determined in the same or comparable assay. In certain embodiments, the mono-conjugated polypeptide conjugates provided herein activates GLP-1 receptor in the absence of HSA at an EC50 comparable to (e.g. from 20% to 300% of) that of semaglutide in the absence of HSA, as determined in the same or comparable assay. In certain embodiments, the amount of human serum albumin (HSA) allows assessment of impact of HSA binding to the GLP-1 receptor activation. In certain embodiments, the in vitro assay for GLP-1 receptor activation is conducted in the presence of at least 0.5%, 1%, 1.2%, 1.5%, 1.8% or 2% HSA.

In certain embodiments, the mono-conjugated polypeptide conjugates provided herein binds to HSA at a binding affinity (KD) comparable to (e.g. from about 70% to about 500% of) that of semaglutide, as determined in the same or comparable assay.

In certain embodiments, the mono-conjugated polypeptide conjugates provided herein has at least comparable terminal half life compared to a comparative polypeptide conjugate without the peptide linker and having a CRM conjugated on the GLP-1, such as semaglutide, as determined under comparable in vivo study conditions and in the same type of experimental animals. Suitable animals for terminal half life determination include for example mice, rats, minipigs, or monkeys. In certain embodiments, the terminal half-life is determined in a suitable animal after a single dose intravenous administration or subcutaneous administration or oral administration at a dose suitable for providing therapeutic efficacy.

In certain embodiments, the polypeptide conjugates further comprise a second CRM conjugated to a second CRM residue. In other words, the present disclosure also provides double-conjugated polypeptide conjugate. It is unexpectedly found by the inventors that a second CRM conjugation can further extend the half-life of the polypeptide conjugate. In certain embodiments, the double-conjugated polypeptide conjugate having both the first and the second CRM conjugations can have an extended half-life that is at least 1-fold, 2-fold, 3-fold, 4-fold, 5-fold, 6-fold or even longer than a corresponding polypeptide conjugate (e.g. semaglutide) having only one CRM conjugation.

The second CRM residue can be at any suitable position. In certain embodiments, the second CRM residue is in the GLP-1 receptor agonist or in the peptide linker.

In certain embodiments, the second CRM residue is at K26 of the GLP-1 peptide. It has been reported that conjugation with two fatty acid moieties on a GLP-1 peptide can significantly reduce the activity or even render the conjugated GLP-1 peptide ineffective. It is therefore unexpectedly found by the present inventors that, conjugation both on GLP-1 (e.g. K26) and on the peptide linker at a position sufficiently away from the C-terminus of the GLP-1 peptide, can minimize the negative impact of fatty acid conjugation to the biological activity of GLP-1 polypeptide in the presence of HSA.

In some of these embodiments, such double-conjugated polypeptide conjugates provided herein has a comparable or acceptable GLP-1 receptor agonist activity in the presence of HSA, compared to a comparative polypeptide conjugate without the peptide linker and having a CRM conjugated on the GLP-1. In certain embodiments, the double-conjugated polypeptide conjugates provided herein activates GLP-1 receptor in the presence of HSA at an EC50 of no more than 2000% (or no more than 1500%, 1000%, 900%, 800%, 700%, 600%, or 500%) than that of a comparative polypeptide conjugate without the peptide linker and having a CRM conjugated on the GLP-1, such as semaglutide in the presence of HSA, as determined in the same or comparable assay. In certain embodiments, the double-conjugated polypeptide conjugates provided herein activates GLP-1 receptor in the absence of HSA at an EC50 comparable to (e.g. no more than 500%, 400%, 300%, or 200% of, or even less than) that of a comparative polypeptide conjugate without the peptide linker and having a CRM conjugated on the GLP-1, such as semaglutide, as determined in the same or comparable assay. In certain embodiments, the double-conjugated polypeptide conjugates provided herein activates GLP-1 receptor at a first EC50 in the presence HSA, and at a second EC50 in the absence of HSA, and the first EC50 is higher than the second EC50 but is no more than 1000-fold of that of the second EC50, for example, the first EC50 (in the presence of HSA) is no more than 900-fold, 800-fold, 700-fold, 600-fold, or 500-fold of the second EC50 (in the absence of HSA). In certain embodiments, HSA is present in the in vitro assay for GLP-1 receptor activation at a suitable amount that allows assessment of impact of HSA binding to the GLP-1 receptor activation. In certain embodiments, the in vitro assay for GLP-1 receptor activation is conducted in the presence of a suitable amount of human serum albumin (HSA) that allows assessment of impact of HSA binding to the GLP-1 receptor activation. In certain embodiments, the in vitro assay for GLP-1 receptor activation is conducted in the presence of at least 0.5%, 1%, 1.2%, 1.5%, 1.8% or 2% HSA.

In certain embodiments, the double-conjugated polypeptide conjugates provided herein binds to HSA at a higher binding affinity, represented by a KD value significantly lower than (e.g. no more than 50%, 40%, 30%, or 20% of) that of a comparative polypeptide conjugate without the peptide linker and having a CRM conjugated on the GLP-1, such as semaglutide, as determined in the same or comparable assay.

In certain embodiments, double-conjugated polypeptide conjugates provided herein has enhanced pharmacokinetic properties in comparison to a comparative polypeptide conjugate without the peptide linker and having a CRM conjugated on the biologically active peptide (e.g. GLP-1), wherein the pharmacokinetic properties are determined by measuring blood concentration of the polypeptide conjugate after administration of a therapeutically effective dose to a subject.

In certain embodiments, the double-conjugated polypeptide conjugates provided herein has an increase in terminal half-life by at least 50%, 60%, 70%, 80%, 90%, 100%, 120%, 150%, 180%, 200%, 300%, or 400% than that of a comparative polypeptide conjugate without the peptide linker and having a CRM conjugated on the GLP-1, such as semaglutide, as determined under comparable in vivo study conditions and in the same type of experimental animals. Suitable animals for terminal half life determination include for example mice, rats, minipigs, or monkeys. In certain embodiments, the terminal half-life is determined in a suitable animal after a single dose intravenous administration or subcutaneous administration at a dose suitable for providing therapeutic efficacy.

In certain embodiments, the double-conjugated polypeptide conjugates provided herein has blood or plasma or serum concentrations that remain within therapeutic window for the polypeptide conjugate for a period at least about 50% longer (60%, 70%, 80%, 90%, 100%, 120%, 150%, 180%, 200%, 300%, or 400% longer) that of a comparative polypeptide conjugate without the peptide linker and having a CRM conjugated on the GLP-1, such as semaglutide, as determined under comparable in vivo study conditions and in the same type of experimental animals. The term "therapeutic window" as used herein means that the range of concentration level of the polypeptide conjugates in the blood or plasma or serum that provides for therapeutic benefit or efficacy for the condition to be treated without unacceptable toxicity. The range of concentration level can be from the minimal concentration that results in a therapeutic response to the maximal concentration that provides for therapeutic response yet without inducing unacceptable toxicity.

In certain embodiments, the double-conjugated polypeptide conjugates provided herein provides for an extended duration of therapeutic efficacy in comparison with a comparative polypeptide conjugate without the peptide linker and having a CRM conjugated on the GLP-1, such as semaglutide, as determined under comparable in vivo study conditions and in the same type of experimental animals. Such an extended therapeutic efficacy can be characterized by area under curve (AUC) for time-response curve, which can be plotted after a single dose or after repeated doses that are suitable for providing an intended therapeutic effect in a subject having a metabolic condition (e.g. a disease model animal). The extended therapeutic efficacy duration can also be characterized by the duration of the therapeutic response.

In certain embodiments, the therapeutic response comprises reduction in body weight, reduction in food intake, or reduction in glucose level (fasting glucose level or non-fasting glucose level). In certain embodiments, the double-conjugated polypeptide conjugates provided herein has an increase in the AUC for the time-response curve by at least 50%, 60%, 70%, 80%, 90%, 100%, 120%, 150%, 180%, 200% than that of a comparative polypeptide conjugate without the peptide linker and having a CRM conjugated on the GLP-1, such as semaglutide, as determined under comparable in vivo study conditions and in the same type of experimental animals. In certain embodiments, the double-conjugated polypeptide conjugates provided herein has an increase in duration of the therapeutic response by at least 50%, 60%, 70%, 80%, 90%, 100%, 120%, 150%, 180%, 200%, 300%, or 400% than that of a comparative polypeptide conjugate without the peptide linker and having a CRM conjugated on the GLP-1, such as semaglutide, as determined under comparable in vivo study conditions and in the same type of experimental animals. In certain embodiments, the experimental animals for therapeutic response are disease model animals such as db/db mice, or diet-induced obese (D10) animals.

GLP-1 Receptor Agonist

A GLP-1 receptor agonist can include both a natural ligand of the receptor and an artificially designed or modified molecules that exhibits agonist activity comparable to or no less than 30%, 40% or 50% of that of the natural ligand. In certain embodiments, the GLP-1 receptor agonist comprises the amino acid sequence of native GLP-1, oxyntomodulin, exendin-4, exenatide, beinaglutide, efpeglenatide, langlenatide, semaglutide, taspoglutide, pegapamodutide, liraglutide, albiglutide, dulaglutide, or lixisenatide.

In certain embodiments, the GLP-1 receptor agonist comprises GLP-1.

The term "Glucagon-like peptide-1" or "GLP-1" as used herein is intended to broadly encompasses native GLP-1 peptide and all its functional forms such as its functional variants, fragments, fusions, derivatives and mimetics.

The term "native GLP-1 peptide" as used herein refers to the native human Glucagon-Like Peptide-1 (GLP-1 (7-37)), the sequence of which is set forth in SEQ ID NO:1. As used herein, when referring to a particular amino acid residue in SEQ ID NO: 1 (i.e. GLP-1 (7-37)), the numbering of the GLP-1 (1-37) is followed. In other words, SEQ ID NO: 1 corresponds to GLP-1 (7-37), and therefore the $1^{st}$ residue (which is Histidine (H)) in SEQ ID NO; 1 is referred to as 7H, meaning that it corresponds to the $7^{th}$ residue in GLP (1-37); and the $31^{st}$ residue (which is Glycine (G)) in SEQ ID NO: 1 is referred to as 37G, meaning corresponds to the $37^{th}$ residue in GLP (1-37).

A functional form of the native GLP-1 peptide is capable of activating the GLP-1 receptor at a level comparable to, or no less than about 20% (or no less than 30%, 40%, 50%, 60%, 70%, 80%, 90%) of, that of the native GLP-1 peptide. Activation of the GLP-1 receptor typically initiates signal transduction pathway resulting in insulinotropic action or other physiological effects as is known in the art. Functional forms of the native GLP-1 peptide can contain one or more substitutions, additions, or deletions relative to SEQ ID NO: 1. Many functional forms of native GLP-1 peptide are known in the art, for example, without limitation, liraglutide, semaglutide, dulaglutide, albiglutide, and those disclosed in WO2000055203A1, WO 98/08871, WO 2006/097537, the disclosure of which is incorporated herein to its entirety.

In certain embodiments, the GLP-1 provided herein comprises an amino acid sequence having at least 70% (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 100%) sequence identity to SEQ ID NO: 1 while retaining substantial biological activity of SEQ ID NO: 1.

In certain embodiments, the GLP-1 comprises no more than 9, 8, 7, 6, 5, 4, 3, or 2 mutations (e.g. addition, deletion, substitution) relative to SEQ ID NO: 1 while retaining substantial biological activity of SEQ ID NO: 1. In certain embodiments, the GLP-1 comprises at least 2, 3, 4, 5, 6, 7, 8, or 9 mutations (e.g. addition, deletion, substitution) relative to SEQ ID NO: 1 while retaining substantial biological activity of SEQ ID NO: 1.

One of ordinary skill in the art will appreciate that various amino acid substitutions, e.g., conservative amino acid substitutions, may be made in the sequence of any of the polypeptide fragment described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

Various substitutions have been introduced to native GLP-1 peptide, and have been shown to be capable of retaining or even improving its biological activities. In certain embodiments, the GLP-1 comprises or consists of one or more mutations at a position selected from the group consisting of: A8, G22, Q23, E27, K26, A30, K34, R36, and H7, and or any combination thereof. For example, it is believed that substitution at A8 is useful to prevent DPP4 enzymatic cleavage at the residue, substitution at G22 is desirable to improve activity and solubility, and substitution at R36 is useful to reduce immunogenicity. Examples of substitutions at these positions include, without limitation, H7IA, H7IPA, A8G, A8S, A8V, A8Aib, A8T, A8I, A8L, G22E, K34R, R36G, as well as the substitutions described in U.S. Pat. No. 8,273,854, which are incorporated herein by its entirety. In certain embodiments, the one or more substitutions comprises a conservative substitution. As used herein, the numbering of the residues in GLP-1 is referred to with reference to the 31 amino-acid sequence set forth in SEQ ID NO: 1, which is also known as GLP-1 (7-37), where residue 7 is Histidine (H7, i.e. the first residue in SEQ ID NO: 1) and residue 37 is Glycine (G37, i.e. the last residue in SEQ ID NO: 1).

In certain embodiments, the GLP-1 comprises a substitution of A8 which is selected from the group consisting of: A8G, A8S, A8V, A8Aib, A8T, A8I and A8L. In certain embodiments, the GLP-1 comprises a substitution of G22E. In certain embodiments, the GLP-1 comprises a substitution of R36G. In certain embodiments, the GLP-1 comprises a substitution of H7 which is H7IA or H7IPA. In certain embodiments, the GLP-1 comprises a substitution of K34 which is K34R.

In certain embodiments, the GLP-1 comprises or consists of one or more substitutions at a position selected from the group consisting of: H7, A8, G22, K34, and R36, or any combination thereof. In certain embodiments, the GLP-1 comprises or consists of one or more substitutions at a position selected from the group consisting of: H7IA, H7IPA, A8G, A8Aib, K34R, G22E, and R36G, or any combination thereof.

In certain embodiments, the GLP-1 comprises or consists of one or more substitutions selected from the group consisting of: A8Aib, K26R, G22E, K34R, and R36G, or any combination thereof.

In certain embodiments, the GLP-1 comprises an amino acid sequence of $X_7X_8$EGTFTSDVSSYLE$X_{22}$ $X_{23}$AA$X_{26}X_{27}$FI $X_{30}$WLV$X_{34}$G$X_{36}$G (SEQ ID NO: 2), wherein: the $X_7$ is H, imidazole-4-acetate (IA), or imidazolepropionic acid (IPA); the $X_8$ is A, G, S, V, Aib, T, I, or L; the $X_{22}$ is G, or E; the $X_{23}$ is Q, C or K; the $X_{26}$ is K, R, or C; the X$_{27}$ is E, K, or C; the X$_{30}$ is A, C or K; the X$_{34}$ is R, K, or C, and the X$_{36}$ is R, or G.

In certain embodiments, X$_7$ is H, X$_8$ is G or Aib, the X$_{22}$ is G or E; the X$_{23}$ is Q, C or K; the X$_{26}$ is K, R or C; the X$_{27}$ is E, K, or C; the X$_{30}$ is A, C or K; the X$_{34}$ is K, R or C, and the X$_{36}$ is R, or G.

In certain embodiments, the GLP-1 comprises an amino acid sequence selected from the group consisting of SEQ ID NOs; 1, 3-44 and 184.

In certain embodiments, the GLP-1 comprises no more than one lysine residue n certain embodiments, the GLP-1 comprises no more than one cysteine residue.

In certain embodiments, the GLP-1 comprises an amino acid sequence selected from the group consisting of:
SEQ ID NO: 1 (WT GLP-1)
SEQ ID NO: 3 (8Aib, 34R, 36G),
SEQ ID NO: 5 (8Aib, 26R, 27K, 34R, 36G),
SEQ ID NO: 7 (8Aib, 26R 34R, 36G),
SEQ ID NO: 8 (8Aib, 22E, 34R, 36G),
SEQ ID NO: 10 (8Aib, 22E, 26R, 27K, 34R, 36G),
SEQ ID NO: 12 (8Aib, 22E, 26R, 34R, 36G),
SEQ ID NO: 13 (8Aib, 34R),
SEQ ID NO: 15 (8Aib, 26R, 27K, 34R),
SEQ ID NO: 17 (8Aib, 26R, 34R),
SEQ ID NO: 18 (8Aib, 22E, 34R),
SEQ ID NO: 20 (8Aib, 22E, 26R, 27K, 34R),
SEQ ID NO: 22 (8Aib, 22E, 26R, 34R),
SEQ ID NO: 23 (8G, 34R, 36G),
SEQ ID NO: 25 (8G, 26R, 27K, 34R, 36G),
SEQ ID NO: 27 (8G, 26R, 34R, 36G),
SEQ ID NO: 28 (8G, 22E, 34R, 36G),
SEQ ID NO: 30 (8G, 22E, 26R, 27K, 34R, 36G),
SEQ ID NO: 32 (8G, 22E, 26R, 34R, 36G),
SEQ ID NO: 33 (8G, 34R),
SEQ ID NO: 35 (8G, 26R, 34R),
SEQ ID NO: 36 (8G, 22E, 34R),
SEQ ID NO: 38 (8G, 22E, 26R, 27K, 34R),
SEQ ID NO: 40 (8G, 22E, 26R, 34R),
SEQ ID NO: 41 (8G, 22E, 36G),
SEQ ID NO: 42 (8G, 36G)
SEQ ID NO: 43 (8G, 22E), and
SEQ ID NO: 44 (8G).

In certain embodiments, the GLP-1 comprises an amino acid sequence selected from the group consisting of:
SEQ ID NO: 3 (8Aib, 34R, 36G),
SEQ ID NO: 4 (8Aib, 26C, 34R, 36G),
SEQ ID NO: 5 (8Aib, 26R, 27K, 34R, 36G),
SEQ ID NO: 6 (8Aib, 27C, 34R, 36G),
SEQ ID NO: 8 (8Aib, 22E, 34R, 36G)
SEQ ID NO: 9 (8Aib, 22E, 26C, 34R, 36G),
SEQ ID NO: 10 (8Aib, 22E, 26R, 27K, 34R, 36G),
SEQ ID NO: 11 (8Aib, 22E, 27C, 34R, 36G),
SEQ ID NO: 13 (8Aib, 34R),
SEQ ID NO: 14 (8Aib, 26C, 34R),
SEQ ID NO: 15 (8Aib, 26R, 27K, 34R),
SEQ ID NO: 16 (8Aib, 27C, 34R),
SEQ ID NO: 18 (8Aib, 22E, 34R),
SEQ ID NO: 19 (8Aib, 22E, 26C, 34R),
SEQ ID NO: 20 (8Aib, 22E, 26R, 27K, 34R),
SEQ ID NO: 21 (8Aib, 22E, 27C, 34R),
SEQ ID NO: 23 (8G, 34R, 36G),
SEQ ID NO: 24 (8G, 26C, 34R, 36G),
SEQ ID NO: 25 (8G, 26R, 27K, 34R, 36G).
SEQ ID NO: 26 (8G, 27C, 34R, 36G),
SEQ ID NO: 28 (8G, 22E, 34R, 36G),
SEQ ID NO: 29 (8G, 22E, 26C, 34R, 36G),
SEQ ID NO: 30 (8G, 22E, 26R, 27K, 34R, 36G),
SEQ ID NO: 31 (8G, 22E, 27C, 34R, 36G),
SEQ ID NO: 33 (8G, 34R)
SEQ ID NO: 34 (8G, 26C, 34R),
SEQ ID NO: 36 (8G, 22E, 34R),
SEQ ID NO: 37 (8G, 22E, 26C, 34R),
SEQ ID NO: 38 (8G, 22E, 26R, 27K, 34R),
SEQ ID NO: 39 (8G, 22E, 27C, 34R) and
SEQ ID NO: 184 (8Aib, 22E, 26C, 34R, 36G)

In certain embodiments, the GLP-1 comprises an amino acid sequence selected from the group consisting of: SEQ ID NOs: 7, 8, 12, 32, and 184.

In certain embodiments, the GLP-1 comprises an amino acid sequence selected from the group consisting of: SEQ ID NOs: 3, 4, 8, 28, 29, and 184.

In certain embodiments, the GLP-1 comprises an amino acid sequence selected from the group consisting of SEQ ID NOs: 3, 8, and 28.

In certain embodiments, the GLP-1 comprises an amino acid sequence selected from the group consisting of SEQ ID NOs: 7, 12, and 32.

In certain embodiments, the GLP-1 comprises an amino acid sequence selected from the group consisting of SEQ ID NOs: 4, 29, and 184.

In certain embodiments, the GLP-1 comprises an amino acid sequence selected from the group consisting of SEQ ID NOs: 7 and 32.

Peptide Linker

In the polypeptide conjugate, the GLP-1 receptor agonist is attached to the N-terminus of the peptide linker. The GLP-1 receptor agonist can be attached to the peptide linker via a direct linkage, such as for example, a covalent bond such as a peptide bond.

The peptide linker can be made up of amino acid residues linked together by peptide bonds. The peptide linker can further comprise one or more non-natural amino acids.

In certain embodiments, the peptide linker has a length of at least 10 amino acid residues (e.g. at least 15, 20, 24, 40, 50, 60, 70, or 80 amino acid resides). In certain embodiments, the polypeptide linker has a length of from 10 to 120, 15 to 120, 20 to 120, 25 to 120, 30 to 120, 31 to 120, 32 to 120, 33 to 120, 34 to 120, 35 to 120, 36 to 120, 37 to 120, 38 to 120, 39 to 120, 40 to 120, 20 to 80, 30 to 80, 31 to 80, 32 to 80, 33 to 80, 34 to 80, 35 to 80, 36 to 80, 37 to 80, 38 to 80, 39 to 80, or 40 to 80 amino acid residues. In certain embodiments, the polypeptide linker has a length of from 12 to 80, 20 to 60, 30 to 60, 30 to 50, 30 to 40, 40 to 50, 30 to 45, or 35 to 45 amino acid residues.

In certain embodiments, the peptide linker has a length of 12-80 amino acid residues.

Any suitable polypeptide linkers can be used. For example, the polypeptide linker may comprise or consist of amino acid residues selected from the amino acids glycine (G), serine (S), alanine (A), methionine (M), asparagine (N), glutamine (Q), cysteine (C) and lysine (K), In some embodiments, the polypeptide linker can be made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)).

In certain embodiments, the peptide linker consists of amino acid residues selected from the group consisting of G, Q, A, E, P, S and T, except for the CRM residue.

In certain embodiments, the peptide linker comprises or consists of one or more repeats of a repeating sequence, except for the CRM residue. In certain embodiments, the peptide linker comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 repeats of a repeating sequence, or within any numerical range defined by any two numbers listed above.

In certain embodiments, the repeating sequence comprises or consists of no more than 4, 5 or 6 types of amino acid residues selected from the group consisting of: G, Q, A, E, P, T and S. In certain embodiments, the repeating sequence comprises or consists of no more than 4, 5 or 6 types of amino acid residues selected from the group consisting of: G, Q, A, E, P, and S. In certain embodiments, the repeating sequence comprises Q. In certain embodiments, the repeating sequence consists of Q and no more than 3, 4 or 5 types of amino acid residues selected from the group consisting of: G, A, E, P, and S.

In certain embodiments, the repeating sequence consists of G, Q, A, E, and P. In certain embodiments, the repeating sequence consists of G, Q, A, and P.

In certain embodiments, the repeating sequence comprises or consists of a sequence selected from the group consisting of: SEQ ID NOs: 45-75, and GS.

In certain embodiments, the polypeptide linker comprises or consists of more than one repeating sequence. For example, the polypeptide linker comprises or consists of 2, 3, or 4 different repeating sequences. In certain embodiments, the polypeptide linker comprises or consists of sequential or tandem repeats of the different repeating sequences.

In certain embodiments, the polypeptide linker comprises or consists of (Repeat1)r(Repeat2)s(Repeat3)x(Repeat4)y, wherein:
Repeat1, Repeat2, Repeat3 and Repeat4 are linked via a peptide bond or via one or more amino acid residues;
Repeat1, Repeat2, Repeat3 and Repeat4 independently, comprise or consist of a sequence selected from the group consisting of: SEQ ID NOs: 45-75 and GS, and
r, s, x and y are independently an integer selected from 0 to 30 (e.g. from 0-29, 0-28, 0-27, 0-26, 0-25, 0-24, 0-23, 0-22, 0-21, 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, or 0-1), provided that r, s, x and y are not 0 at the same time.

In certain embodiments, x and y are 0, r, and s are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 and Repeat2 are a combination selected from the group consisting of:
a) Repeat1 comprises or consists of a sequence of SEQ ID NO: 45, Repeat2 comprises or consists of a sequence of SEQ ID NO: 48;
b) Repeat1 comprises or consists of a sequence of SEQ ID NO: 47, Repeat2 comprises or consists of a sequence of SEQ ID NO: 48;
c) Repeat1 comprises or consists of a sequence of SEQ ID NO: 48, Repeat2 comprises or consists of a sequence of SEQ ID NO: 47;
d) Repeat1 comprises or consists of a sequence of SEQ ID NO: 48, Repeat2 comprises or consists of a sequence of SEQ ID NO: 45;
e) Repeat1 comprises or consists of a sequence of SEQ ID NO: 49, Repeat2 comprises or consists of a sequence of SEQ ID NO: 48;
f) Repeat1 comprises or consists of a sequence of SEQ ID NO: 70, Repeat2 comprises or consists of a sequence of SEQ ID NO: 48;
g) Repeat1 comprises or consists of a sequence of SEQ ID NO; 48, Repeat2 comprises or consists of a sequence of SEQ ID NO; 68 and
h) Repeat1 comprises or consists of a sequence of SEQ ID NO: 70, Repeat2 comprises or consists of a sequence of SEQ ID NO: 47.

In certain embodiments, r, x and y are 0, s is an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 comprises or consists of a sequence of SEQ ID NO: 45.

In certain embodiments, y is 0, r, s and x are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 Repeat2 and Repeat3 are a combination selected from the group consisting of:
a) Repeat1 comprises or consists of a sequence of SEQ ID NO: 48, Repeat2 comprises or consists of a sequence of SEQ ID NO: 49; and Repeat3 comprises or consists of a sequence of SEQ ID NO: 48;
b) Repeat1 comprises or consists of a sequence of SEQ ID NO: 48, Repeat2 comprises or consists of a sequence of SEQ ID NO: 47; and Repeat3 comprises or consists of a sequence of SEQ ID NO: 48;
c) Repeat1 comprises or consists of a sequence of SEQ ID NO: 70, Repeat2 comprises or consists of a sequence of SEQ ID NO: 47; Repeat3 comprises or consists of a sequence of SEQ ID NO: 48;
d) Repeat1 comprises or consists of a sequence of SEQ ID NO: 70, Repeat2 comprises or consists of a sequence of SEQ ID NO: 48; Repeat3 comprises or consists of a sequence of SEQ ID NO: 47,
e) Repeat1 comprises or consists of a sequence of SEQ ID NO: 45, Repeat2 comprises or consists of a sequence of SEQ ID NO; 58; Repeat3 comprises or consists of a sequence of SEQ ID NO: 48,
f) Repeat1 comprises or consists of a sequence of SEQ ID NO: 48, Repeat2 comprises or consists of a sequence of SEQ ID NO: 68; Repeat3 comprises or consists of a sequence of SEQ ID NO: 45,
g) Repeat1 comprises or consists of a sequence of SEQ ID NO: 48, Repeat2 comprises or consists of a sequence of SEQ ID NO: 45; Repeat3 comprises or consists of a sequence of SEQ ID NO: 48, and
h) Repeat1 comprises or consists of a sequence of SEQ ID NO: 48, Repeat2 comprises or consists of a sequence of SEQ ID NO: 45; Repeat3 comprises or consists of a sequence of SEQ ID NO: 68.

In certain embodiments, r, s, x and y are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 Repeat2, Repeat 3 and Repeat 4 are a combination selected from the group consisting of:
a) Repeat1 comprises or consists of a sequence of SEQ ID NO: 48, Repeat2 comprises or consists of a sequence of SEQ ID NO: 50; Repeat3 comprises or consists of a sequence of SEQ ID NO: 47, and Repeat4 comprises or consists of a sequence of SEQ ID NO: 48,
b) Repeat1 comprises or consists of a sequence of SEQ ID NO: 45, Repeat2 comprises or consists of a sequence of SEQ ID NO: 68; Repeat3 comprises or consists of a sequence of SEQ ID NO: 45, and Repeat4 comprises or consists of a sequence of SEQ ID NO: 48, c) Repeat1 comprises or consists of a sequence of SEQ ID NO; 48, Repeat2 comprises or consists of a sequence of SEQ ID NO: 68; Repeat3 comprises or consists of a sequence of SEQ ID NO: 45, and Repeat4 comprises or consists of a sequence of SEQ ID NO: 48, d) Repeat1 comprises or consists of a sequence of SEQ ID NO: 48, Repeat2 comprises or consists of a sequence of SEQ ID NO: 58; Repeat3 comprises or consists of a sequence of SEQ ID NO: 48, and Repeat4 comprises or consists of a sequence of SEQ ID NO: 45, and e) Repeat1 comprises or consists of a sequence of SEQ ID NO: 48, Repeat2 comprises or consists of a sequence of SEQ ID NO: 45; Repeat3 comprises or consists of a sequence of SEQ ID NO; 69, and Repeat4 comprises or consists of a sequence of SEQ ID NO: 68.

In certain embodiments, the peptide linker comprises an amino acid sequence selected from the group consisting of SEQ ID NOs: 76-89, except that one residue is substituted by the CRM residue.

In certain embodiments, the peptide linker comprises an amino acid sequence selected from the group consisting of SEQ ID NOs: 90-117, 175, and 176.

CRM Residue

In certain embodiments, the polypeptide conjugate can be mono-conjugated with a CRM. In certain embodiments, the first CRM residue is lysine residue, and the polypeptide conjugate comprises only one lysine residue. In such embodiments, the peptide linker comprises only one lysine residue, and the GLP-1 receptor agonist comprises no lysine residue.

In certain embodiments, the single biologically active peptide in the polypeptide conjugate comprises GLP-1, and the naturally occurring residue found in the native GLP-1 sequence, namely K26 and K34, can be substituted to non-lysine residues. In certain embodiments, the GLP-1 comprises substitution of K26, which is selected from the group consisting of K26R, K26Q, K26A, K26G, K26H, K26S, and K26T. In certain embodiments, the GLP-1 comprises, or further comprises, substitution of K34 which is selected from the group consisting of K34R, K34Q, K34A, K34G, K34H, K34S, and K34T. In certain embodiments, the substitution of K26 is selected from K26R and K26O, and/or the substitution at K34 is selected from K34R and K34O. Throughout the specification, when K residue is present in GLP-1, the position of K is identified in reference to the amino acid sequence of GLP-1 (1-37). For example, K26 indicates that the 26$^{th}$ position in reference to the amino acid sequence of GLP-1 (1-37) (which corresponds to the 20th position in reference to the amino acid sequence of GLP-1 (7-37), i.e. SEQ ID NO: 1) is K. Similarly, K34 indicates that the 34th position in reference to the amino acid sequence of GLP-1 (1-37) (which corresponds to the 28th position in reference to the amino acid sequence of GLP-1 (7-37), i.e. SEQ ID NO: 1) is K.

In certain embodiments, the GLP-1 may further comprises one or more additional mutations at a position selected from the group consisting of: A8, G22, E27, R36, and H7, and or any combination thereof. In certain embodiment, the GLP-1 comprises K26R and K34R. In certain embodiments, the GLP-1 comprises an amino acid sequence selected from the group consisting of:

SEQ ID NO: 7 (8Aib, 26R, 34R, 36G),
SEQ ID NO: 12 (8Aib, 22E, 26R, 34R, 36G),
SEQ ID NO: 17 (8Aib, 26R, 34R),
SEQ ID NO: 22 (8Aib, 22E, 26R, 34R),
SEQ ID NO: 27 (8G, 26R, 34R, 36G),
SEQ ID NO: 32 (8G, 22E, 26R, 34R, 36G),
SEQ ID NO: 35 (8G, 26R, 34R), and
SEQ ID NO: 40 (8G, 22E, 26R, 34R).

In certain embodiments, the first CRM residue is cysteine residue, and the polypeptide conjugate comprises only one cysteine residue. In such embodiments, the peptide linker comprises only one cysteine residue, and the GLP-1 receptor agonist comprises no cysteine residue. In certain embodiments, the single biologically active peptide polypeptide in the polypeptide conjugate comprises GLP-1, Native GLP-1 does not contain any cysteine residue, and therefore any GLP-1 derivative (including those provided herein) may be used as long as it does not contain a cysteine residue.

In certain embodiments, the first CRM residue is a non natural amino acid residue, and the polypeptide conjugate comprises only one non-natural amino acid residue as the CRM residue. Non-natural amino acid can contain a variety of functional groups or reactive groups, which can provide for additional functions and/or reactivity. Particular non-natural amino acids that are beneficial for purpose of conjugating moieties to the fusion polypeptides of the present disclosure include those with a side chain having azide, alkyne, alkene, cycloalkyne or halide.

Where the first CRM residue is cysteine or non-natural amino acid residue, the GLP-1 can comprise an amino acid sequence selected from the group consisting of: SEQ ID NOs: 1, 3, 5, 7, 8, 10, 12, 13, 15, 17, 18, 20, 22, 23, 25, 27, 28, 30, 32, 33, 35, 36, 38 and 40-44.

In certain embodiments, the polypeptide conjugate further comprises a second CRM residue. In certain embodiments, the second CRM residue is in the peptide linker. In such embodiments, the second CRM residues can be at any suitable distance from the first CRM residue, as long as both CRM residues can be properly conjugated. In certain embodiments, the second CRM residue is in the GLP-1 receptor agonist, for example, GLP-1. In certain embodiments, the second CRM residue is a naturally occurring residue found in the native GLP-1 sequence, or an introduced residue, for example, by substitution of a naturally occurring residue, or by insertion of a new residue.

In certain embodiments, the first and the second CRM residues are both lysine residues, and the polypeptide conjugate comprises only two lysine residues. In certain embodiments, the second lysine residue is in the GLP-1, and is selected from the group consisting of K23, K26, K27, K30, and K34. In certain embodiments, the second CRM residue is a naturally occurring residue found in the native GLP-1 sequence, for example, K26 or K34. In certain embodiments, the second CRM residue is an introduced residue. The CRM residue can be introduced into GLP-1 sequence at any suitable position, for example by substitution, as long as such substitution does not substantially diminish the GLP-1R agonist activity of the GLP-1. The second CRM residue can be introduced, for example, by substitution of Q23K, E27K, or A30K. In certain embodiments, all lysine residue(s) other than the CRM residue(s) in the GLP-1 are substituted to a non-lysine residue, so that the polypeptide conjugate comprises no additional lysine residue except for the CRM residues. For example, if K26 is the second CRM residue, then K34 is substituted to a non-lysine residue, or vice versa. Non-lysine residue can be selected by a skilled person in the art, and examples include Arginine (R), Glutamine (Q), Alanine (A), Glycine (G), Histidine (H), Serine (S), or Threonine (T).

Where both the first and the second CRM residues are lysine residue, the GLP-1 can comprise an amino acid sequence selected from the group consisting of: SEQ ID NOs: 3, 5, 8, 10, 13, 15, 18, 20, 23, 25, 28, 30, 33, 36 and 38.

In certain embodiments, the first and the second CRM residues are both cysteine residues, and the polypeptide conjugate comprises only two cysteine residues. In certain embodiments, the second cysteine residue is in the GLP-1. In certain embodiments, the second cysteine residue is in the peptide linker.

In certain embodiments, the first and the second CRM residues are both non-natural amino acid residues, and the polypeptide conjugate comprises only two non-natural amino acid residues as the CRM residues.

In certain embodiments, the cysteine residue or the non-natural amino acid residue in the GLP-1 is introduced by a substitution at the position selected from the group consisting of: Q23, K26, E27, A30, and K34, relative to SEQ ID NO: 1. In certain embodiments, the cysteine residue or the NNAA in the GLP-1 is introduced by a substitution at the position of K26 or E27, relative to SEQ ID NO: 1. In certain embodiments, the second CRM residue in the GLP-1 is cysteine and is introduced by a substitution at a position selected from the group consisting of: Q23C, K26C, E27C, A30C and K34C.

Where both the first and the second CRM residues are cysteine residue, the GLP-1 can comprise an amino acid sequence selected from the group consisting of: SEQ ID NOs: 4, 6, 9, 11, 14, 16, 19, 21, 24, 26, 29, 31, 34, 37, 39, and 184.

CRM

In certain embodiments, the CRM comprises a plasma protein-binding moiety, a polymer, Fc, human serum albumin (HSA) and functional fragments thereof, Xten sequence, or PAS sequence. In certain embodiments, the Xten sequence is an extended recombinant polypeptide sequence with an amino acid sequence described in WO2007103515, WO2009023270, WO2010091122, WO2011123813, WO2013130683, WO2017146979, WO2011084808, WO2013040093, WO2013122617, WO2014011819, WO2013184216, WO2014164568, WO2015023891, WO2016077505 and WO2017040344, disclosures of which have been incorporated by their entirety. In certain embodiments, the term "PAS", which can also be used interchangeable with the term "APS", refers to an amino acid repeats consisting of Ala, Ser, and Pro residues, as described in U.S. Pat. No. 8,563,521B2, disclosure of which has been incorporated by its entirety.

In certain embodiments, the CRM comprises an albumin-binding moiety. The term "albumin-binding moiety" refers to any functional moiety that is capable of binding albumin (e.g. human serum albumin) or any functional fragment thereof with sufficient specificity, preferably non-covalently. The albumin-binding moiety attached to a therapeutic fusion polypeptide, polypeptide, or polypeptide complex typically has an affinity below 10 μM to human serum albumin and preferably below 1 μM. The albumin-binding moiety can include, without limitation, an albumin-binding domain, an albumin-binding sequences from synthetic peptides, and an albumin-binding chemical moiety. For example, the albumin-binding moiety is selected from an albumin-binding domain from streptococcal protein G, an albumin-binding domain from *Peptostreptococcus magnus* protein PAB, an albumin-binding peptide having the core sequence DICL-PRWGCLW (SEQ ID NO: 173), A number of small peptides which are albumin binding moieties have been described in J. Biol Chem. 277, 38 (2002) 35035-35043. For another example, the albumin-binding moiety is selected from linear and branched lipohophillic moieties containing 4-40 carbon atoms, compounds with a cyclopentanophenanthrene skeleton etc. For example, the albumin-binding moiety is a group of the formula $CH_3$ $(CH_2)_v CO-NHCH(COOH)$ $(CH_2)_2 CO-$, wherein v is an integer of from 10 to 24.

In certain embodiments, the albumin-binding moiety comprises a structure of: *-A-B-C-D-E, wherein A, B, C, D and E are interconnected via amide bonds, and the * end of A is connected to a reactive group of the conjugatable residue on the polypeptide complex, and wherein:

A is selected from a bond,

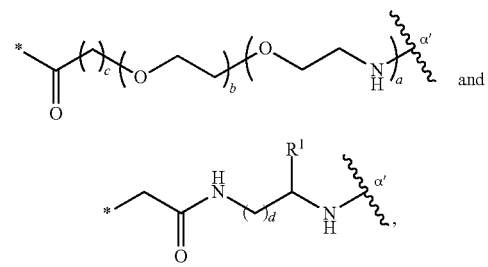 and a, b, c and d are independently an integer from 0 to 4, $R^1$ is hydrogen or $-COOH$;

B is selected from a bond,

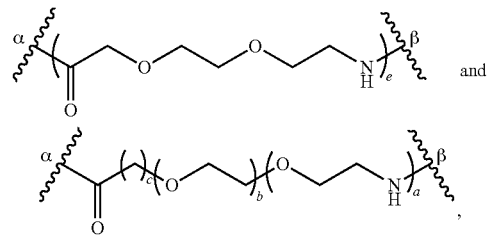

e is an integer from 1 to 4, wherein position α is linked to position α',

C is a bond

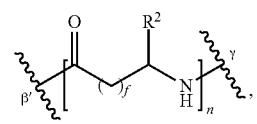, $R^2$ is $-CH_2SO_3H$ or $-COOH$, f is an integer from 1 to 4, n is an integer from 1 to 25, wherein when B is not bond, then position β' is linked to position β, or when B is bond, then position β' is linked to position α';

D is selected from a bond,

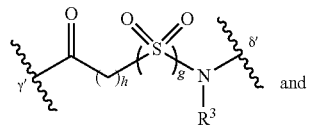 and

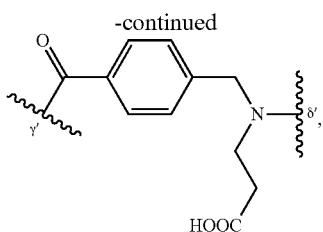

g and h are independently 0 or 1, and $R^3$ is H or —$CH_2COOH$, wherein:

when B is not a bond and C is a bond; then position γ' is linked to position β;

when C is not a bond, then position γ' is linked to position γ; and when B is a bond and C is a bond, then position γ' is linked to position α';

E is an acidic group having a formula:

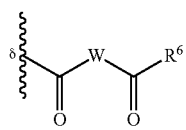

(I)

wherein W represents —$(CR^4R^5)_I$—, $R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, $R^6$ is selected from hydroxyl or $NR^7R^8$;

$R^7$ and $R^8$ are independently selected from the group consisting of hydrogen, alkyl, hydroxyl, and

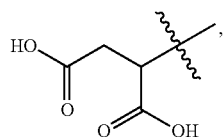

and

I is an integer from 10 to 20 and wherein:

when D is not a bond, then position δ is linked to position δ', when C is not a bond and D is a bond, then position δ is linked to position γ, when B is not a bond, C is a bond and D is a bond, then position δ is linked to position β, when A is not a bond, and all of B, C, and D are bond, then position δ is linked to position α', or a pharmaceutically acceptable salt thereof.

In certain embodiments, the CRM is conjugated to a lysine residue, optionally the lysine residue is in the peptide linker or in the GLP-1.

In certain embodiments, A is a bond.

In certain embodiments, A is a bond, and B is a bond or

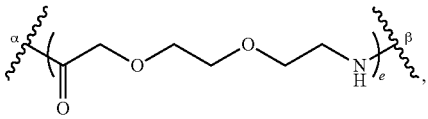

wherein e is 1, 2 or 3.

In certain embodiments, A is a bond, B is

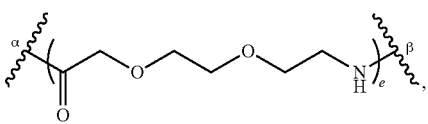

and C is

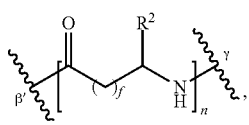

wherein position β' is linked to position β, wherein e is 1, 2 or 3, f is 1, 2, or 3, and n is 1 or 2. In certain embodiments, D is a bond, and E is an acidic group having a formula:

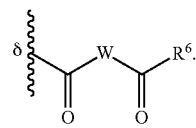

In certain embodiments, $R^2$ is —COOH, and $R^6$ is hydroxyl. In certain embodiments, W represents —$(CR_4R_5)_I$—, $R^4$ and $R^5$ are independently hydrogen, I is an integer from 10 to 20.

In certain embodiments, A is a bond, B is a bond, and C is a bond.

In certain embodiments, A is a bond, B is a bond, and C is

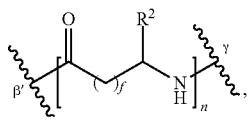

wherein f is 1, 2, or 3, and n is 1 or 2.

In certain embodiments, A is

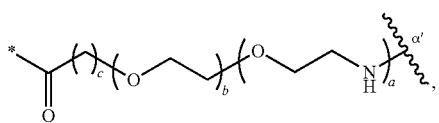

wherein a is 1, 2 or 3, b is 1, 2 or 3, and c is 1 or 2.

In certain embodiments, A is

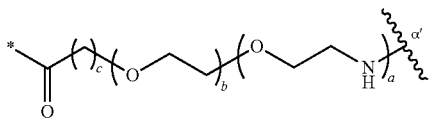

and B is

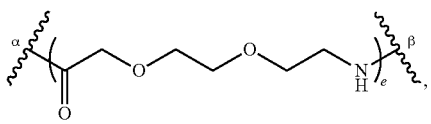

wherein a is 1, 2 or 3, b is 1, 2 or 3, c is 1 or 2, and e is 1, 2 or 3, wherein position α is linked to position α.

In certain embodiments, A is

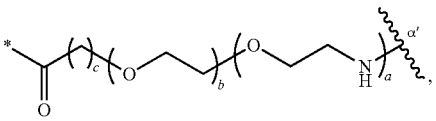

B is

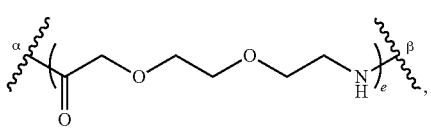

and C is

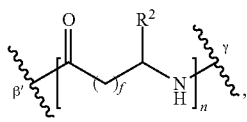

wherein position α is linked to position α' and position β' is linked to position β, wherein a is 1, 2 or 3, b is 1, 2 or 3, c is 1 or 2, e is 1, 2 or 3, f is 1, 2, or 3, and n is 1 or 2.

In certain embodiments, A is

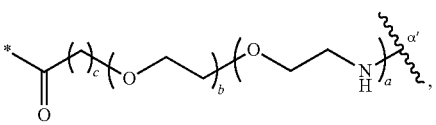

B is

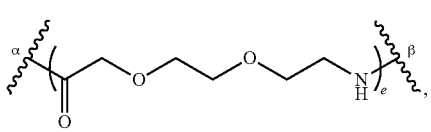

and C is bond, wherein position α is linked to position α', wherein a is 1, 2 or 3, b is 1, 2 or 3, c is 1 or 2, and e is 1, 2 or 3, In certain embodiments, A is

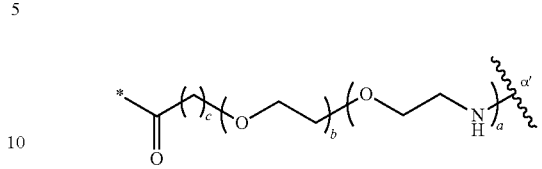

and B is a bond, wherein a is 1, 2 or 3, b is 1, 2 or 3, and c is 1 or 2.

In certain embodiments, A is

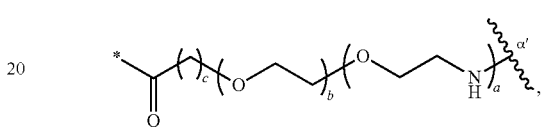

B is a bond, and C is

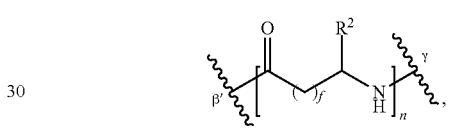

wherein position β' is linked to position α', wherein a is 1, 2 or 3, b is 1, 2 or 3, c is 1 or 2, f is 1, 2, or 3, and n is 1 or 2.

In certain embodiments, A is

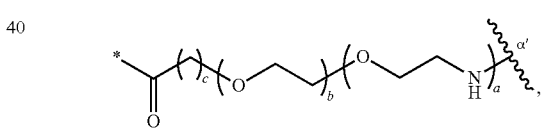

B is a bond, and C is a bond, wherein a is 1, 2 or 3, b is 1, 2 or 3, and c is 1 or 2.

In certain embodiments, D is a bond.

In certain embodiments, A is

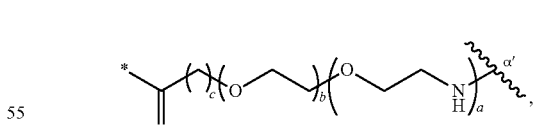

B is

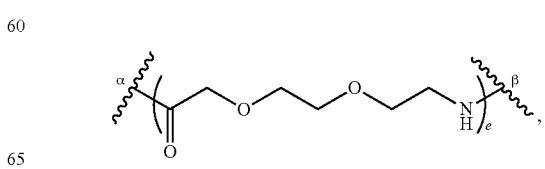

C is

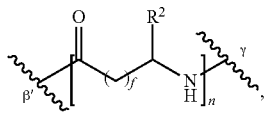

and D is a bond, wherein position α is linked to position α' and position β' is linked to position β, wherein a is 1, 2 or 3, b is 1, 2 or 3, c is 1 or 2, e is 1, 2 or 3, f is 1, 2, or 3, and n is 1 or 2.

In certain embodiments, D is

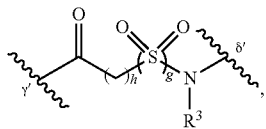

wherein g is 0 or 1, and h is 0 or 1.

In certain embodiments, A is

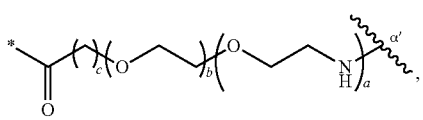

B is

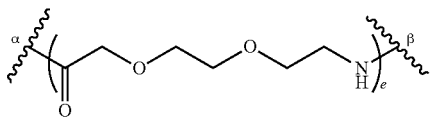

or a bond, C is a bond, and D is

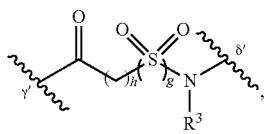

wherein when B is not bond, then position α is linked to position α' and position γ' is linked to position or when B is bond, then position γ' is linked to position α', wherein a is 1, 2 or 3, b is 1, 2 or 3, c is 1 or 2, e is 1, 2 or 3, g is 0 or 1, and h is 0 or 1, In certain embodiments, D is

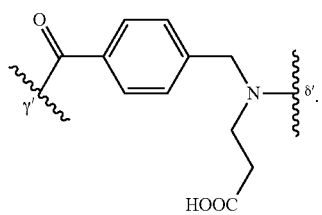 [SMILES: *C(=O)c1ccc(CN(*)CCC(=O)O)cc1]

In certain embodiments, A is

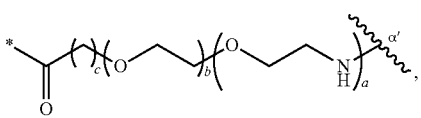

B is

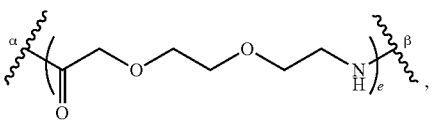

C is a bond or

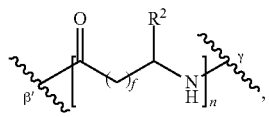

and D is

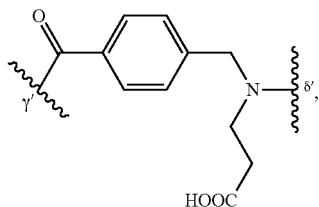 [SMILES: *C(=O)c1ccc(CN(*)CCC(=O)O)cc1]

wherein position α is linked to position α', wherein when C is a bond, then position γ' is linked to position β, or when C is not a bond, position β is linked to position β and position γ' is linked to position γ, wherein a is 1, 2 or 3, b is 1, 2 or 3, c is 1 or 2, e is 1, 2 or 3, f is 1, 2, or 3, and n is 1 or 2.

In such embodiments, the CRM comprises the structure of below formula (also referred to as —HOOC—(CH2)16-CO-gGlu-2XADO, where 2XADO means two consecutive ADO moieties, and ADO is short for 8-amino-3,6-dioxaoctanoic acid):

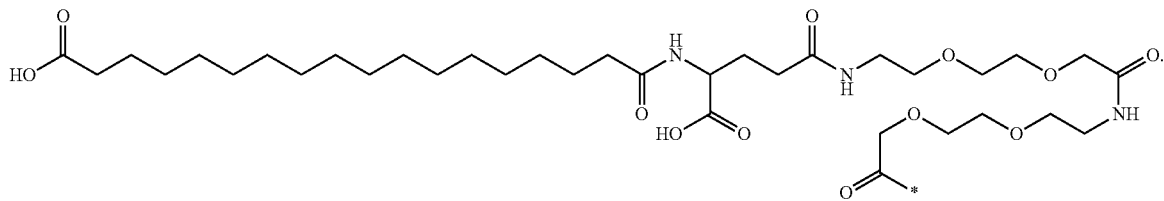 [SMILES: *C(=O)COCCOCCNC(=O)COCCOCCNC(=O)CCC(NC(=O)CCCCCCCCCCCCCCCCC(=O)O)C(=O)O]

In certain embodiments, the CRM is conjugated to a cysteine residue, optionally the cysteine residue is in the peptide linker or in the GLP-1, In certain embodiments, A is

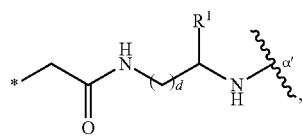

and B is

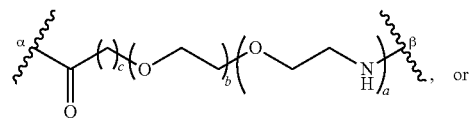

wherein position α is linked to position α'.

In certain embodiments, A is

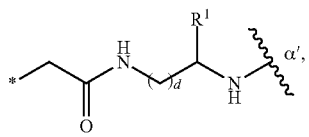

B is

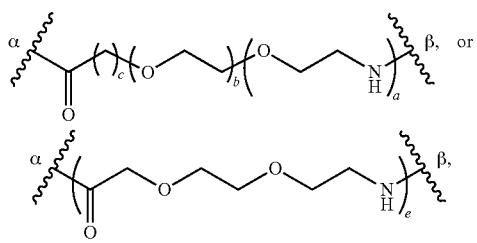

and C is

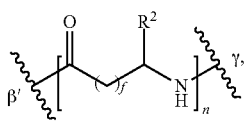

wherein position α is linked to position α' and position β' is linked to position β, wherein a is 1, 2 or 3, b is 1, 2 or 3, c is 1 or 2, d is 1, 2, or 3, f is 1, 2, or 3, and n is 1 or 2. In certain embodiments, D is a bond, and E is an acidic group having a formula:

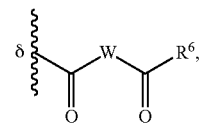

wherein position δ is linked to position γ. In certain embodiments, R2 is —COOH, and R6 is hydroxyl. In certain embodiments, W represents —(CR4R5)l—, R4 and R5 are independently hydrogen, l is an integer from 10 to 20.

In certain embodiments, A is

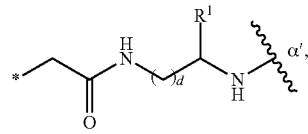

B is

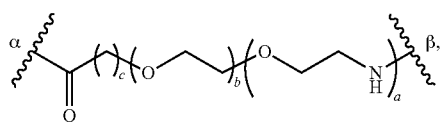

C is

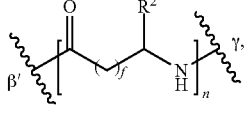

and D is a bond, wherein position α is linked to position α' and position β' is linked to position β, wherein a is 1, 2 or 3, b is 1, 2 or 3, c is 1 or 2, d is 1, 2, or 3, f is 1, 2, or 3, and n is 1 or 2.

In certain embodiments, A is

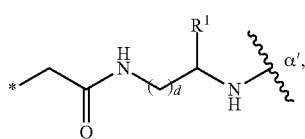

and B is

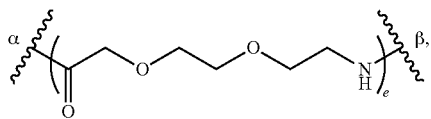

wherein position α is linked to position α', wherein d is 1, 2, or 3, and e is 1, 2 or 3.

In certain embodiments, A is

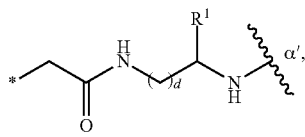

B is

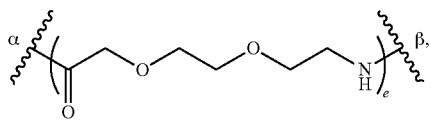

and C is a bond, wherein position α is linked to position α', wherein d is 1, 2, or 3, and e is 1, 2 or 3.

In certain embodiments, A is

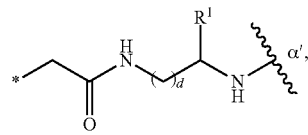

B is

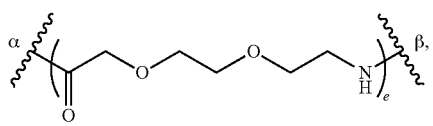

C is a bond, and D is

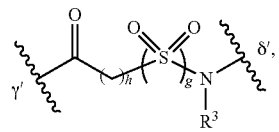

wherein position α is linked to position α' and position γ' is linked to position β, wherein d is 1, 2, or 3, e is 1, 2 or 3, g is 0 or 1, and h is 0 or 1.

In such embodiments, the CRM comprises the structure of below formula (also referred to as HOOC—(CH2)16-CO-gGlu-2XADO-EDA-CO—CH2) or HOOC—(CH2)20-CO-gGlu-2XADO-EDA-CO—CH2).

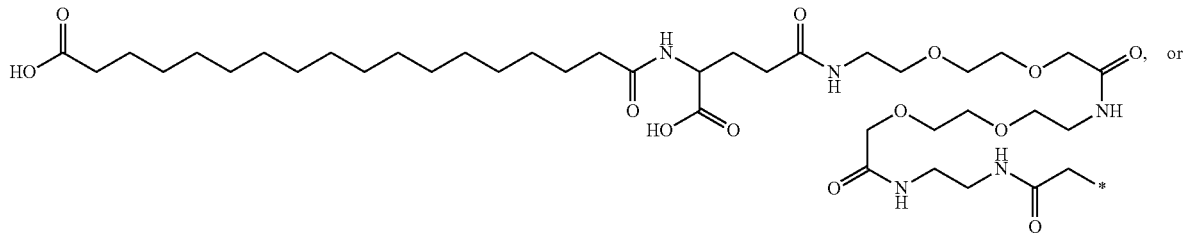

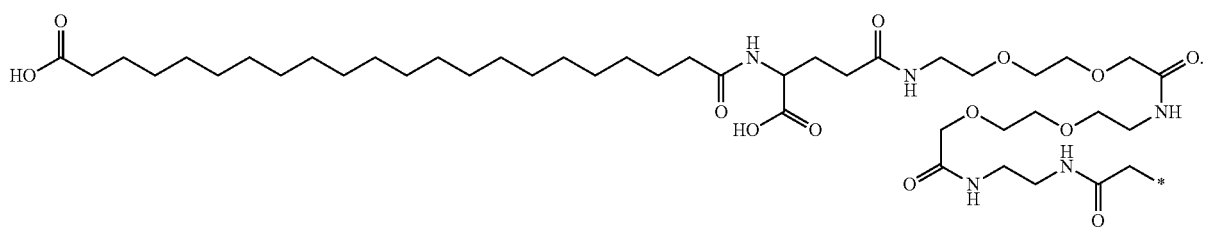

Conjugates

In certain embodiments, the polypeptide conjugate comprises or consists of an amino acid sequence selected from the group consisting of SEQ ID NOs: 118-174, 177-183 and 185-190.

In certain embodiments, the polypeptide conjugate provided herein comprises an amino acid sequence selected from a group consisting of: SEQ ID NOs: 119, 126-128, 136-139, 147-150, 158-161, 169-174, 177-183, and 185-190, and a CRM attached to the lysine or cysteine residue. In certain embodiments, the CRM comprises the structure of —HOOC—(CH2)16-CO-gGlu-2XADO (for lysine conjugation) or HOOC—(CH2)16-CO-gGlu-2XADO-EDA-CO—CH2 (for cysteine conjugation).

In certain embodiments, the polypeptide conjugate provided herein comprises an amino acid sequence selected from a group consisting of: SEQ ID NOs: 118, 120-125, 129-135, 140-146, 151-157, 162-168, 173, 174, and 177-183 and two CRMs attached respectively to the two lysine residues, or to the two cysteine residues. In certain embodiments, the CRM comprises the structure of —HOOC—(CH2)16-CO-gGlu-2XADO (for lysine conjugation) or HOOC—(CH2)16-CO-gGlu-2XADO-EDA-CO—CH2 (for cysteine conjugation).

In certain embodiments, the polypeptide conjugate provided herein comprises an amino acid sequence selected from a group consisting of SEQ ID NOs: 118, 120, 121, 122, 123, 124, 125, 129, 130, 131, 132, 133, 134, 135, 140, 141, 142, 143, 144, 145, 146, 173, 174, and 177-183, and two CRMs attached respectively to the two lysine residues. In certain embodiments, the CRM comprises the structure of —HOOC—(CH2)16-CO-gGlu-2XADO.

In certain embodiments, the polypeptide conjugate provided herein comprises an amino acid sequence selected from a group consisting of SEQ ID NOs: 119, 126, 127, 128, 136, 137, 138, 139, 147, 148, 149, and 150, and a CRM attached to the lysine residue. In certain embodiments, the CRM comprises the structure of —HOOC—(CH2)16-CO-gGlu-2XADO.

In certain embodiments, the polypeptide conjugate provided herein comprises an amino acid sequence selected from a group consisting of SEQ ID NOs: 151, 152, 153, 154, 155, 156, 157, 162, 163, 164, 165, 166, 167, 168, and 177-183 and two CRMs attached respectively to the two cysteine residues. In certain embodiments, the CRM comprises the structure of HOOC—(CH2)16-CO-gGlu-2XADO-EDA-CO—CH2.

In certain embodiments, the polypeptide conjugate provided herein comprises an amino acid sequence selected from a group consisting of SEQ ID NOs: 158, 159, 160, 161, 169, 170, 171, 172, and 185-190, and a CRM attached to the cysteine residue. In certain embodiments, the CRM comprises the structure of HOOC—(CH2)16-CO-gGlu-2XADO-EDA-CO—CH2.

In certain embodiments, the CRM is conjugated to a non-natural amino acid residue in the fusion polypeptide. In certain embodiments, the CRM is conjugated to a non-natural amino acid residue in the polypeptide.

Table 1 below shows the detailed information of each of the exemplary polypeptide conjugates, including SEQ ID NOs of the polypeptide portion, the GLP-1, and the peptide linker, and the CRM residue. Mutations in the GLP-1, as well as the repeating sequences and number of repeats in the peptide linker sequences are also shown.

TABLE 1

Exemplary polypeptide conjugate sequences

| Molecule Code (MLC) | Mutations in GLP-1** (SEQ ID NO of the GLP-1) | Repeating sequences and number of repeats (SEQ ID NO of the peptide linker) | CRM residue(s) (SEQ ID NO of the polypeptide portion) | CRM |
|---|---|---|---|---|
| 001 | 8Aib,34R,36G (SEQ ID NO: 3) | (GAQP)9(GQKP) (SEQ ID NO: 90) | 26K, 76K (SEQ ID NO: 118) | Moiety A$^{\&}$ |
| 002 | 8Aib,26R, 34R,36G (SEQ ID NO: 7) | (GAQP)9(GQKP) (SEQ ID NO: 90) | 76K (SEQ ID NO: 119) | Moiety A$^{\&}$ |
| 003 | 8Aib,34R,36G (SEQ ID NO: 3) | (GAQP)19(GQKP) (SEQ ID NO: 91) | 26K, 116K (SEQ ID NO: 120) | Moiety A$^{\&}$ |
| 004 | 8Aib,34R,36G (SEQ ID NO: 3) | (GAQP)14(GQKP) (SEQ ID NO: 92) | 26K, 96K (SEQ ID NO: 121) | Moiety A$^{\&}$ |
| 005 | 8Aib,34R,36G (SEQ ID NO: 3) | (GAQP)11(GQKP) (SEQ ID NO: 93) | 26K, 84K (SEQ ID NO: 122) | Moiety A$^{\&}$ |
| 006 | 8Aib,34R,36G (SEQ ID NO: 3) | (GAQP)7(GQKP) (SEQ ID NO: 94) | 26K, 68K (SEQ ID NO: 123) | Moiety A$^{\&}$ |
| 007 | 8Aib,34R,36G (SEQ ID NO: 3) | (GAQP)5(GQKP) (SEQ ID NO: 95) | 6K, 60K (SEQ ID NO: 124) | Moiety A$^{\&}$ |
| 008 | 8Aib,34R,36G (SEQ ID NO: 3) | (GAQP)2(GQKP) (SEQ ID NO: 96) | 26K, 48K (SEQ ID NO: 125) | Moiety A$^{\&}$ |
| 009 | 8Aib,26R,34R,36G (SEQ ID NO: 7) | (GAQP)7(GQKP) (SEQ ID NO: 94) | 68K (SEQ ID NO: 126) | Moiety A$^{\&}$ |
| 010 | 8Aib,26R,34R,36G (SEQ ID NO: 7) | (GAQP)5(GQKP) (SEQ ID NO: 95) | 60K (SEQ ID NO: 127) | Moiety A$^{\&}$ |
| 011 | 8Aib,26R,34R,36G (SEQ ID NO: 7) | (GAQP)2(GQKP) (SEQ ID NO: 96) | 48K (SEQ ID NO: 128) | Moiety A$^{\&}$ |
| 012 | 8Aib,22E,34R,36G (SEQ ID NO: 8) | (GAQP)9(GQKP) (SEQ ID NO: 90) | 26K, 76K (SEQ ID NO: 129) | Moiety A$^{\&}$ |
| 013 | 8Aib,22E,34R,36G (SEQ ID NO: 8) | (GAQP)19(GQKP) (SEQ ID NO: 91) | 26K, 116K (SEQ ID NO: 130) | Moiety A$^{\&}$ |
| 014 | 8Aib,22E,34R,36G (SEQ ID NO: 8) | (GAQP)14(GQKP) (SEQ ID NO: 92) | 26K, 96K (SEQ ID NO: 131) | Moiety A$^{\&}$ |
| 015 | 8Aib,22E,34R,36G (SEQ ID NO: 8) | (GAQP)11(GQKP) (SEQ ID NO: 93) | 26K, 84K (SEQ ID NO: 132) | Moiety A$^{\&}$ |
| 016 | 8Aib,22E,34R,36G (SEQ ID NO: 8) | (GAQP)7(GQKP) (SEQ ID NO: 94) | 26K, 68K (SEQ ID NO: 133) | Moiety A$^{\&}$ |

TABLE 1-continued

Exemplary polypeptide conjugate sequences

| Molecule Code (MLC) | Mutations in GLP-1** (SEQ ID NO of the GLP-1) | Repeating sequences and number of repeats (SEQ ID NO of the peptide linker) | CRM residue(s) (SEQ ID NO of the polypeptide portion) | CRM |
|---|---|---|---|---|
| 017 | 8Aib,22E,34R,36G (SEQ ID NO: 8) | (GAQP)5(GQKP) (SEQ ID NO: 95) | 26K, 60K (SEQ ID NO: 134) | Moiety A<sup>&</sup> |
| 018 | 8Aib,22E,34R,36G (SEQ ID NO: 8) | (GAQP)2(GQKP) (SEQ ID NO: 96) | 26K, 48K (SEQ ID NO: 135) | Moiety A<sup>&</sup> |
| 019 | 8Aib,22E,26R 34R,36G (SEQ ID NO: 12) | (GAQP)9(GQKP) (SEQ ID NO: 90) | 76K (SEQ ID NO: 136) | Moiety A<sup>&</sup> |
| 020 | 8Aib,22E,26R,34R,36G (SEQ ID NO: 12) | (GAQP)7(GQKP) (SEQ ID NO: 94) | 68K (SEQ ID NO: 137) | Moiety A<sup>&</sup> |
| 021 | 8Aib,22E,26R,34R,36G (SEQ ID NO: 12) | (GAQP)5(GQKP) (SEQ ID NO: 95) | 60K (SEQ ID NO: 138) | Moiety A<sup>&</sup> |
| 022 | 8Aib,22E,26R,34R,36G (SEQ ID NO: 12) | (GAQP)2(GQKP) (SEQ ID NO: 96) | 48K (SEQ ID NO: 139) | Moiety A<sup>&</sup> |
| 023 | 8G,22E,34R,36G (SEQ ID NO: 28) | (GAQP)9(GQKP) (SEQ ID NO: 90) | 26K, 76K (SEQ ID NO: 140) | Moiety A<sup>&</sup> |
| 024 | 8G,22E,34R,36G (SEQ ID NO: 28) | (GAQP)19(GQKP) (SEQ ID NO: 91) | 26K, 116K (SEQ ID NO: 141) | Moiety A<sup>&</sup> |
| 025 | 8G,22E,34R,36G (SEQ ID NO: 28) | (GAQP)14(GQKP) (SEQ ID NO: 92) | 26K, 96K (SEQ ID NO: 142) | Moiety A<sup>&</sup> |
| 026 | 8G,22E,34R,36G (SEQ ID NO: 28) | (GAQP)11(GQKP) (SEQ ID NO: 93) | 26K, 84K (SEQ ID NO: 143) | Moiety A<sup>&</sup> |
| 027 | 8G,22E,34R,36G (SEQ ID NO: 28) | (GAQP)7(GQKP) (SEQ ID NO: 94) | 26K, 68K (SEQ ID NO: 144) | Moiety A<sup>&</sup> |
| 028 | 8G,22E,34R,36G (SEQ ID NO: 28) | (GAQP)5(GQKP) (SEQ ID NO: 95) | 26K, 60K (SEQ ID NO: 145) | Moiety A<sup>&</sup> |
| 029 | 8G,22E,34R,36G (SEQ ID NO: 28) | (GAQP)2(GQKP) (SEQ ID NO: 96) | 26K, 48K (SEQ ID NO: 146) | Moiety A<sup>&</sup> |
| 030 | 8G,22E,26R 34R,36G (SEQ ID NO: 32) | (GAQP)9(GQKP) (SEQ ID NO: 90) | 76K (SEQ ID NO: 147) | Moiety A<sup>&</sup> |
| 031 | 8G,22E,26R,34R,36G (SEQ ID NO: 32) | (GAQP)7(GQKP) (SEQ ID NO: 94) | 68K (SEQ ID NO: 148) | Moiety A<sup>&</sup> |
| 032 | 8G,22E,26R,34R,36G (SEQ ID NO: 32) | (GAQP)5(GQKP) (SEQ ID NO: 95) | 60K (SEQ ID NO: 149) | Moiety A<sup>&</sup> |
| 033 | 8G,22E,26R,34R,36G (SEQ ID NO: 32) | (GAQP)2(GQKP) (SEQ ID NO: 96) | 48K (SEQ ID NO: 150) | Moiety A<sup>&</sup> |
| 034 | 8Aib,26C,34R,36G (SEQ ID NO: 4) | (GAQP)19(GQCP) (SEQ ID NO: 105) | 26C, 116C (SEQ ID NO: 151) | Moiety B<sup>&&</sup> |
| 035 | 8Aib,26C,34R,36G (SEQ ID NO: 4) | (GAQP)14(GQCP) (SEQ ID NO: 106) | 26C, 96C (SEQ ID NO: 152) | Moiety B<sup>&&</sup> |
| 036 | 8Aib,26C,34R,36G (SEQ ID NO: 4) | (GAQP)11(GQCP) (SEQ ID NO: 107) | 26C, 84C (SEQ ID NO: 153) | Moiety B<sup>&&</sup> |
| 037 | 8Aib,26C,34R,36G (SEQ ID NO: 4) | (GAQP)9(GQCP) (SEQ ID NO: 104) | 26C, 76C (SEQ ID NO: 154) | Moiety B<sup>&&</sup> |
| 038 | 8Aib,26C, 34R,36G (SEQ ID NO: 4) | (GAQP)7(GQCP) (SEQ ID NO: 108) | 26C, 68C (SEQ ID NO: 155) | Moiety B<sup>&&</sup> |
| 039 | 8Aib,26C,34R,36G (SEQ ID NO: 4) | (GAQP)5(GQCP) (SEQ ID NO: 109) | 26C, 60C (SEQ ID NO: 156) | Moiety B<sup>&&</sup> |
| 040 | 8Aib,26C,34R,36G (SEQ ID NO: 4) | (GAQP)2(GQCP) (SEQ ID NO: 110) | 26C, 48C (SEQ ID NO: 157) | Moiety B<sup>&&</sup> |
| 041 | 8Aib,26R 34R,36G (SEQ ID NO: 7) | (GAQP)9(GQCP) (SEQ ID NO: 104) | 76C (SEQ ID NO: 158) | Moiety B<sup>&&</sup> |
| 042 | 8Aib,26R,34R,36G (SEQ ID NO: 7) | (GAQP)7(GQCP) (SEQ ID NO: 108) | 68C (SEQ ID NO: 159) | Moiety B<sup>&&</sup> |
| 043 | 8Aib,26R,34R,36G (SEQ ID NO: 7) | (GAQP)5(GQCP) (SEQ ID NO: 109) | 60C (SEQ ID NO: 160) | Moiety B<sup>&&</sup> |
| 044 | 8Aib,26R,34R,36G (SEQ ID NO: 7) | (GAQP)2(GQCP) (SEQ ID NO: 110) | 48C (SEQ ID NO: 161) | Moiety B<sup>&&</sup> |
| 045 | 8G,22E,26C,34R,36G (SEQ ID NO: 29) | (GAQP)9(GQCP) (SEQ ID NO: 104) | 26C, 76C (SEQ ID NO: 162) | Moiety B<sup>&&</sup> |
| 046 | 8G,22E,26C,34R,36G (SEQ ID NO: 29) | (GAQP)19(GQCP) (SEQ ID NO: 105) | 26C, 116C (SEQ ID NO: 163) | Moiety B<sup>&&</sup> |
| 047 | 8G,22E,26C,34R,36G (SEQ ID NO: 29) | (GAQP)14(GQCP) (SEQ ID NO: 106) | 26C, 96C (SEQ ID NO: 164) | Moiety B<sup>&&</sup> |
| 048 | 8G,22E,26C,34R,36G (SEQ ID NO: 29) | (GAQP)11(GQCP) (SEQ ID NO: 107) | 26C, 84C (SEQ ID NO: 165) | Moiety B<sup>&&</sup> |
| 049 | 8G,22E,26C,34R,36G (SEQ ID NO: 29) | (GAQP)7(GQCP) (SEQ ID NO: 108) | 26C, 68C (SEQ ID NO: 166) | Moiety B<sup>&&</sup> |
| 050 | 8G,22E,26C,34R,36G (SEQ ID NO: 29) | (GAQP)5(GQCP) (SEQ ID NO: 109) | 26C, 60C (SEQ ID NO: 167) | Moiety B<sup>&&</sup> |
| 051 | 8G,22E,26C,34R,36G (SEQ ID NO: 29) | (GAQP)2(GQCP) (SEQ ID NO: 110) | 26C, 48C (SEQ ID NO: 168) | Moiety B<sup>&&</sup> |
| 052 | 8G,22E,26R 34R,36G (SEQ ID NO: 32) | (GAQP)9(GQCP) (SEQ ID NO: 104) | 76C (SEQ ID NO: 169) | Moiety B<sup>&&</sup> |

TABLE 1-continued

Exemplary polypeptide conjugate sequences

| Molecule Code (MLC) | Mutations in GLP-1** (SEQ ID NO of the GLP-1) | Repeating sequences and number of repeats (SEQ ID NO of the peptide linker) | CRM residue(s)# (SEQ ID NO of the polypeptide portion) | CRM |
|---|---|---|---|---|
| 053 | 8G,22E,26R,34R,36G (SEQ ID NO: 32) | (GAQP)7(GQCP) (SEQ ID NO: 108) | 68C (SEQ ID NO: 170) | Moiety B&& |
| 054 | 8G,22E,26R,34R,36G (SEQ ID NO: 32) | (GAQP)5(GQCP) (SEQ ID NO: 109) | 60C (SEQ ID NO: 171) | Moiety B&& |
| 055 | 8G,22E,26R,34R,36G (SEQ ID NO: 32) | (GAQP)2(GQCP) (SEQ ID NO: 110) | 48C (SEQ ID NO: 172) | Moiety B&& |
| 056 | 8Aib,22E,34R,36G (SEQ ID NO: 8) | (GAQP)9GAQK (SEQ ID NO: 175) | 26K, 77K (SEQ ID NO: 173) | Moiety A& |
| 057 | 8Aib,22E,34R,36G (SEQ ID NO: 8) | (GAQP)7GAQK (SEQ ID NO: 176) | 26K, 69K (SEQ ID NO: 174) | Moiety A& |
| 058 | 8Aib,22E, 26C,34R,36G (SEQ ID NO: 184) | (GAQP)19(GQCP) (SEQ ID NO: 105) | 26C, 116C (SEQ ID NO: 177) | Moiety B&& |
| 059 | 8Aib,22E, 26C,34R,36G (SEQ ID NO: 184) | (GAQP)14(GQCP) (SEQ ID NO: 106) | 26C, 96C (SEQ ID NO: 178) | Moiety B&& |
| 060 | 8Aib,22E, 26C,34R,36G (SEQ ID NO: 184) | (GAQP)11(GQCP) (SEQ ID NO: 107) | 26C, 84C (SEQ ID NO: 179) | Moiety B&& |
| 061 | 8Aib,22E, 26C,34R,36G (SEQ ID NO: 184) | (GAQP)9(GQCP) (SEQ ID NO: 104) | 26C, 76C (SEQ ID NO: 180) | Moiety B&& |
| 062 | 8Aib,22E, 26C,34R,36G (SEQ ID NO: 184) | (GAQP)7(GQCP) (SEQ ID NO: 108) | 26C, 68C (SEQ ID NO: 181) | Moiety B&& |
| 063 | 8Aib,22E, 26C,34R,36G (SEQ ID NO: 184) | (GAQP)5(GQCP) (SEQ ID NO: 109) | 26C, 60C (SEQ ID NO: 182) | Moiety B&& |
| 064 | 8Aib,22E, 26C,34R,36G (SEQ ID NO: 184) | (GAQP)2(GQCP) (SEQ ID NO: 110) | 26C, 48C (SEQ ID NO: 183) | Moiety B&& |
| 065 | 8Aib,34R,36G (SEQ ID NO: 3) | (GAQP)9(GQCP) (SEQ ID NO: 104) | 76C (SEQ ID NO: 185) | Moiety B&& |
| 066 | 8Aib,34R,36G (SEQ ID NO: 3) | (GAQP)7(GQCP) (SEQ ID NO: 108) | 68C (SEQ ID NO: 186) | Moiety B&& |
| 067 | 8Aib,34R,36G (SEQ ID NO: 3) | (GAQP)5(GQCP) (SEQ ID NO: 109) | 60C (SEQ ID NO: 187) | Moiety B&& |
| 068 | 8Aib, 22E, 34R, 36G (SEQ ID NO: 8) | (GAQP)9(GQCP) (SEQ ID NO: 104) | 76C (SEQ ID NO: 188) | Moiety B&& |
| 069 | 8Aib, 22E, 34R, 36G (SEQ ID NO: 8) | (GAQP)7(GQCP) (SEQ ID NO: 108) | 68C (SEQ ID NO: 189) | Moiety B&& |
| 070 | 8Aib, 22E, 34R, 36G (SEQ ID NO: 8) | (GAQP)5(GQCP) (SEQ ID NO: 109) | 60C (SEQ ID NO: 190) | Moiety B&& |

**: Mutations in GLP-1 means mutations relative to SEQ ID NO: 1, wherein the first residue is 7H, and the last residue is 37G;
: CRM residue(s) means position of the CRM residue counted from N to C in the polypeptide sequence containing GLP-1 (wherein the first residue is 7H) with its C-terminus attached to the peptide linker.
&: refers to HOOC—(CH2)16—CO—gGlu—2XADO or

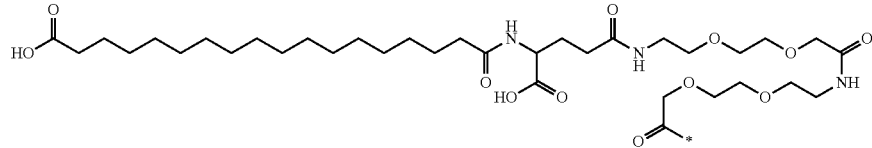 [SMILES: *C(=O)COCCOCCNC(=O)COCCOCCNC(=O)CCC(NC(=O)CCCCCCCCCCCCCCCCC(=O)O)C(=O)O]

&&: Moiety B refers to HOOC—(CH2)16—CO—gGlu—2XADO—EDA—CO—CH2, or the following structure:

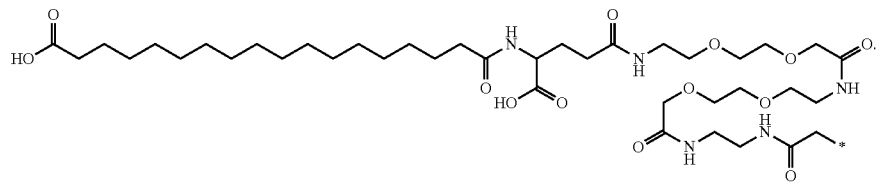 [SMILES: *CC(=O)NCCNC(=O)COCCOCCNC(=O)COCCOCCNC(=O)CCC(NC(=O)CCCCCCCCCCCCCCCCC(=O)O)C(=O)O]

In certain embodiments, the polypeptide conjugate comprises a structure shown below, where the amino acid residues are represented as one letter abbreviations in grey circles:
Molecule 001
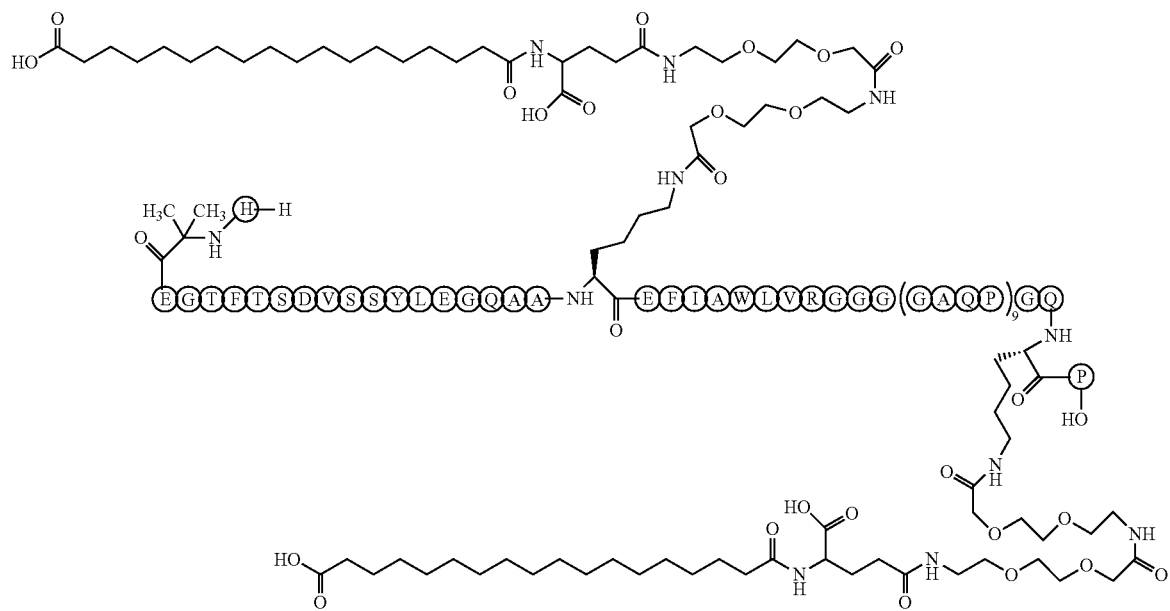
Molecule 002
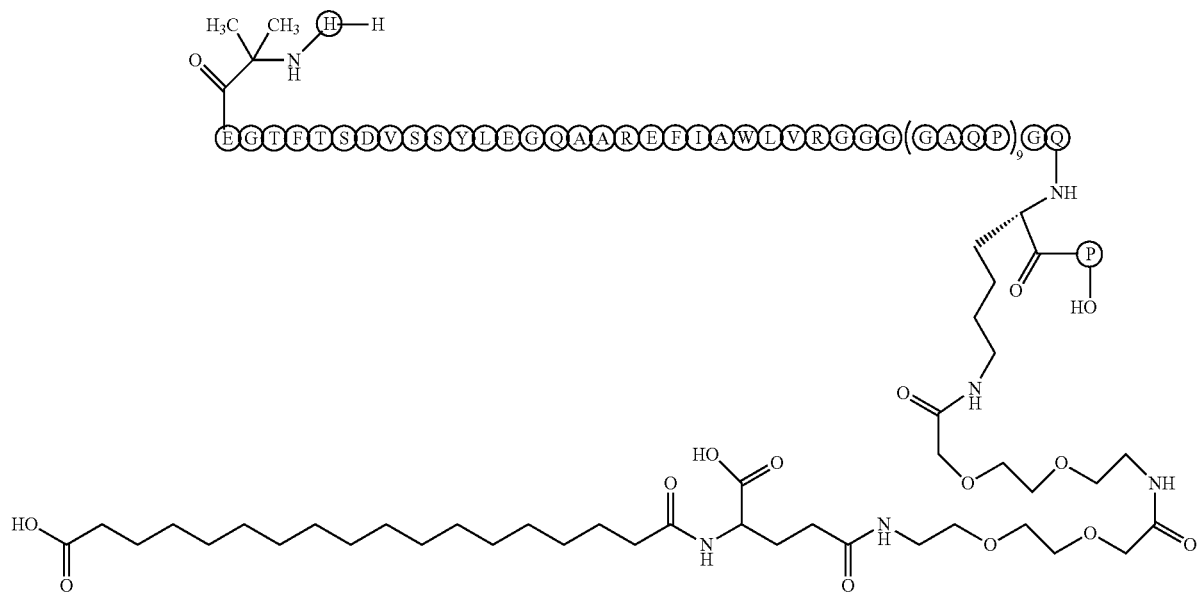

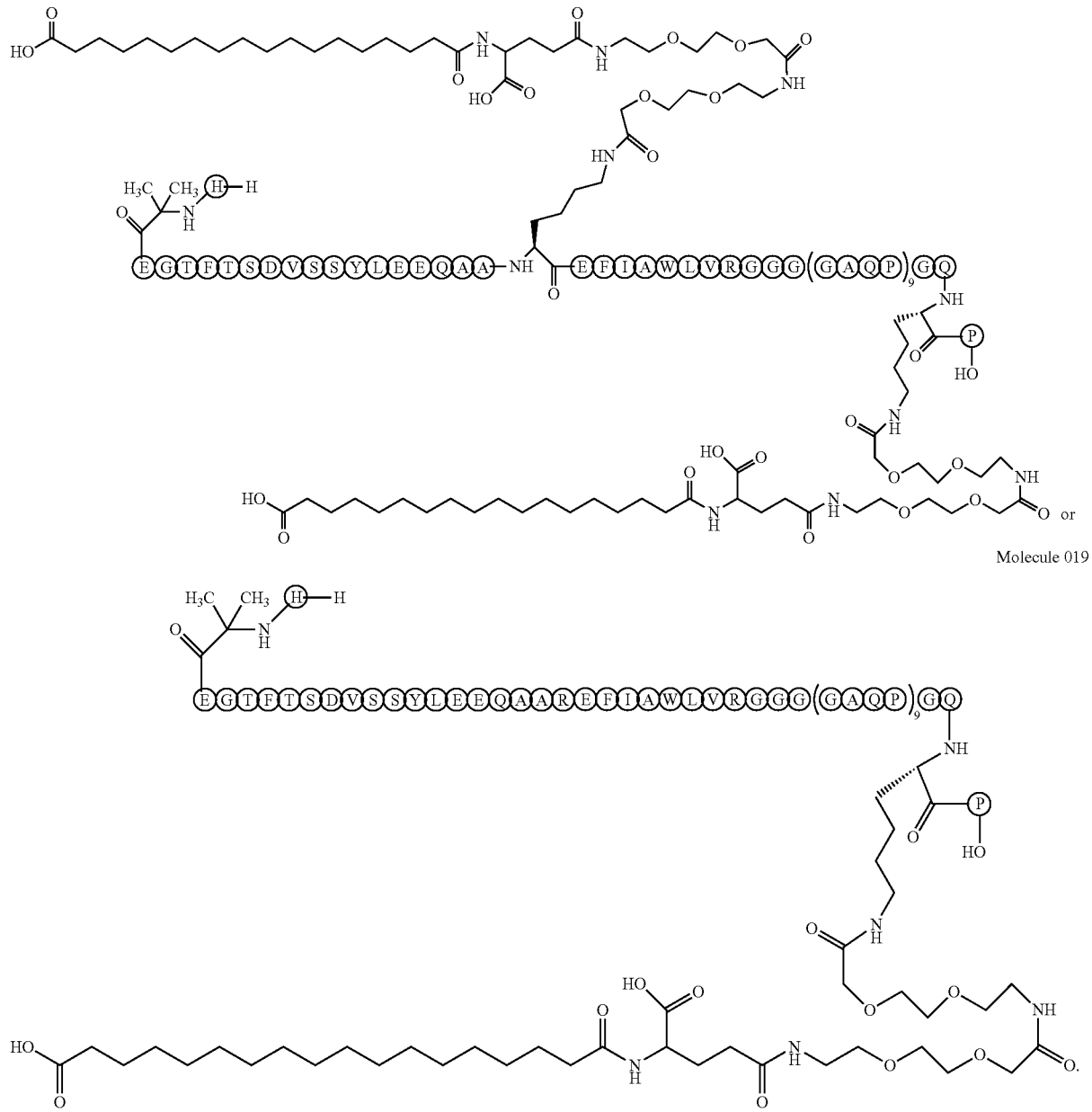

Method of Preparation

The present disclosure provides isolated nucleic acids or polynucleotides that encode the polypeptide portion (or a fragment thereof) of the polypeptide conjugates provided herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides, Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem, 260: 2605-2608 (1985); and Rossolini et at, Mol. Cell. Probes 8:91-98 (1994)).

The nucleic acids or polynucleotides encoding the polypeptide provided herein (or fragment thereof) can be constructed using recombinant techniques, To this end, DNA encoding the GLP-1 receptor agonist (such as GLP-1) and DNA encoding the peptide linker can be obtained and operably linked to allow transcription and expression in a host cell to produce the fusion polypeptide. If needed, polynucleotide sequences encoding for one or more linkers are also operably linked to allow expression of the desired product.

The encoding polynucleotide sequences can be further operably linked to one or more regulatory sequences, optionally in an expression vector, such that the expression or production of the fusion polypeptides or polypeptide complexes is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, Ipp, npr, pac, syn, trc and T3, or eukaryotic promoters such as SV40, CMV, and EF-1α), and a transcription termination sequence.

Vectors and Host Cells

In another aspect, the present disclosure provides a vector comprising the polynucleotide provided herein.

[002.74] Vectors comprising the polynucleotide sequence (s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell or eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the GLP-1 polypeptide can be subcloned into an expression vector, which is expressed as inclusion bodies in the host cells. The vector can be a viral vector, and any suitable viral vector can be used in this capacity.

In another aspect, the present disclosure provides a host cell comprising the vector provided herein. The host cell is prokaryotic cell or a eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the polypeptide conjugates provided herein, comprising culturing the host cell provided herein under a condition that allows expression of the polynucleotide provided herein to obtain the polypeptide portion of the polypeptide conjugate.

For production of the polypeptide portion provided herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the polypeptide portion of the polypeptide conjugates provided herein, comprising culturing the host cell provided herein under the condition at which the polypeptide portion is expressed. In certain embodiments, the polypeptide portion is expressed as a soluble polypeptide.

When using recombinant techniques, the polypeptide provided herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min, Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the polypeptide.

The polypeptide provided herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

In certain embodiments, the method further comprises conjugating the CRM to the polypeptide. The polypeptide can be conjugated at, for example, the lysine residue, the cysteine residue, or the non-natural amino acid by a suitable conjugation reaction.

For example, the polypeptide having one or more CRM residues such as lysine may be reacted with an amino-reactive agent. In certain embodiments, the CRM is conjugated to the lysine residue via an acyl group in an acylation reaction. Exemplary methods of acylation reaction is described in, for example, WO2009083549 and WO2010029159, the content of which is incorporated herein to its entirety. The CRM to be conjugated in an acylation reaction may contain a carboxylic acid group, an α,ω-fatty diacid residue, an activated ester, or an activated N-hydroxy imide ester, among others. Examples of activated esters include, O-succinimide reagents like N-hydroxysuccinimidyl (NHS) or sulfo-NHS esters and imido ester compounds like Traut's reagent, which can react with the ε-amino group of a conjugatable lysine residue to form amide or amidine bonds. Additional examples of suitable amino-reactive agent include, O-acylisourea, N-hydroxy trialzole esters, anhydride, phenyl active esters; P-hydroxamic active esters, acylimidazoles, acylbenzotriazoles, acyl azides, acid hylides, phophonium salts, aminium/uronium salts.

For another example, the polypeptide having one or more CRM residues such as cysteine may be linked to a thiol-reactive agent. In certain embodiments, the CRM is conjugated to the cysteine residue in an alkylation reaction. In certain embodiments, the CRM is conjugated to the conjugatable cysteine residue via a maleimide or an iodoacetamide to form a carbon-sulfur bond. In certain embodiments, the CRM is conjugated to the conjugatable cysteine residue via a disulphide to form a disulfide bond. Additional examples of suitable thiol-reactive group include, dienyl sulfone, α-haloacyl, or other thiol-reactive conjugation partner. See, for details, Haugland, 2003, Molecular Probes Handbook of Fluorescent Probes and Research Chemicals, Molecular Probes; Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671.

For example, the polypeptide having one or more CRM residues such as non-natural amino acid residue (NNAA) can be conjugated to a CRM such that a stable linkage can be formed between the NNAA of the fusion polypeptide and the CRM. For example, NNAAs containing keto group or aldehyde or β-diketomoieties can react with a hydrazide- or O-alkylhydroxylamine-, hydroxylamine-containing agents to form a hydrazone or an O-alkylated oxime linkage. For another example, NNAAs containing an azide group can react with an alkyne derivative to form a stable triazole linker by copper (I) catalyzed [3+2] cycloaddition (and vice versa). For another example, NNAAs containing an azide group can be ligated with an appropriate water soluble phosphine-containing agent to form an amide linkage by a Staudinger ligation. Further, a thioester moiety in an NNAA can react with an amine-containing agent to form amide linkage. The fusion polypeptides provided herein incorporated with an NNAA can be conjugated with an agent via cycloaddition reactions, such as (4+2) cycloaddition between diene and dienophile (Diels-Alder reaction), (3+2) cycloaddtion via 1, 3-dipolar Huisgen cycloaddition, and (3+2) cycloaddtion via Nitrone-olefin cycloaddition. Cycloaddition methods suitable for antibody conjugation have been described in, for example, WO05003294, US20120004183, WO06009901, WO07130453 and U.S. Pat. No. 6,737,236.

For another example, the polypeptide may be conjugated to biotin, then indirectly conjugated to CRM that is conjugated to avidin. For still another example, the fusion polypeptide or the polypeptide complex may be linked to a coupling agent which further links to the CRM. Examples of the coupling agents include bifunctional moieties such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suherate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulphide linkage.

Additional methods for the conjugation of CRM to the polypeptides are found, for example, in U.S. Pat. Nos. 5,208,020; 64,411,163; WO2005037992; WO2005081711; and WO2006/034488, which are incorporated herein by reference to the entirety, Specific examples of methods of preparing the conjugates of the present disclosure are also included in the experimental part of the present disclosure.

Pharmaceutical Composition

In another aspect, the present disclosure also provides a pharmaceutical composition comprising the polypeptide conjugate provided herein and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives; lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the fusion polypeptide; the polypeptide complex or the conjugate disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers; antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline; dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion, Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the polypeptide conjugate as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the fusion polypeptide, the polypeptide complex, or the conjugate provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Administration of the pharmaceutical composition as described herein may be via any route known to be effective by the physician of ordinary skill. One example is peripheral parenteral administration by a sterile syringe or some other mechanical device such as an infusion pump. In certain embodiments, peripheral parenteral route is intravenous, intramuscular, subcutaneous, or intraperitoneal routes of administration.

In certain embodiments, the polypeptide conjugates described herein is formulated in a form suitable for non-parenteral routes administration, such as oral, rectal, nasal, or lower respiratory routes administration.

In certain embodiments, the polypeptide conjugates described herein is formulated in a solid formulation such as lyophilization or spray drying, which is then reconstituted in a suitable diluent solution prior to administration. Standard pharmaceutical formulation techniques, such as those described in Remington; The Science and Practice of Pharmacy (D. B. Troy, Editor, 21st Edition, Lippincott, Williams & Wilkins, 2006), may be employed. Alternatively, the polypeptide conjugates described herein can be formulated for administration through the lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, transdermal, or pulmonary route. As a still further option, the polypeptide conjugates described herein can be formulated for administration through transdermal administration, for example, by needle-free injection or from a patch, optionally an iontophoretic patch, or transmucosal, for example, buccal, administration, Method of Treatment In another aspect, the present disclosure provides a method of preventing or treating a metabolic disorder in a subject in need thereof, comprising administering a therapeutically effective amount of the polypeptide conjugate provided herein.

Therapeutic methods are also provided, comprising: administering a therapeutically effective amount of the polypeptide conjugate provided herein to a subject in need thereof, thereby treating or preventing a condition or a disorder. In certain embodiments, the subject has been identified as having a disorder or condition likely to respond to the polypeptide conjugate provided herein.

In certain embodiments, the metabolic disorder is diabetes, obesity, overweight, non-alcoholic steatohepatitis (NASH), cardiovascular like dyslipidemia, artherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

In certain embodiments, the condition diabetes includes all forms of diabetes, such as hyperglycemia, type 2 diabetes, impaired glucose tolerance, type 1 diabetes, non-insulin dependent diabetes, KIDDY (maturity onset diabetes of the young), gestational diabetes, and/or an elevated level of HbA1C.

In certain embodiments, the condition diabetes includes diabetic complications such as angiopathy.

In another aspect, the present disclosure provides a method of managing body weight in a subject in need thereof, comprising administering a therapeutically effective amount of the polypeptide conjugate provided herein.

In another aspect, the present disclosure provides a method of reducing food intake in a subject in need thereof, comprising administering a therapeutically effective amount of the polypeptide conjugate provided herein.

In another aspect, the present disclosure provides a method of reducing body weight in a subject in need thereof, comprising administering a therapeutically effective amount of the polypeptide conjugate provided herein.

In certain embodiments, the condition or metabolic disorder that can be treated or ameliorated using the polypeptide conjugate provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL.

In certain embodiments, the condition or metabolic disorder that can be treated or ameliorated using the polypeptide conjugate provided herein, includes a condition where a human subject has a body mass index (BMI) of at least or higher than 25, 26, 27, 28, 29, 30, 31, 32, 33, 34, 35, 36, 37, 38, 39 or 40. In certain embodiments, the human subject has an BMI ranging from 25 to 30, 26 to 30, 27 to 30, 28 to 30, 25 to 29, or 25 to 28.

The therapeutically effective amount of the polypeptide conjugate provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the fusion polypeptide, the polypeptide complex and the conjugate provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the polypeptide conjugate provided herein may be administered at a therapeutically effective dosage of about 0.01 mg/kg to about 100 mg/kg (e.g., about 0.01 mg/kg, about 0.5 mg/kg, about mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the polypeptide conjugate provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

In certain embodiments, the polypeptide conjugate provided herein may be administered to the subject (e.g. human) at a dosing regimen that is no more frequently than once daily, once every 3 days, once weekly, once every two weeks, once every three weeks, or once monthly. In certain embodiments, the polypeptide conjugate provided herein may be administered to the subject (e.g. human) at a dosing interval of once weekly, once every two weeks, once every three weeks, or once monthly. Therapeutic efficacy with low dosing frequency have the potential to improve a patient's adherence and long-term treatment success. The currently available treatment semaglutide is dosed once weekly. Without wishing to be bound by any theory, it is believed that certain polypeptide conjugate provided herein have significantly extended half life and are suitable for less frequent dosing than semaglutide for treating a metabolic condition, for example, less frequent than once weekly dosing (e.g. once every 8 days, once every 9 days, once every 10 days, once every 11 days, once every 12 days, once every 13 days, once every 14 days, once every 18 days, once every three weeks, once every 24 days, once every 4 weeks, or once every month). In certain embodiments, the dosing regimen is a continuous dosing regimen selected from twice-weekly dosing, once-weekly dosing, once bi-weekly dosing, once every three weeks dosing, once monthly dosing, or once every two months dosing. In certain embodiments, the dosing regimen has a dosing interval ranging from about once every 3 days to about once per month, or from about once weekly to about once per month.

Dosage regimens may be adjusted to provide the optimum desired response (e.g., a therapeutic response). For example, a single dose may be administered, or several divided doses may be administered over time.

The polypeptide conjugate provided herein may be administered by any route known in the art, such as for example parenteral (e.g., subcutaneous, intraperitoneal, intravenous, including intravenous infusion, intramuscular, or intradermal injection) or non-parenteral (e.g.; oral, intranasal, intraocular, sublingual, rectal, or topical) routes. In certain embodiments, the polypeptide conjugate provided herein is administered subcutaneously, intravenously, intramuscularly or intradermally.

The polypeptide conjugate may be administered alone or in combination with one or more additional therapeutic means or agents.

In certain embodiments, when used for treating a metabolic disease, the polypeptide conjugate provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art. A non-limiting list of examples of compounds that can be administered in combination with a pharmaceutical composition comprising the polypeptide conjugates provided herein, include rosiglitizone, pioglitazone, repaglinide, nateglitinide, metformin, exenatide, stiagliptin, pramlintide, glipizide, glimeprirideacarbose, and miglitol.

Kit

Also provided are kits for practicing the disclosed methods. Such kits can comprise a pharmaceutical composition such as those described herein, including nucleic acids encoding the polypeptide conjugate provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of the polypeptide conjugate provided herein or a mutant form thereof; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular like dyslipidemia, artherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the Internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Example 1: Recombinant Expression and Purification of GLP-1 Proteins

The GLP-1 proteins listed in Table 1 were produced from bacterial *E. coli* expression system, using BL21(DE3) derivative strain. The DNA coding for the GLP-1 precursors was codon optimized for *E. coli* expression, de novo synthesized and subcloned into PET derivative expression vectors (Novagen). Amino acid substitutions were accomplished by modification of the corresponding genetic codes. Overexpression of GLP-1 precursor was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours. Cells were harvested and lysed in 20 mM Tris pH8.0, 0.15M NaCl buffer by cell disruptor (900 bar, for twice). The soluble fractions, containing the GLP-1 proteins, were collected and by centrifugation (8,000×g, for 30 min). After removing tag by protease, the proteins were purified by reverse phase chromatography. The samples in each step were characterized by LC/MS to confirm the correct molecular weight.

Example 2: Incorporation of Non-Proteogenic Amino Acid in Recombinant Protein

The N-terminal His-Aib-Glu-Gly tetrapeptide or His-Aib dipeptide was dissolved in organic solvent and was added into a solution of GLP-1 protein in organic solvent. The reaction was stirred at room temperature for 3 h. Then the piperidine was added into the reaction solution to remove Fmoc-protecting group.

Example 3: Preparation of GLP-1 Compounds with CRMs

To a solution of a GLP-1 protein in NaOH was added with CRM reagent (i.e. HOOC—(CH2)16-CO-gGlu-2XADO) in organic solvent dropwise. The reaction was stirred at room temperature for 1 h. Then the product was applied to reverse phase chromatography. This provided the compounds as listed in Table 1 as shown above.

The conjugated GLP-1 proteins were detected and characterized by LC-MS method with Waters BioAccord LC-MS system, or by UPLC with Waters Acquity UPLC system, using conditions optimized for different conjugates, following the supplier's manuals.

Example 4a: In Vitro Activities

Method: The in vitro GLP-1 activities were measured using a BHC cell line overexpressing human GLP-1 receptor and CRE luciferase reporter with or without 1% human serum albumin (HSA). Tested fusion proteins were measured at 1 nM or 100 nM as top concentration when in the absence or presence of 1% HSA with 3-fold serial dilutions. After cells were treated with molecules for 4 hours, luciferase activities were measured by Steadylite plus kit (Perkin Elmer, 6066751).

The activity of each protein was represented by EC50, derived from non-linear regression analysis.

Conclusion: Almost all molecules show comparable or even better potency than semaglutide in the assay without HSA supplement. However, different molecules exhibited different degrees of reduction in GLP-1 activity (i.e, increased $EC_{50}$) in the presence of 1% HSA. Data in Table 2 suggested that linker length, fatty acid position and number of conjugated fatty acid moieties could be relevant to GLP-1 activities. As shown in Table 2, the molecules (whether mono-acylation or double-acylation) having a short linker length (i.e. 12 amino acid residues) had significantly reduced GLP1-activity, as compared with those molecules with longer linker lengths. As the distance increased between the C-terminal residue of GLP-1 and the CRM residue (i.e. lysine in the linker), the GLP-1 activity of the molecules in the presence of HSA seemed to steadily improve.

As shown in Table 2, mono-acylated Molecules 002, 010 and 011 showed much higher activity than semaglutide in the presence of 1% HSA. For double-acylated Molecules 012, 016, 004, 006, 007, 005, 001 and 061, all showed relatively lower GLP-1 activity in the presence of 1% HSA than semaglutide but were still in an acceptable range.

TABLE 2a

In vitro activities of GLP-1 polypeptide conjugates. To measure in vitro GLP-1 activity, a BHK cell line overexpressing human GLP-1 receptor was used.

| Molecule Code. | Linker length (aa) | Fatty acid number | Fatty acid position | GLP-1 activity ($EC_{50}$, pM) | GLP-1 activity ($EC_{50}$, pM, 1% HSA) |
|---|---|---|---|---|---|
| Semaglutide | 0 | Mono | GLP-1 | 4.2 | 243.8 |
| 001 | 40 | Double | GLP-1 and linker | 2.8 | 1036 |
| 002 | 40 | Mono | Linker | 1.1 | 8.6 |
| 005 | 48 | Double | GLP-1 and linker | 5.0 | 1537 |
| 006 | 32 | Double | GLP-1 and linker | 4.0 | 1387 |
| 007 | 24 | Double | GLP-1 and linker | 4.7 | 3238 |
| 008 | 12 | Double | GLP-1 and linker | 4.6 | 8732 |
| 004 | 60 | Double | GLP-1 and linker | 3.0 | 984.4 |
| 012 | 40 | Double | GLP-1 and linker | 2.1 | 1051 |
| 016 | 32 | Double | GLP-1 and linker | 2.1 | 1459 |
| 010 | 24 | Mono | Linker | 1.7 | 22.9 |
| 011 | 17 | Mono | Linker | 3.7 | 43.9 |
| 061 | 40 | Double | GLP-1 and linker | 4.4 | 2213 |

Example 4b: In Vitro Activities

Method: The in vitro GLP-1 activities were measured using a CHO cell line overexpressing human GLP-1 receptor and CRE luciferase reporter with or without 1% human serum albumin (HSA). Tested fusion proteins were measured at 30 nM or 600 nM as top concentration when in the absence or presence of 1% HSA with 3-fold serial dilutions. After cells were treated with molecules for 5 hours, luciferase activities were measured by Bright-Glo Luciferase Assay System (Promega, E2620). The activity of each protein was represented by EC50, derived from non-linear regression analysis.

Conclusion: As shown in Table 1, mono-acylated Molecules 002 (1006) and 1023 showed much higher activity than semaglutide in the presence of 1% HSA.

TABLE 2b

In vitro activities of GLP-1 polypeptide conjugates. To measure in vitro GLP-1 activity, a CHO cell line overexpressing human GLP-1 receptor was used.

| Molecule Code. | Linker length (aa) | Fatty acid number | Fatty acid position | GLP-1 activity ($EC_{50}$, nM) | GLP-1 activity ($EC_{50}$, nM, 1% HSA) |
|---|---|---|---|---|---|
| Semaglutide | 0 | Mono | GLP-1 | 0.33 | 23.8 |
| 002 | 40 | Mono | Linker | 0.12 | 3.47 |
| 019 | 40 | Mono | Linker | 0.07 | 2.16 |

Example 5: In Vivo Activities in C57 Lean Mice

Method: 10 week old male C57BL/6 mice were injected subcutaneously with protein once on Day 1. Body weight was measured daily and five animals were used for each treatment group. Body weight was monitored for each individual animal. % BW loss=100*(BW on Day n-BW on Day 1)/(BW on Day 1), Data are indicated as mean values and standard error (SEM). The area under the curve for body weight loss (%) from 0 until 8 days (AUC ΔBW 0-8d) was calculated.

Figure 1B:
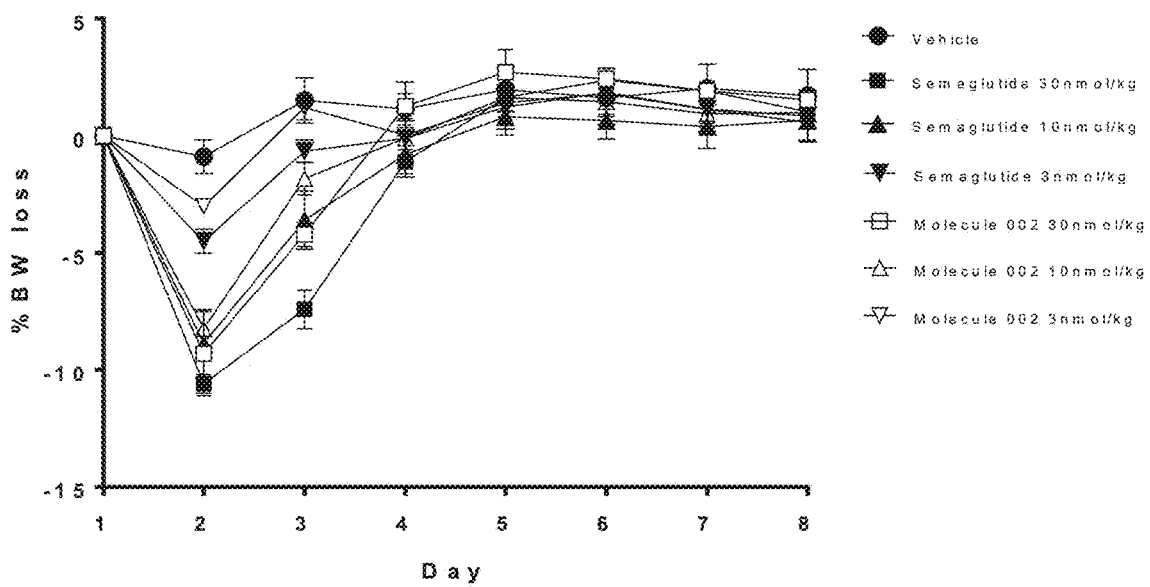
Figure 1C:
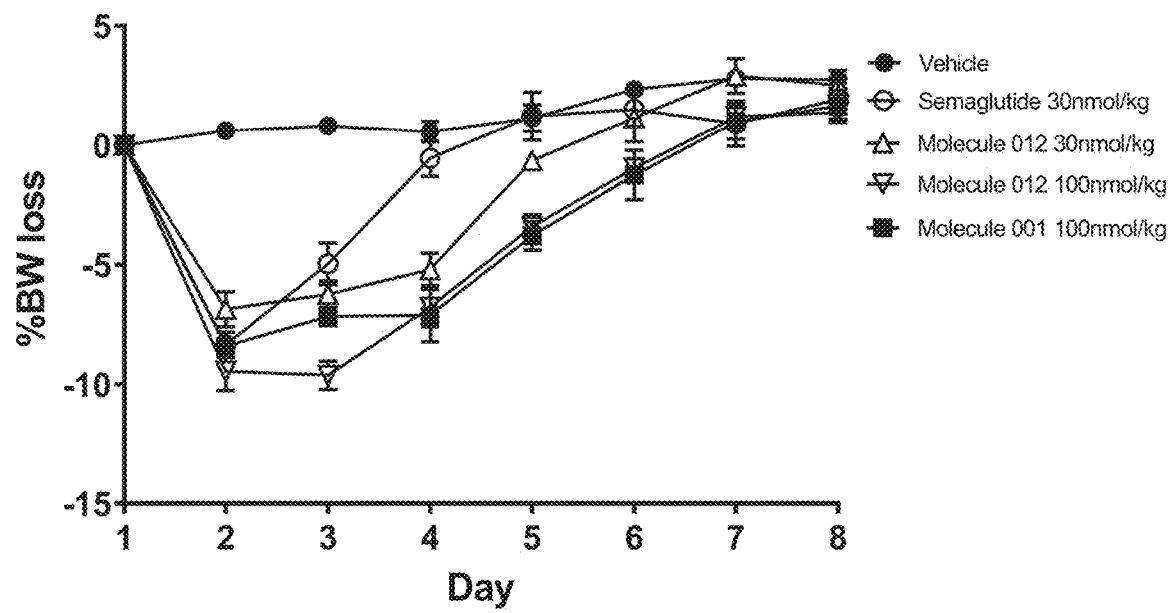
Figure 1D:
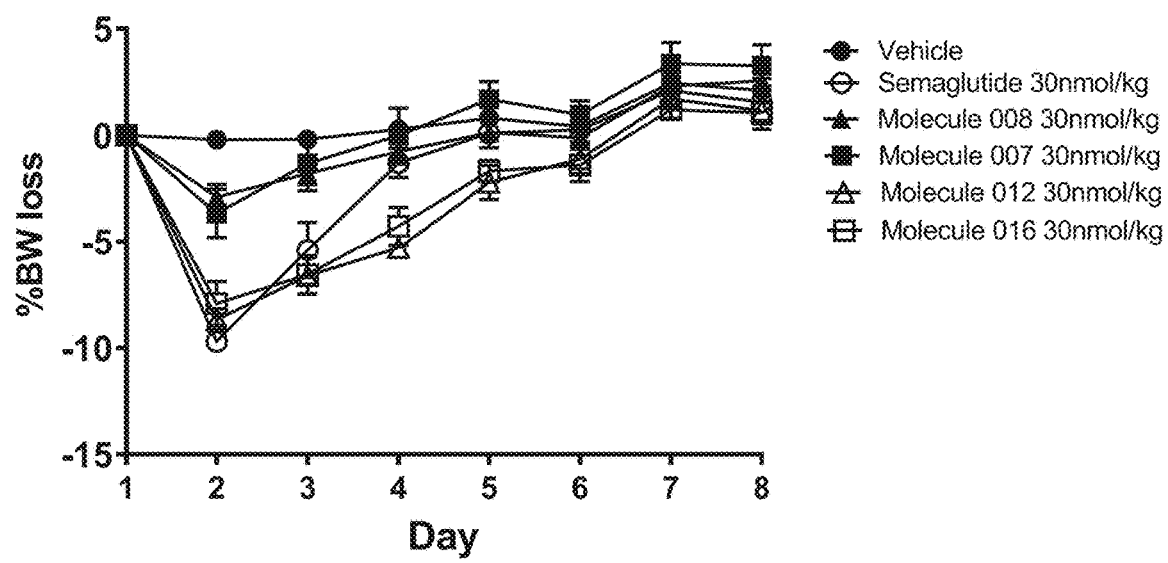
FIG. 1D shows body weight loss after Molecules 007, 008, 012 and 016 treatment from Day 1 to Day 8. Data are indicated as mean values and standard error (SEM). Semaglutide was tested in parallel as a comparative control.

Conclusion: Molecules 001, 002 and 012 showed dose dependent efficacy on body weight control (FIGS. 1A, 1B, 1C and Table 3). As shown in FIG. 1D and Table 3, Molecules 007 and 008 have less efficacy than Molecules 012 and 016 which is consistent with the in vitro activity data. Molecules 001, 016 and 012 with double fatty acids exhibited more sustainable efficacy than semaglutide, suggesting Molecules 001, 016 and 012 may have longer half-life (FIGS. 1A, 1C and 1D).

TABLE 3

The area under the curve for body weight loss (%) from 0 until 8 days (AUC ΔBW 0-8 d) in C57 lean mice studies.

| Studies | Group | AUC ΔBW 0-8 d (day* %) |
|---|---|---|
| Study 1 (FIG. 1A and 1B) | Semaglutide 30 nmol/kg | −12.7 |
| | Semaglutide 10 nmol/kg | −11.1 |
| | Semaglutide 3 nmol/kg | −0.6 |
| | Molecule 001 30 nmol/kg | −11.0 |
| | Molecule 001 10 nmol/kg | −1.6 |
| | Molecule 001 3 nmol/kg | 2.5 |
| | Molecule 002 30 nmol/kg | −4.4 |
| | Molecule 002 10 nmol/kg | −5.7 |
| | Molecule 002 3 nmol/kg | 2.8 |
| Study 2 (FIG. 1C) | Semaglutide 30 nmol/kg | −9.3 |
| | Molecule 012 30 nmol/kg | −13.6 |
| | Molecule 012 100 nmol/kg | −28.3 |
| | Molecule 001 100 nmol/kg | −25.9 |
| Study 3 (FIG. 1D) | Semaglutide 30 nmol/kg | −13.2 |
| | Molecule 008 30 nmol/kg | −1.85 |
| | Molecule 007 30 nmol/kg | −2.63 |
| | Molecule 012 30 nmol/kg | −21.6 |
| | Molecule 016 30 nmol/kg | −20.1 |

Example 6a: In Vivo Activities in db/db Mice

Method: 10 week old male db/db mice were injected subcutaneously with protein once. Fasting glucose was measured on different times and three animals were used for each group. Delta blood glucose is glucose subtracted by baseline level. Data are indicated as mean values and standard error (SEM).

Figure 2A:
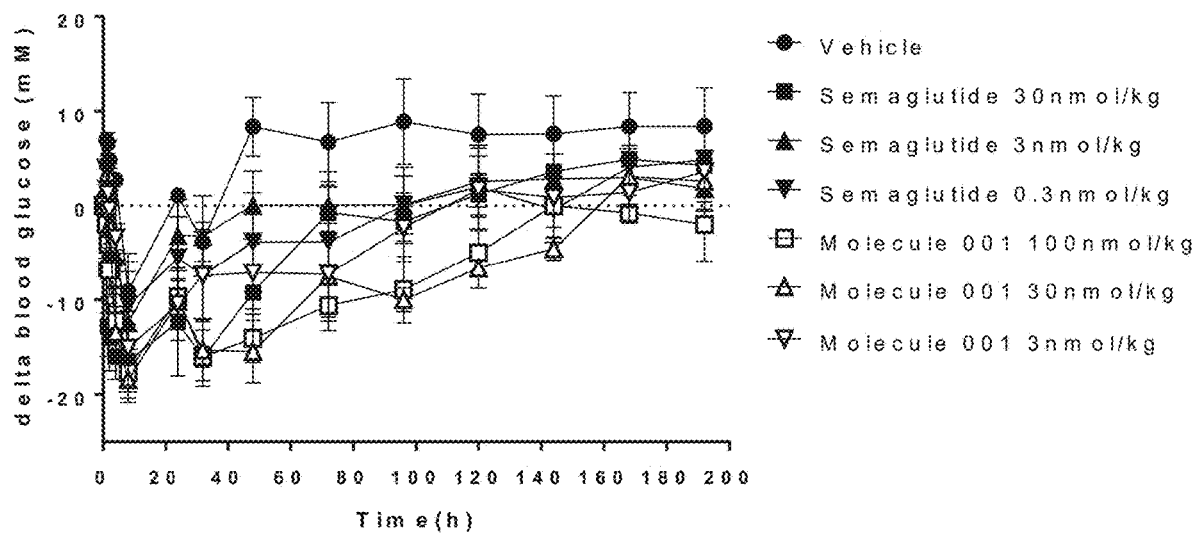
FIGS. 2A, 2B, 2C 2D and 2E show in vivo activities of Molecules 001, 002, 012 and 019 in db/db mice.
Figure 2B:
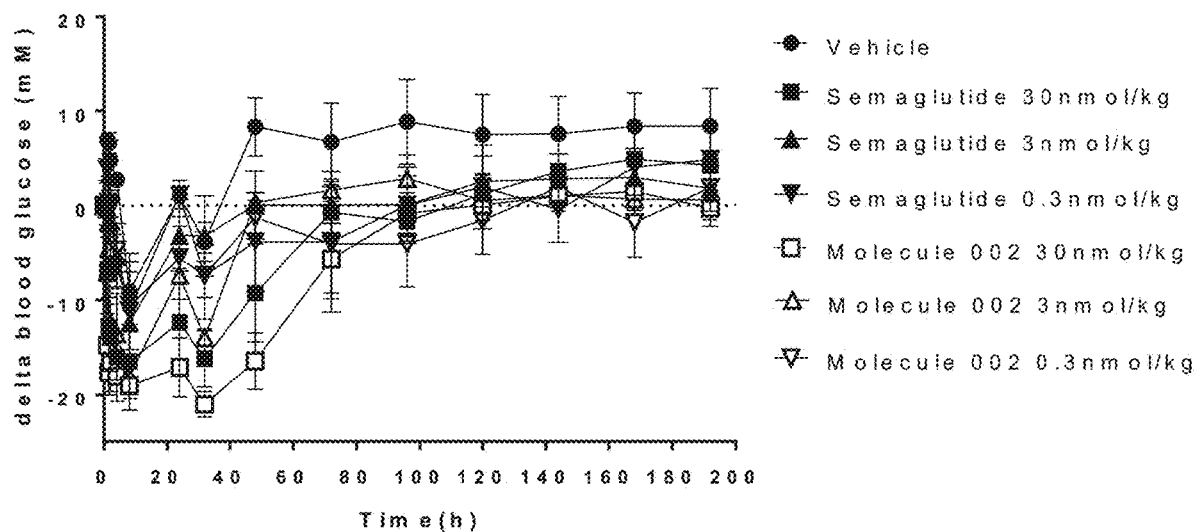

Conclusion: Both Molecules 001 and 002 showed dose dependent efficacy on glucose control (FIGS. 2A and 2B). Molecule 001 with double fatty acids exhibited more sustainable efficacy than semaglutide, suggesting Molecule 002 may have longer half-life.

Method: 10 weeks old male db/db mice were injected subcutaneously with protein once. Non-Fasting glucose was measured on different times and five animals were used for each group. Delta blood glucose is glucose subtracted by baseline level. Data are indicated as mean values and standard error (SEM). The area under the curve for delta blood glucose from 0 until 192 hours (AUCΔBG 0-192 h) was calculated.

Figure 2C:
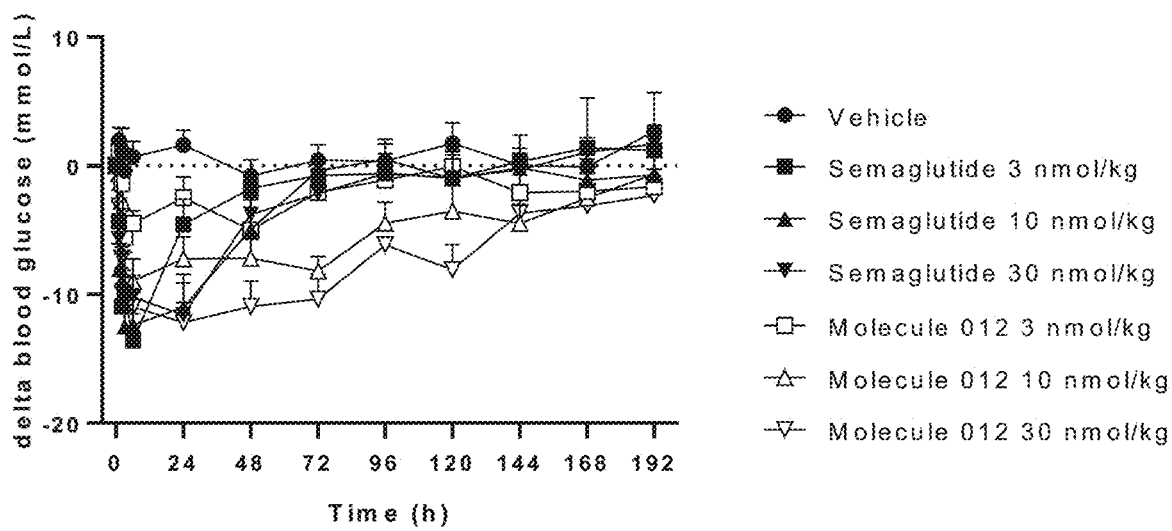

Conclusion: Molecule 012 showed dose dependent efficacy on glucose control (FIG. 2C, Table 4). Molecule 012 with double fatty acids exhibited more sustainable efficacy than semaglutide.

TABLE 4

The area under the curve for non-fasting delta blood glucose (%) from 0 until 192 hours (AUC ΔBG 0-192 h) in db/db mice for FIG. 2C.

| Group | AUC ΔBG 0-192 h (hr*mmol/L) |
|---|---|
| Semaglutide 3 nmol/kg | −317.0 |
| Semaglutide 10 nmol/kg | −583.4 |
| Semaglutide 30 nmol/kg | −527.1 |
| Molecule 012 3 nmol/kg | −424.5 |
| Molecule 012 10 nmol/kg | −1004.5 |
| Molecule 012 30 nmol/kg | −1447.0 |

Example 6b: In Vivo Activities in db/db Mice

Method: 10 week old male db/db mice were injected subcutaneously with Molecule 019 once. Random blood glucose was measured on different times and five animals were used for each group. Delta blood glucose is glucose subtracted by baseline level. Data are indicated as mean values and standard error (SEM).

Figure 2D:
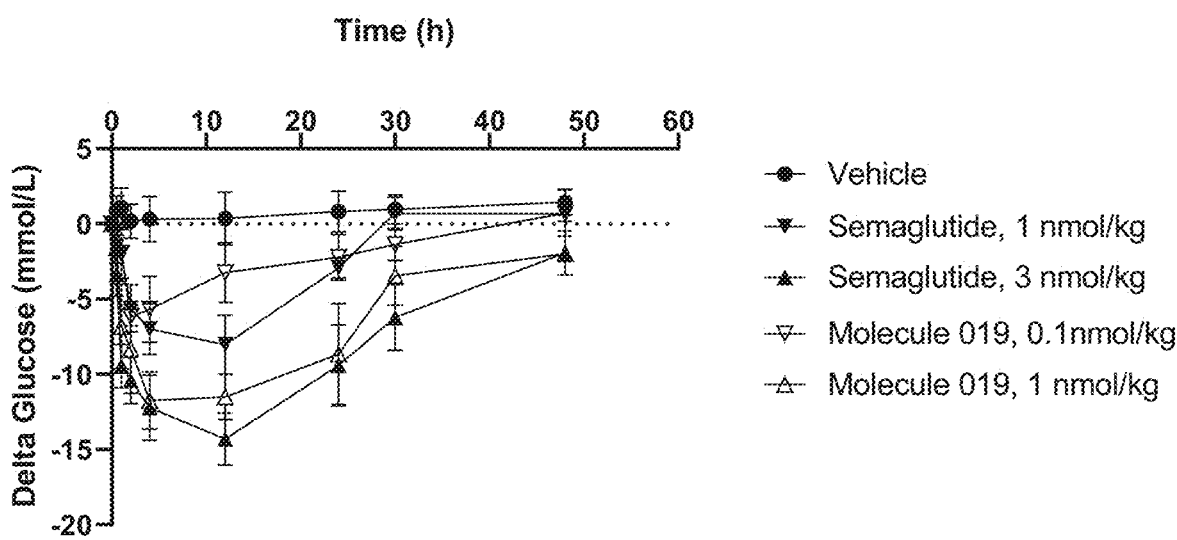
Figure 2E:
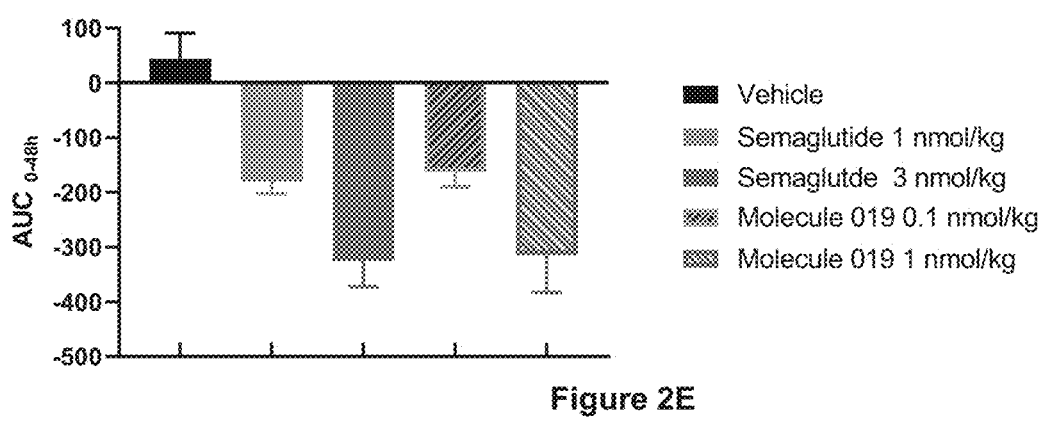

Conclusion: Molecule 019 showed dose dependent efficacy on glucose control (FIGS. 2D and 2E) and significantly higher potency than semaglutide.

Example 7: Pharmacokinetic Measurement

Method: 6-8 week old male C57BL/6 mice were administrated in a single subcutaneous dose of 30 nmol/kg protein (n=3/group). Plasma samples were collected pre-dose (−5 min), 0.5 hr, 1 hr, 2 hr, 4 hr, 6 hr, 8 hr, 12 hr, 24 hr, 48 hr, 72 hr, 96 hr, 120 hr, 144 hr, 168 hr and 192 hr after the injection. The concentrations of proteins in the plasma were measured by ELISA assay. Based on the graph showing plasma concentration of each protein versus time after subcutaneous injection, the pharmacokinetic parameters were calculated by WinNonlin.

Conclusion: Molecule 001 and 012 showed longer half-life than semaglutide and Molecule 002 in mouse (Table 5), consistent with in vivo efficacies.

TABLE 5

Pharmacokinetic parameters of GLP-1 polypeptide conjugates in mice. Pharmacokinetic data were analyzed by WinNonlin software. Tmax, Cmax, $T_{1/2}$, AUC were calculated for each molecule.

| PK parameters | Unit | Semaglutide | Molecule 001 | Molecule 002 | Molecule 012 |
|---|---|---|---|---|---|
| $T_{max}$ | hr | 6.7 | 32 | 4 | 24 |
| $C_{max}$ | nmol/L | 43.1 | 172.0 | 86.5 | 134 |
| Terminal $t_{1/2}$ | hr | 7.4 | 30.1 | 7.2 | 28.2 |
| $AUC_{tau}$ | hr*nmol/L | 614.7 (Tau = 24 h) | 12256 (Tau = 168 h) | 1507 (Tau = 48 h) | 7752 (tau = 192 h) |

Method: 6-8 weeks male SD rats were administrated in a single subcutaneous dose of 15 nmol/kg protein (n=3/group) and a single intravenous dose of 15 nmol/kg protein (n=3/group), respectively. Plasma samples were collected pre-dose (−5 min), 0.5 hr, 1 hr, 2 hr, 4 hr, 6 hr, 8 hr, 24 hr, 32 hr, 48 hr, 72 hr, 96 hr, 120 hr, 144 hr, 168 hr, 192 hr, 216 hr and 240 hr after subcutaneous administration. Plasma samples were collected pre-dose (−5 min), 0.083 hr, 0.25 hr, 0.5 hr, 1 hr, 2 hr, 4 hr, 6 hr, 8 hr, 24 hr, 32 hr, 48 hr, 72 hr, 96 hr and 120 hr after intravenous administration The concentrations of the polypeptide conjugates in the plasma were measured by LC-MS/MS method. Based on the graph showing plasma concentration of each polypeptide conjugate versus time after subcutaneous injection, the pharmacokinetic parameters were calculated by WinNonlin.

Conclusion: As shown in Table 6, Molecule 001 and 012 showed longer half-life than semaglutide, which was reported to have a T1l2 of 12 hrs (s.c. administration, as reported in non-clinical reviews from FDA) in rat.

TABLE 6

Pharmacokinetic parameters of GLP-1 polypeptide conjugates in rats. Pharmacokinetic data were analyzed by WinNonlin software. Tmax, Cmax, $T_{1/2}$, AUC were calculated for each molecule.

| PK parameters | Unit | Molecule 001 | | Molecule 012 | |
|---|---|---|---|---|---|
| | | i.v. | s.c. | i.v. | s.c. |
| $T_{max}$ | hr | NA | 24 | NA | 26.7 |
| $C_{max}$ (C0 for iv) | nmol/L | 317 | 56.2 | 231 | 52.0 |
| Terminal $t_{1/2}$ | hr | 26.9 | 25.8 | 26.9 | 26.9 |
| $AUC_{tau}$ | hr*nmol/L | 4485 | 2887 | 4140 | 7954 |
| | | (Tau = 120 h) | (Tau = 192 h) | (Tau = 120 h) | (Tau = 192 h) |
| F | % | NA | 64 | NA | 71 |

NA: not available.

Method: 10-month old male Bama minipigs were administrated with a single subcutaneous dose of 5 nmol/kg GLP-1 polypeptide conjugate (n=2/group) and a single intravenous dose of 5 nmol/kg protein (n=2/group), respectively. Plasma samples for Molecule 012 and semaglutide group were collected pre-dose (−5 min), 0.5 hr, 1 hr, 3 hr, 8 hr, 24 hr, 48 hr, 72 hr, 96 hr, 168 hr, 336 hr, 504 hr and 672 hr after subcutaneous administration. Plasma samples for Molecule 012 and semaglutide group were collected pre-dose (−5 min), 0.083 hr, 0.5 hr, 1 hr, 3 hr, 8 hr, 24 hr, 48 hr, 72 hr, 96 hr, 168 hr, 336 hr and 504 hr after intravenous administration. For semaglutide group, the concentrations of proteins in the plasma were measured by ELISA assay. For Molecule 012 group, the concentrations of proteins in the plasma were measured by LC-MS/MS method. Based on the graph showing plasma concentration of each GLP-1 polypeptide conjugate versus time after administration, the pharmacokinetic parameters were calculated by WinNonlin.

Conclusion: Molecule 012 showed longer half-life than semaglutide in minipigs (Table 7)

TABLE 7

Pharmacokinetic parameters of GLP-1 polypeptide conjugates in minipigs. Pharmacokinetic data were analyzed by WinNonlin software. Tmax, Cmax, $T_{1/2}$, AUC were calculated for each molecule.

| PK parameters | Unit | Semaglutide | | Molecule 012 | |
| --- | --- | --- | --- | --- | --- |
| | | i.v. | s.c. | i.v. | s.c. |
| $T_{max}$ | hr | NA | 16 | NA | 60 |
| $C_{max}$ (C0 for iv) | nmol/L | 188 | 54.9 | 236 | 71.4 |
| Terminal $t_{1/2}$ | hr | 53.0 | 62.8 | 136 | 147 |
| $AUC_{tau}$ | hr*nmol/L | 6643 | 5658 | 19617 | 16830 |
| | | (Tau = 336 h) | (Tau = 336 h) | (Tau = 504 h) | (Tau = 672 h) |
| F | % | NA | 85 | NA | 86 |

Example 8: Efficacy Study in Disease Models

Selected molecules are assessed in disease animal models (such db/db mice) to determine body weight, food intake, glucose efficacy with dose responses in chronic studies. Some biomarkers are also measured, including fasting insulin, plasma triglyceride, cholesterol, liver triglyceride, and inflammatory biomarkers (ALT, AST and CRP).

Method:

22 week old DIO male C57BL/6 mice (~50 g) were injected once every other day (Q2D) subcutaneously with designated GLP-1 polypeptide conjugates (i.e., Molecule 012) for 25 days. Food intake and body weight were measured twice a week and fasting blood glucose was measured once a week. Five animals were used for each treatment group. Body weight and fasting blood glucose was monitored for each individual animal, but food intake for each group animals was measured together. Day 1 and Day 25 are first day and last day of molecule dosage. Data are indicated as mean values and standard error (SEM) or pooled values. Statistical analysis was performed by One-way ANOVA. Body weight reduction on Day 25 is calculated by −1*(% BW loss−% BW loss of vehicle group); Cumulative food intake reduction is calculated by −100* (cumulative food intake−cumulative food intake of vehicle)/ cumulative food intake of vehicle.

Figure 3A:
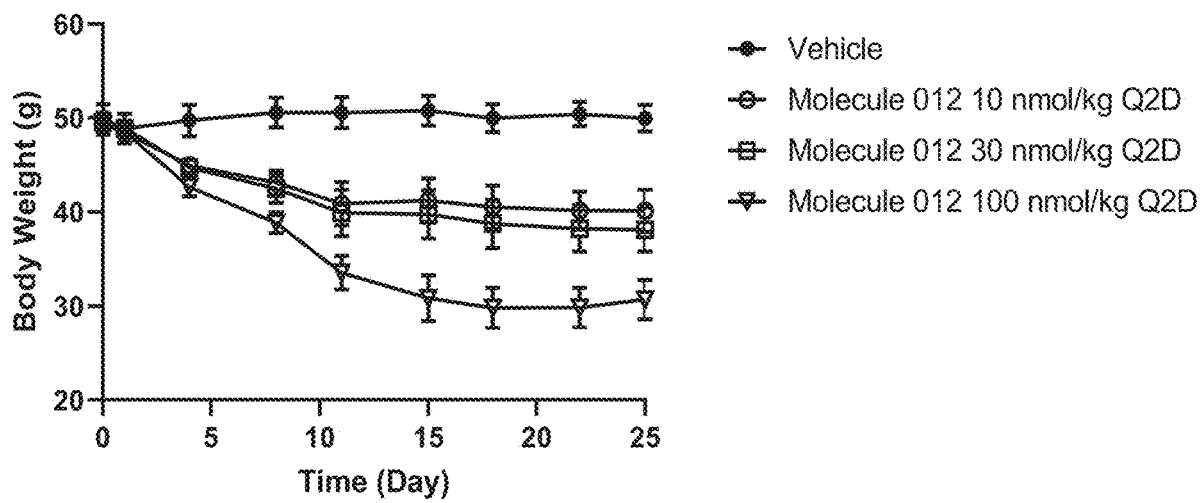
FIGS. 3A and 3B show in vivo efficacy in Diet Induced Obese (D10) mice. To evaluate the effects of the respective GLP-1 polypeptide conjugates on body weight, food intake and glucose levels, 22-week old DIO mice (C57BL/6 mice on high fat diet for 13 weeks) were administered every other day subcutaneously with different concentrations of the designated GLP-1 polypeptide conjugates for 25 days.
Figure 3B:
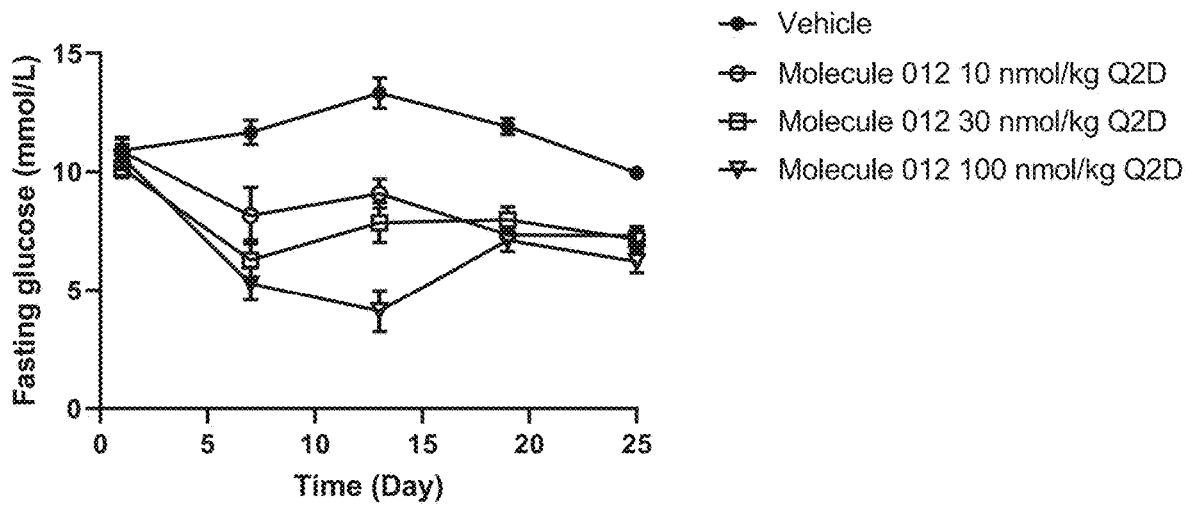

Conclusion: in DIO study, as shown in FIG. 3A, 3B and Table 8, Molecule 012 showed dose dependent efficacy on body weight reduction, food intake reduction and blood glucose control.

TABLE 8

Food intake and body weight reduction in DIO mice at Day 25

| Group | Cumulative food intake reduction (% reduction compared to vehicle) (Day25) | Body weight reduction (% reduction compared to vehicle) (Day25) |
| --- | --- | --- |
| Molecule 012 10 nmol/kg, Q2D | 35 | 18.42 |
| Molecule 012 30 nmol/kg, Q2D | 37 | 23.0 |
| Molecule 012 100 nmol/kg, Q2D | 51 | 37.6 |

Example 9a: PK Study in Non-Human Primates

Pharmacokinetics of selected molecules are assessed in monkeys. Both subcutaneous and intravenous injections are performed.

Method: 3-5 years old male cynomolgus monkeys were administrated in a single subcutaneous dose of 5 nmol/kg protein (n=2/group). Plasma samples for semaglutide group were collected pre-dose (−5 min), 2 hr, 4 hr, 6 hr, 8 hr, 24 hr, 48 hr, 72 hr, 96 hr, 120 hr, 144 hr, 216 hr, 288 hr, 360 hr, 432 hr and 504 hr after the injection. Plasma samples for 012 group were collected pre-dose (−5 min), 0.5 hr, 1 hr, 2 hr, 4 hr, 6 hr, 8 hr, 24 hr, 48 hr, 96 hr, 120 hr, 144 hr, 168 hr, 192 hr, 216 hr, 288 hr, 432 hr and 504 hr after the injection. For semaglutide group, the concentrations of proteins in the plasma were measured by ELISA assay. For 012 group, the concentrations of proteins in the plasma were measured by LC-MS/MS method. Based on the graph showing plasma concentration of each protein versus time after subcutaneous injection, the pharmacokinetic parameters were calculated by WinNonlin.

Conclusion: Molecule 012 showed longer half-life than semaglutide and Molecule 002 in monkey (Table 9a)

TABLE 9a

Pharmacokinetic parameters of GLP-1 polypeptide conjugates in cynomolgus monkeys. Pharmacokinetic data were analyzed by WinNonlin software. Tmax, Cmax, $T_{1/2}$; AUG were calculated for each molecule.

| PK parameters | Unit | Semaglutide | Molecule 012 |
| --- | --- | --- | --- |
| $T_{max}$ | hr | 7 | 24 |
| $C_{max}$ | nmol/L | 48.1 | 58.0 |
| Terminal $t_{1/2}$ | hr | 65 | 122 |
| $AUC_{tau}$ | hr*nmol/L | 2876 | 10989 |
| | | (Tau = 96 h) | (Tau = 504 h) |

Example 9b: PK Study in Non-Human Primates

Method: 3-5 years old male cynomolgus monkeys were administrated in a single intravenous dose of 4 nmol/kg and 5 nmol/kg for semaglutide and Molecule 019 (n=2/group), respectively, Plasma samples for semaglutide group were collected pre-dose (−5 min), 0.083 hr, 1 hr, 2 hr, 4 hr, 8 hr, 24 hr, 36 hr, 48 hr, 72 hr, 96 hr, 120 hr, 144 hr, and 168 hr after the injection. Plasma samples for 012 group were collected pre-dose (−5 min), 0.083 hr, 0.25 hr, 0.5 hr, 1 hr, 2 hr, 4 hr, 8 hr, 12 hr, 24 hr, 36 hr, 48 hr, 72 hr, 96 hr, 120 hr, 144 hr, and 168 hr after the injection. The concentrations of proteins in the plasma were measured by LC-MS/MS method. Based on the graph showing plasma concentration of each protein versus time after intravenous administration, the pharmacokinetic parameters were calculated by Win-Nonlin.

Conclusion: Molecule 019 showed similar half-life with semaglutide in monkeys (Table 9b).

TABLE 9b

Pharmacokinetic parameters of GLP-1 polypeptide conjugates in cynomolgus monkeys. Pharmacokinetic data were analyzed by WinNonlin software. $C_0$, $T_{1/2}$ and AUC were calculated for each molecule.

| PK parameters | Unit | Semaglutide | Molecule 019 |
| --- | --- | --- | --- |
| $C_0$ | nmol/L | 85.1 | 176.5 |
| Terminal $t_{1/2}$ | hr | 42.8 | 49.0 |
| $AUC_{tau}$ | hr*nmol/L | 2402 (t = 168 hr) | 5302 (t = 168 hr) |

Example 10: Immunogenicity Assessment

Selected GLP-1 polypeptide conjugates are also assessed for immunogenicity by in silica (iTope and TCED methods) and ex vivo (EpiScreen) methods.

Example 11: Human Serum Albumin Binding

Method: Binding of molecules to serum albumin was characterized by surface plastron resonance in a Biacore 8K instrument, Serum albumin from different species was covalently bound to CM5 sensor chips surface until 4000 RU was reached. The chip was blocked by 1M ethanolamine with flowrate of 10 μL/min for 420 s, Each molecule sample was diluted and injected at a flow rate of 30 μL/min to allow for binding to chip-bound albumin for 120 s and for dissociation for 300 s. Binding buffer without molecule was sent over the chip at the flow rate of 20 seconds to allow spontaneous dissociation of bound molecule for 30 seconds.

Conclusion: Molecule 004, 001, 006 and 012 showed higher binding affinity of human serum albumin (see Table 10) than semaglutide and molecule 002 which is consistent with the PK data,

TABLE 10

Human serum albumin binding affinity

| | KD (μM) | Rmax (RU) |
| --- | --- | --- |
| Semaglutide | 2.82 | 55.2 |
| Molecule 004 | 0.716 | 546.0 |
| Molecule 001 | 0.697 | 498.3 |
| Molecule 006 | 0.746 | 398.6 |
| Molecule 012 | 0.376 | 207.3 |
| Molecule 002 | 9.11 | 307.8 |

The invention claimed is:

1. A polypeptide conjugate comprising a structure shown below, where the amino acid residues are represented as one letter abbreviations in circles:

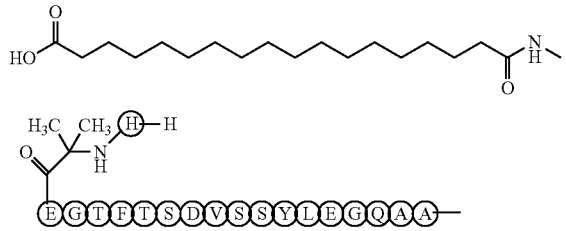

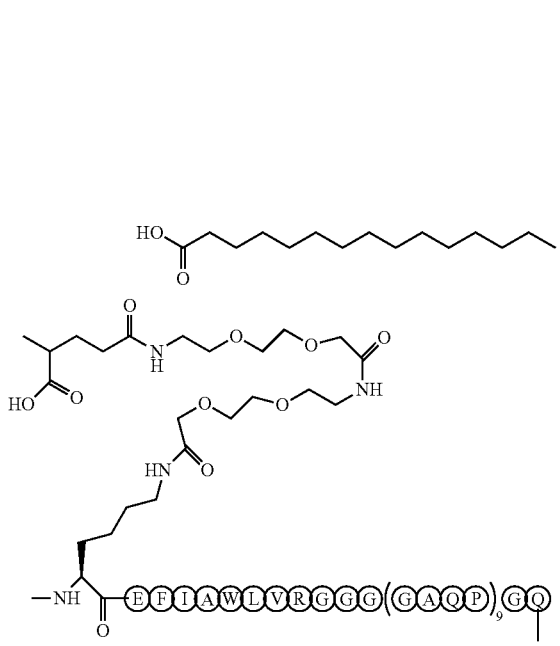

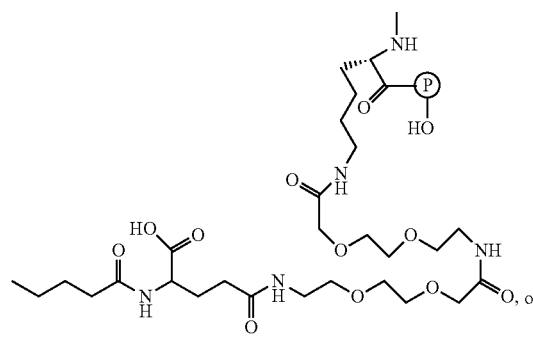

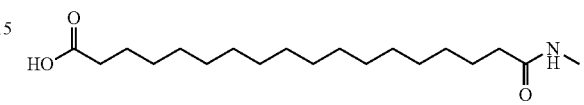

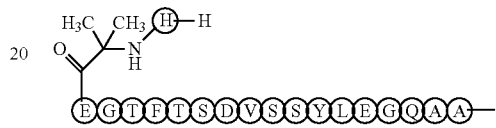

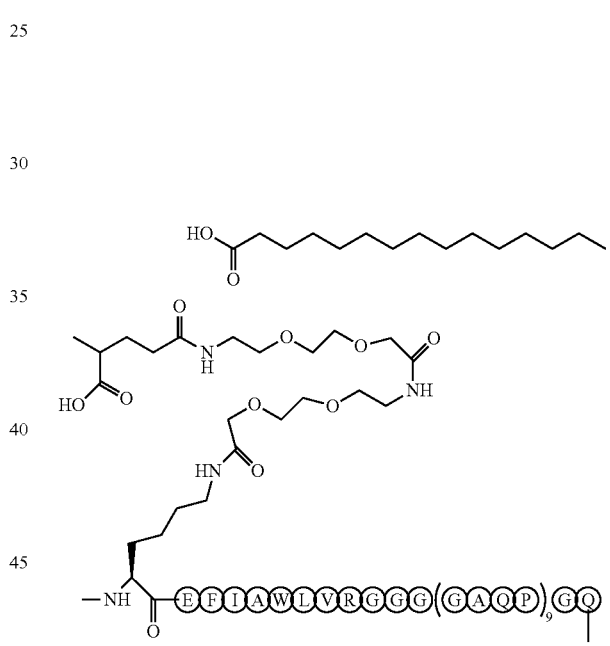

2. A polynucleotide encoding the polypeptide portion of the polypeptide conjugate of claim 1.

3. A vector comprising the polynucleotide of claim 2.

4. A host cell comprising the vector of claim 3.

5. A pharmaceutical composition comprising the polypeptide conjugate of claim 1, and a pharmaceutically acceptable carrier.

6. A method of treating a metabolic disorder in a subject in need thereof, comprising administering a therapeutically effective amount of the polypeptide conjugate of claim 1.

7. The method of claim 6, wherein the metabolic disorder is diabetes, obesity, overweight, non-alcoholic steatohepatitis (NASH), dyslipidemia, artherosclerosis, alcoholic steatohepatitis (ASH), diabeticnephropathy, gestational diabetes, metabolic syndrome X, nonalcoholic fatty liver disease (NAFLD), end-stage liver disease, hepatic steatosis (fatty liver), liver cirrhosis, or primary biliary cirrhosis (PBC).

8. A method of reducing food intake in a subject in need thereof, comprising administering a therapeutically effective amount of the polypeptide conjugate of claim 1.

9. A method of reducing body weight in a subject in need thereof, comprising administering a therapeutically effective amount of the polypeptide conjugate of claim 1.

10. The method of claim 6, wherein the polypeptide conjugate is administered at a dosing regimen that is no more frequent than once daily.

\* \* \* \* \*

SEQUENCE LISTING

```
<160> NUMBER OF SEQ ID NOS: 190

<210> SEQ ID NO 1
<211> LENGTH: 31
<212> TYPE: PRT
<213> ORGANISM: Artificial Sequence
<220> FEATURE:
<223> OTHER INFORMATION: Synthetic

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is H, imidazole-4-acetate (IA), or
      imidazolepropionic acid (IPA)
<220> FEATURE:
<221> NAME/KEY: MISC_FEATURE
<222> LOCATION: (2)..(2)
<223> OTHER INFORMATION: X is A, G, S, V, Aib, T, I, or L
```

```
<220> FEATURE:
<221> NAME/KEY: MISC_FEATURE
<222> LOCATION: (16)..(16)
<223> OTHER INFORMATION: X is G, or E
<220> FEATURE:
<221> NAME/KEY: MISC_FEATURE
<222> LOCATION: (17)..(17)
<223> OTHER INFORMATION: X is Q, C or K
<220> FEATURE:
<221> NAME/KEY: MISC_FEATURE
<222> LOCATION: (20)..(20)
<223> OTHER INFORMATION: X is K, R, or C
<220> FEATURE:
<221> NAME/KEY: MISC_FEATURE
<222> LOCATION: (21)..(21)
<223> OTHER INFORMATION: X is E, K, or C
<220> FEATURE:
<221> NAME/KEY: MISC_FEATURE
<222> LOCATION: (24)..(24)
<223> OTHER INFORMATION: X is A, C or K
<220> FEATURE:
<221> NAME/KEY: MISC_FEATURE
<222> LOCATION: (28)..(28)
<223> OTHER INFORMATION: X is R, K, or C
<220> FEATURE:
<221> NAME/KEY: MISC_FEATURE
<222> LOCATION: (30)..(30)
<223> OTHER INFORMATION: X is R or G

<400> SEQUENCE: 2

Xaa Xaa Glu Gly Thr Phe Thr Ser Asp Val Ser Ser Tyr Leu Glu Xaa
1               5                   10                  15

Xaa Ala Ala Xaa Xaa Phe Ile Xaa Trp Leu Val Xaa Gly Xaa Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 3

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 4

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly
            20                  25                  30

<210> SEQ ID NO 5
```

```
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 5

His Xaa Glu Gly Thr Phe Thr Ser Asp Val Ser Ser Tyr Leu Glu Gly
1               5                   10                  15

Gln Ala Ala Arg Lys Phe Ile Ala Trp Leu Val Arg Gly Gly Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 6

His Xaa Glu Gly Thr Phe Thr Ser Asp Val Ser Ser Tyr Leu Glu Gly
1               5                   10                  15

Gln Ala Ala Lys Cys Phe Ile Ala Trp Leu Val Arg Gly Gly Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 7

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 8

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly
            20                  25                  30
```

```
<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 9

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 10

His Xaa Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Gly Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 11

His Xaa Glu Gly Thr Phe Thr Ser Asp Val Ser Ser Tyr Leu Glu Glu
1               5                   10                  15

Gln Ala Ala Lys Cys Phe Ile Ala Trp Leu Val Arg Gly Gly Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 12

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30
```

<210> SEQ ID NO 13
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 13

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 14

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Arg Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 15

His Xaa Glu Gly Thr Phe Thr Ser Asp Val Ser Ser Tyr Leu Glu Gly
1               5                   10                  15

Gln Ala Ala Arg Lys Phe Ile Ala Trp Leu Val Arg Gly Arg Gly
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 16

His Xaa Glu Gly Thr Phe Thr Ser Asp Val Ser Ser Tyr Leu Glu Gly
1               5                   10                  15

Gln Ala Ala Lys Cys Phe Ile Ala Trp Leu Val Arg Gly Arg Gly
            20                  25                  30

```
<210> SEQ ID NO 17
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 17

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 18

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Arg Gly
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 19

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Arg Gly
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 20

His Xaa Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Arg Gly
```

<210> SEQ ID NO 21
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 21

His Xaa Glu Gly Thr Phe Thr Ser Asp Val Ser Ser Tyr Leu Glu Glu
1               5                   10                  15

Gln Ala Ala Lys Cys Phe Ile Ala Trp Leu Val Arg Gly Arg Gly
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 22

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic

<400> SEQUENCE: 23

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic

<400> SEQUENCE: 24

His Gly Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Synthetic

<400> SEQUENCE: 25

His Gly Glu Gly Thr Phe Thr Ser Asp Val Ser Ser Tyr Leu Glu Gly
1               5                   10                  15
Gln Ala Ala Arg Lys Phe Ile Ala Trp Leu Val Arg Gly Gly Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic

<400> SEQUENCE: 26

His Gly Glu Gly Thr Phe Thr Ser Asp Val Ser Ser Tyr Leu Glu Gly
1               5                   10                  15
Gln Ala Ala Lys Cys Phe Ile Ala Trp Leu Val Arg Gly Gly Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic

<400> SEQUENCE: 27

His Gly Glu Gly Thr Phe Thr Ser Asp Val Ser Ser Tyr Leu Glu Gly
1               5                   10                  15
Gln Ala Ala Arg Glu Phe Ile Ala Trp Leu Val Arg Gly Gly Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic

<400> SEQUENCE: 28

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Arg Gly Gly Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic

<400> SEQUENCE: 29

His Gly Glu Gly Thr Phe Thr Ser Asp Val Ser Ser Tyr Leu Glu Glu
1               5                   10                  15
Gln Ala Ala Cys Glu Phe Ile Ala Trp Leu Val Arg Gly Gly Gly
            20                  25                  30

<210> SEQ ID NO 30
<211> LENGTH: 31
<212> TYPE: PRT

<213> ORGANISM: Artificial Sequence
<220> FEATURE:
<223> OTHER INFORMATION: Synthetic

<400> SEQUENCE: 30

His Gly Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Gly Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Synthetic

<400> SEQUENCE: 31

His Gly Glu Gly Thr Phe Thr Ser Asp Val Ser Ser Tyr Leu Glu Glu
1               5                   10                  15

Gln Ala Ala Lys Cys Phe Ile Ala Trp Leu Val Arg Gly Gly Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic

<400> SEQUENCE: 32

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Synthetic

<400> SEQUENCE: 33

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Synthetic

<400> SEQUENCE: 34

His Gly Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Arg Gly
            20                  25                  30

<210> SEQ ID NO 35
<211> LENGTH: 31

```
<212> TYPE: PRT
<213> ORGANISM: Artificial Sequence
<220> FEATURE:
<223> OTHER INFORMATION: Synthetic

<400> SEQUENCE: 35

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Synthetic

<400> SEQUENCE: 36

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Arg Gly
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Synthetic

<400> SEQUENCE: 37

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Arg Gly
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Synthetic

<400> SEQUENCE: 38

His Gly Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Arg Gly
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic

<400> SEQUENCE: 39

His Gly Glu Gly Thr Phe Thr Ser Asp Val Ser Ser Tyr Leu Glu Glu
1               5                   10                  15

Gln Ala Ala Lys Cys Phe Ile Ala Trp Leu Val Arg Gly Arg Gly
            20                  25                  30

<210> SEQ ID NO 40
```

```
<211> LENGTH: 31
<212> TYPE: PRT
<213> ORGANISM: Artificial Sequence
<220> FEATURE:
<223> OTHER INFORMATION: Synthetic

<400> SEQUENCE: 40

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Synthetic

<400> SEQUENCE: 41

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Synthetic

<400> SEQUENCE: 42

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Synthetic

<400> SEQUENCE: 43

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Synthetic

<400> SEQUENCE: 44

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

```
<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Gly Gln Glu Pro Gly Ala Gln Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gly Ala Gln Pro Gly Ala Gln Pro
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Gly Gln Glu Pro
1

<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Gly Ala Gln Pro
1

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Gly Ala Gln Pro Gly Gln Glu Pro Gly Ala Gln Pro
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

Gly Ala Gln Pro Gly Gln Glu Pro
1               5

<210> SEQ ID NO 51
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 51

Gly Glu Gln Pro
1

<210> SEQ ID NO 52
<211> LENGTH: 4
<212> TYPE: PRT
<213> ORGANISM: Artificial Sequence
<220> FEATURE:
<223> OTHER INFORMATION: Synthetic

<400> SEQUENCE: 52

Gly Pro Gln Glu
1

<210> SEQ ID NO 53
<211> LENGTH: 4
<212> TYPE: PRT
<213> ORGANISM: Artificial Sequence
<220> FEATURE:
<223> OTHER INFORMATION: Synthetic

<400> SEQUENCE: 53

Gly Pro Glu Gln
1

<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Gly Ser Glu Pro
1

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Gly Glu Ser Pro
1

<210> SEQ ID NO 56
<211> LENGTH: 4
<212> TYPE: PRT
<213> ORGANISM: Artificial Sequence
<220> FEATURE:
<223> OTHER INFORMATION: Synthetic

<400> SEQUENCE: 56

Gly Pro Ser Glu
1

<210> SEQ ID NO 57
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 57

Gly Pro Glu Ser
1

<210> SEQ ID NO 58
<211> LENGTH: 4
<212> TYPE: PRT
<213> ORGANISM: Artificial Sequence
<220> FEATURE:
<223> OTHER INFORMATION: Synthetic

<400> SEQUENCE: 58

Gly Gln Ala Pro
1

<210> SEQ ID NO 59
<211> LENGTH: 4
<212> TYPE: PRT
<213> ORGANISM: Artificial Sequence
<220> FEATURE:
<223> OTHER INFORMATION: Synthetic

<400> SEQUENCE: 59

Gly Pro Ala Gln
1

<210> SEQ ID NO 60
<211> LENGTH: 4
<212> TYPE: PRT
<213> ORGANISM: Artificial Sequence
<220> FEATURE:
<223> OTHER INFORMATION: Synthetic

<400> SEQUENCE: 60

Gly Pro Gln Ala
1

<210> SEQ ID NO 61
<211> LENGTH: 4
<212> TYPE: PRT
<213> ORGANISM: Artificial Sequence
<220> FEATURE:
<223> OTHER INFORMATION: Synthetic

<400> SEQUENCE: 61

Gly Ser Gln Pro
1

<210> SEQ ID NO 62
<211> LENGTH: 4
<212> TYPE: PRT
<213> ORGANISM: Artificial Sequence
<220> FEATURE:
<223> OTHER INFORMATION: Synthetic

<400> SEQUENCE: 62

Gly Ala Ser Pro
1

<210> SEQ ID NO 63
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 63

Gly Pro Ala Ser
1

<210> SEQ ID NO 64
<211> LENGTH: 4
<212> TYPE: PRT
<213> ORGANISM: Artificial Sequence
<220> FEATURE:
<223> OTHER INFORMATION: Synthetic

<400> SEQUENCE: 64

Gly Pro Ser Ala
1

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Gly Gly Gly Ser
1

<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

Gly Ser Gly Ser
1

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

Gly Gly Gly Gly Ser
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Gln Glu Pro Gly Gln Ala Pro
1               5

<210> SEQ ID NO 69
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 69

Gly Gln Ala Pro Gly Gln Glu Pro
1               5

<210> SEQ ID NO 70
<211> LENGTH: 32
<212> TYPE: PRT
<213> ORGANISM: Artificial Sequence
<220> FEATURE:
<223> OTHER INFORMATION: Synthetic

<400> SEQUENCE: 70

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

<210> SEQ ID NO 71
<211> LENGTH: 6
<212> TYPE: PRT
<213> ORGANISM: Artificial Sequence
<220> FEATURE:
<223> OTHER INFORMATION: Synthetic

<400> SEQUENCE: 71

Ser Glu Pro Ala Thr Ser
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic

<400> SEQUENCE: 72

Gly Ser Glu Thr Pro Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic

<400> SEQUENCE: 73

Thr Ser Glu Ser Ala Thr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic

<400> SEQUENCE: 74

Pro Glu Ser Gly Pro Gly
1               5

<210> SEQ ID NO 75
<211> LENGTH: 6
```

<212> TYPE: PRT
<213> ORGANISM: Artificial Sequence
<220> FEATURE:
<223> OTHER INFORMATION: Synthetic

<400> SEQUENCE: 75

Thr Ser Thr Glu Pro Ser
1               5

<210> SEQ ID NO 76
<211> LENGTH: 40
<212> TYPE: PRT
<213> ORGANISM: Artificial Sequence
<220> FEATURE:
<223> OTHER INFORMATION: Synthetic

<400> SEQUENCE: 76

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Gln Ala Pro
        35                  40

<210> SEQ ID NO 77
<211> LENGTH: 80
<212> TYPE: PRT
<213> ORGANISM: Artificial Sequence
<220> FEATURE:
<223> OTHER INFORMATION: Synthetic

<400> SEQUENCE: 77

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Gln Ala Pro
65                  70                  75                  80

<210> SEQ ID NO 78
<211> LENGTH: 60
<212> TYPE: PRT
<213> ORGANISM: Artificial Sequence
<220> FEATURE:
<223> OTHER INFORMATION: Synthetic

<400> SEQUENCE: 78

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Gln Ala Pro
    50                  55                  60

<210> SEQ ID NO 79
<211> LENGTH: 48

```
<212> TYPE: PRT
<213> ORGANISM: Artificial Sequence
<220> FEATURE:
<223> OTHER INFORMATION: Synthetic

<400> SEQUENCE: 79

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Gln Ala Pro
        35                  40                  45

<210> SEQ ID NO 80
<211> LENGTH: 32
<212> TYPE: PRT
<213> ORGANISM: Artificial Sequence
<220> FEATURE:
<223> OTHER INFORMATION: Synthetic

<400> SEQUENCE: 80

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Ala Pro
            20                  25                  30

<210> SEQ ID NO 81
<211> LENGTH: 24
<212> TYPE: PRT
<213> ORGANISM: Artificial Sequence
<220> FEATURE:
<223> OTHER INFORMATION: Synthetic

<400> SEQUENCE: 81

Gly Ala Gln Pro Gly Ala Gln Pro Gly Ala Gln Pro Gly Ala Gln Pro
1               5                   10                  15

Gly Ala Gln Pro Gly Gln Ala Pro
            20

<210> SEQ ID NO 82
<211> LENGTH: 12
<212> TYPE: PRT
<213> ORGANISM: Artificial Sequence
<220> FEATURE:
<223> OTHER INFORMATION: Synthetic

<400> SEQUENCE: 82

Gly Ala Gln Pro Gly Ala Gln Pro Gly Gln Ala Pro
1               5                   10

<210> SEQ ID NO 83
<211> LENGTH: 40
<212> TYPE: PRT
<213> ORGANISM: Artificial Sequence
<220> FEATURE:
<223> OTHER INFORMATION: Synthetic

<400> SEQUENCE: 83

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro
        35                  40
```

<210> SEQ ID NO 84
<211> LENGTH: 80
<212> TYPE: PRT
<213> ORGANISM: Artificial Sequence
<220> FEATURE:
<223> OTHER INFORMATION: Synthetic

<400> SEQUENCE: 84

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 85
<211> LENGTH: 60
<212> TYPE: PRT
<213> ORGANISM: Artificial Sequence
<220> FEATURE:
<223> OTHER INFORMATION: Synthetic

<400> SEQUENCE: 85

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 86
<211> LENGTH: 48
<212> TYPE: PRT
<213> ORGANISM: Artificial Sequence
<220> FEATURE:
<223> OTHER INFORMATION: Synthetic

<400> SEQUENCE: 86

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

<210> SEQ ID NO 87
<211> LENGTH: 32
<212> TYPE: PRT
<213> ORGANISM: Artificial Sequence
<220> FEATURE:
<223> OTHER INFORMATION: Synthetic

<400> SEQUENCE: 87

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

<210> SEQ ID NO 88
<211> LENGTH: 24
<212> TYPE: PRT
<213> ORGANISM: Artificial Sequence
<220> FEATURE:
<223> OTHER INFORMATION: Synthetic

<400> SEQUENCE: 88

Gly Ala Gln Pro Gly Ala Gln Pro Gly Ala Gln Pro Gly Ala Gln Pro
1               5                   10                  15

Gly Ala Gln Pro Gly Ala Gln Pro
            20

<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Gly Ala Gln Pro Gly Ala Gln Pro Gly Ala Gln Pro
1               5                   10

<210> SEQ ID NO 90
<211> LENGTH: 40
<212> TYPE: PRT
<213> ORGANISM: Artificial Sequence
<220> FEATURE:
<223> OTHER INFORMATION: Synthetic

<400> SEQUENCE: 90

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Gln Lys Pro
        35                  40

<210> SEQ ID NO 91
<211> LENGTH: 80
<212> TYPE: PRT
<213> ORGANISM: Artificial Sequence
<220> FEATURE:
<223> OTHER INFORMATION: Synthetic

<400> SEQUENCE: 91

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Gln Lys Pro
65                  70                  75                  80

<210> SEQ ID NO 92

<211> LENGTH: 60
<212> TYPE: PRT
<213> ORGANISM: Artificial Sequence
<220> FEATURE:
<223> OTHER INFORMATION: Synthetic

<400> SEQUENCE: 92

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Gln Lys Pro
    50                  55                  60

<210> SEQ ID NO 93
<211> LENGTH: 48
<212> TYPE: PRT
<213> ORGANISM: Artificial Sequence
<220> FEATURE:
<223> OTHER INFORMATION: Synthetic

<400> SEQUENCE: 93

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Gln Lys Pro
        35                  40                  45

<210> SEQ ID NO 94
<211> LENGTH: 32
<212> TYPE: PRT
<213> ORGANISM: Artificial Sequence
<220> FEATURE:
<223> OTHER INFORMATION: Synthetic

<400> SEQUENCE: 94

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Lys Pro
            20                  25                  30

<210> SEQ ID NO 95
<211> LENGTH: 24
<212> TYPE: PRT
<213> ORGANISM: Artificial Sequence
<220> FEATURE:
<223> OTHER INFORMATION: Synthetic

<400> SEQUENCE: 95

Gly Ala Gln Pro Gly Ala Gln Pro Gly Ala Gln Pro Gly Ala Gln Pro
1               5                   10                  15

Gly Ala Gln Pro Gly Gln Lys Pro
            20

<210> SEQ ID NO 96
<211> LENGTH: 12
<212> TYPE: PRT
<213> ORGANISM: Artificial Sequence
<220> FEATURE:
<223> OTHER INFORMATION: Synthetic

<400> SEQUENCE: 96

Gly Ala Gln Pro Gly Ala Gln Pro Gly Gln Lys Pro
1               5                   10

<210> SEQ ID NO 97
<211> LENGTH: 40
<212> TYPE: PRT
<213> ORGANISM: Artificial Sequence
<220> FEATURE:
<223> OTHER INFORMATION: Synthetic

<400> SEQUENCE: 97

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Lys Pro
            35                  40

<210> SEQ ID NO 98
<211> LENGTH: 80
<212> TYPE: PRT
<213> ORGANISM: Artificial Sequence
<220> FEATURE:
<223> OTHER INFORMATION: Synthetic

<400> SEQUENCE: 98

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Lys Pro
65                  70                  75                  80

<210> SEQ ID NO 99
<211> LENGTH: 60
<212> TYPE: PRT
<213> ORGANISM: Artificial Sequence
<220> FEATURE:
<223> OTHER INFORMATION: Synthetic

<400> SEQUENCE: 99

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Lys Pro
        50                  55                  60

<210> SEQ ID NO 100
<211> LENGTH: 48
<212> TYPE: PRT
<213> ORGANISM: Artificial Sequence
<220> FEATURE:
<223> OTHER INFORMATION: Synthetic

```
<400> SEQUENCE: 100

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Lys Pro
        35                  40                  45

<210> SEQ ID NO 101
<211> LENGTH: 32
<212> TYPE: PRT
<213> ORGANISM: Artificial Sequence
<220> FEATURE:
<223> OTHER INFORMATION: Synthetic

<400> SEQUENCE: 101

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Lys Pro
            20                  25                  30

<210> SEQ ID NO 102
<211> LENGTH: 24
<212> TYPE: PRT
<213> ORGANISM: Artificial Sequence
<220> FEATURE:
<223> OTHER INFORMATION: Synthetic

<400> SEQUENCE: 102

Gly Ala Gln Pro Gly Ala Gln Pro Gly Ala Gln Pro Gly Ala Gln Pro
1               5                   10                  15

Gly Ala Gln Pro Gly Ala Lys Pro
            20

<210> SEQ ID NO 103
<211> LENGTH: 12
<212> TYPE: PRT
<213> ORGANISM: Artificial Sequence
<220> FEATURE:
<223> OTHER INFORMATION: Synthetic

<400> SEQUENCE: 103

Gly Ala Gln Pro Gly Ala Gln Pro Gly Ala Lys Pro
1               5                   10

<210> SEQ ID NO 104
<211> LENGTH: 40
<212> TYPE: PRT
<213> ORGANISM: Artificial Sequence
<220> FEATURE:
<223> OTHER INFORMATION: Synthetic

<400> SEQUENCE: 104

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Gln Cys Pro
        35                  40

<210> SEQ ID NO 105
<211> LENGTH: 80
<212> TYPE: PRT
```

<213> ORGANISM: Artificial Sequence
<220> FEATURE:
<223> OTHER INFORMATION: Synthetic

<400> SEQUENCE: 105

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Gln Cys Pro
65                  70                  75                  80

<210> SEQ ID NO 106
<211> LENGTH: 60
<212> TYPE: PRT
<213> ORGANISM: Artificial Sequence
<220> FEATURE:
<223> OTHER INFORMATION: Synthetic

<400> SEQUENCE: 106

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Gln Cys Pro
        50                  55                  60

<210> SEQ ID NO 107
<211> LENGTH: 48
<212> TYPE: PRT
<213> ORGANISM: Artificial Sequence
<220> FEATURE:
<223> OTHER INFORMATION: Synthetic

<400> SEQUENCE: 107

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Gln Cys Pro
            35                  40                  45

<210> SEQ ID NO 108
<211> LENGTH: 32
<212> TYPE: PRT
<213> ORGANISM: Artificial Sequence
<220> FEATURE:
<223> OTHER INFORMATION: Synthetic

<400> SEQUENCE: 108

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Cys Pro
                20                  25                  30

-continued

```
<210> SEQ ID NO 109
<211> LENGTH: 24
<212> TYPE: PRT
<213> ORGANISM: Artificial Sequence
<220> FEATURE:
<223> OTHER INFORMATION: Synthetic

<400> SEQUENCE: 109

Gly Ala Gln Pro Gly Ala Gln Pro Gly Ala Gln Pro Gly Ala Gln Pro
1               5                   10                  15

Gly Ala Gln Pro Gly Gln Cys Pro
            20

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

Gly Ala Gln Pro Gly Ala Gln Pro Gly Gln Cys Pro
1               5                   10

<210> SEQ ID NO 111
<211> LENGTH: 40
<212> TYPE: PRT
<213> ORGANISM: Artificial Sequence
<220> FEATURE:
<223> OTHER INFORMATION: Synthetic

<400> SEQUENCE: 111

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Cys Pro
        35                  40

<210> SEQ ID NO 112
<211> LENGTH: 80
<212> TYPE: PRT
<213> ORGANISM: Artificial Sequence
<220> FEATURE:
<223> OTHER INFORMATION: Synthetic

<400> SEQUENCE: 112

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Cys Pro
65                  70                  75                  80

<210> SEQ ID NO 113
<211> LENGTH: 60
<212> TYPE: PRT
<213> ORGANISM: Artificial Sequence
<220> FEATURE:
<223> OTHER INFORMATION: Synthetic
```

<400> SEQUENCE: 113

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Cys Pro
        50                  55              60

<210> SEQ ID NO 114
<211> LENGTH: 48
<212> TYPE: PRT
<213> ORGANISM: Artificial Sequence
<220> FEATURE:
<223> OTHER INFORMATION: Synthetic

<400> SEQUENCE: 114

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Cys Pro
            35                  40                  45

<210> SEQ ID NO 115
<211> LENGTH: 32
<212> TYPE: PRT
<213> ORGANISM: Artificial Sequence
<220> FEATURE:
<223> OTHER INFORMATION: Synthetic

<400> SEQUENCE: 115

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Cys Pro
                20                  25                  30

<210> SEQ ID NO 116
<211> LENGTH: 24
<212> TYPE: PRT
<213> ORGANISM: Artificial Sequence
<220> FEATURE:
<223> OTHER INFORMATION: Synthetic

<400> SEQUENCE: 116

Gly Ala Gln Pro Gly Ala Gln Pro Gly Ala Gln Pro Gly Ala Gln Pro
1               5                   10                  15

Gly Ala Gln Pro Gly Ala Cys Pro
            20

<210> SEQ ID NO 117
<211> LENGTH: 12
<212> TYPE: PRT
<213> ORGANISM: Artificial Sequence
<220> FEATURE:
<223> OTHER INFORMATION: Synthetic

<400> SEQUENCE: 117

Gly Ala Gln Pro Gly Ala Gln Pro Gly Ala Cys Pro
1               5                   10

<210> SEQ ID NO 118
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 118

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Lys Pro
65                  70

<210> SEQ ID NO 119
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 119

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Lys Pro
65                  70

<210> SEQ ID NO 120
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 120

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly

```
                35                  40                  45
Ala Gln Pro Gly Ala Gln Pro Gly Ala Gln Pro Gly Ala Gln Pro Gly
         50                  55                  60

Ala Gln Pro Gly Ala Gln Pro Gly Ala Gln Pro Gly Ala Gln Pro Gly
 65                  70                  75                  80

Ala Gln Pro Gly Ala Gln Pro Gly Ala Gln Pro Gly Ala Gln Pro Gly
                 85                  90                  95

Ala Gln Pro Gly Ala Gln Pro Gly Ala Gln Pro Gly Gln Lys Pro
            100                 105                 110

<210> SEQ ID NO 121
<211> LENGTH: 91
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 121

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
         50                  55                  60

Ala Gln Pro Gly Ala Gln Pro Gly Ala Gln Pro Gly Ala Gln Pro Gly
 65                  70                  75                  80

Ala Gln Pro Gly Ala Gln Pro Gly Gln Lys Pro
                 85                  90

<210> SEQ ID NO 122
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 122

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
         50                  55                  60

Ala Gln Pro Gly Ala Gln Pro Gly Ala Gln Pro Gly Gln Lys Pro
 65                  70                  75

<210> SEQ ID NO 123
<211> LENGTH: 63
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 123

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
    50                  55                  60

<210> SEQ ID NO 124
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 124

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Lys Pro
    50                  55

<210> SEQ ID NO 125
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 125

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Gln Lys Pro
        35                  40

<210> SEQ ID NO 126
<211> LENGTH: 63
<212> TYPE: PRT
<213> ORGANISM: Artificial Sequence
<220> FEATURE:
<223> OTHER INFORMATION: Synthetic
<220> FEATURE:
```

<221> NAME/KEY: MISC_FEATURE
<222> LOCATION: (2)..(2)
<223> OTHER INFORMATION: X is Aib

<400> SEQUENCE: 126

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
    50                  55                  60

<210> SEQ ID NO 127
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 127

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Lys Pro
    50                  55

<210> SEQ ID NO 128
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 128

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Gln Lys Pro
        35                  40

<210> SEQ ID NO 129
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib -continued

```
<400> SEQUENCE: 129

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Lys Pro
65                  70

<210> SEQ ID NO 130
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 130

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Gln Lys Pro
            100                 105                 110

<210> SEQ ID NO 131
<211> LENGTH: 91
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 131

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
```

```
                65                  70                  75                  80
Ala Gln Pro Gly Ala Gln Pro Gly Gln Lys Pro
                85                  90

<210> SEQ ID NO 132
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 132

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Gln Lys Pro
65                  70                  75

<210> SEQ ID NO 133
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 133

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
    50                  55                  60

<210> SEQ ID NO 134
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 134

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30
```

```
Ala Gln Pro Gly Ala Gln Pro Gly Ala Gln Pro Gly Ala Gln Pro Gly
        35                  40                  45

Ala Gln Pro Gly Gln Lys Pro
    50                  55
```

<210> SEQ ID NO 135
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 135

```
His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Gln Lys Pro
        35                  40
```

<210> SEQ ID NO 136
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 136

```
His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Lys Pro
65                  70
```

<210> SEQ ID NO 137
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 137

```
His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30
```

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
        50                  55                  60

<210> SEQ ID NO 138
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 138

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Lys Pro
        50              55

<210> SEQ ID NO 139
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 139

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Gln Lys Pro
        35                  40

<210> SEQ ID NO 140
<211> LENGTH: 71
<212> TYPE: PRT
<213> ORGANISM: Artificial Sequence
<220> FEATURE:
<223> OTHER INFORMATION: Synthetic

<400> SEQUENCE: 140

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
        50                  55                  60

Ala Gln Pro Gly Gln Lys Pro
65                  70

<210> SEQ ID NO 141
<211> LENGTH: 111
<212> TYPE: PRT
<213> ORGANISM: Artificial Sequence
<220> FEATURE:
<223> OTHER INFORMATION: Synthetic

<400> SEQUENCE: 141

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Gln Lys Pro
            100                 105                 110
```

<210> SEQ ID NO 142
<211> LENGTH: 91
<212> TYPE: PRT
<213> ORGANISM: Artificial Sequence
<220> FEATURE:
<223> OTHER INFORMATION: Synthetic

<400> SEQUENCE: 142

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Gln Lys Pro
                85                  90
```

<210> SEQ ID NO 143
<211> LENGTH: 79
<212> TYPE: PRT
<213> ORGANISM: Artificial Sequence
<220> FEATURE:
<223> OTHER INFORMATION: Synthetic

<400> SEQUENCE: 143

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45
```

-continued

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Gln Lys Pro
65                  70                  75

<210> SEQ ID NO 144
<211> LENGTH: 63
<212> TYPE: PRT
<213> ORGANISM: Artificial Sequence
<220> FEATURE:
<223> OTHER INFORMATION: Synthetic

<400> SEQUENCE: 144

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
    50                  55                  60

<210> SEQ ID NO 145
<211> LENGTH: 55
<212> TYPE: PRT
<213> ORGANISM: Artificial Sequence
<220> FEATURE:
<223> OTHER INFORMATION: Synthetic

<400> SEQUENCE: 145

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Lys Pro
    50                  55

<210> SEQ ID NO 146
<211> LENGTH: 43
<212> TYPE: PRT
<213> ORGANISM: Artificial Sequence
<220> FEATURE:
<223> OTHER INFORMATION: Synthetic

<400> SEQUENCE: 146

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Gln Lys Pro
        35                  40

<210> SEQ ID NO 147
<211> LENGTH: 71
<212> TYPE: PRT
<213> ORGANISM: Artificial Sequence
<220> FEATURE:
<223> OTHER INFORMATION: Synthetic

<400> SEQUENCE: 147

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Lys Pro
65                  70

<210> SEQ ID NO 148
<211> LENGTH: 63
<212> TYPE: PRT
<213> ORGANISM: Artificial Sequence
<220> FEATURE:
<223> OTHER INFORMATION: Synthetic

<400> SEQUENCE: 148

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Lys Pro
    50                  55                  60

<210> SEQ ID NO 149
<211> LENGTH: 55
<212> TYPE: PRT
<213> ORGANISM: Artificial Sequence
<220> FEATURE:
<223> OTHER INFORMATION: Synthetic

<400> SEQUENCE: 149

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Lys Pro
    50                  55

<210> SEQ ID NO 150
<211> LENGTH: 43
<212> TYPE: PRT
<213> ORGANISM: Artificial Sequence
<220> FEATURE:
<223> OTHER INFORMATION: Synthetic

<400> SEQUENCE: 150

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Gln Lys Pro
        35                  40

-continued

```
<210> SEQ ID NO 151
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 151

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Gln Cys Pro
            100                 105                 110

<210> SEQ ID NO 152
<211> LENGTH: 91
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 152

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Gln Cys Pro
                85                  90

<210> SEQ ID NO 153
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 153
```

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Gln Cys Pro
65                  70                  75

<210> SEQ ID NO 154
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 154

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 155
<211> LENGTH: 65
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 155

His Ala Ile Asx Glu Gly Thr Phe Thr Ser Asp Val Ser Ser Tyr Leu
1               5                   10                  15

Glu Gly Gln Ala Ala Cys Glu Phe Ile Ala Trp Leu Val Arg Gly Gly
            20                  25                  30

Gly Gly Ala Gln Pro Gly Ala Gln Pro Gly Ala Gln Pro Gly Ala Gln
        35                  40                  45

Pro Gly Ala Gln Pro Gly Ala Gln Pro Gly Ala Gln Pro Gly Gln Cys
    50                  55                  60

Pro
65

<210> SEQ ID NO 156
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 156

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Cys Pro
    50                  55

<210> SEQ ID NO 157
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 157

His Xaa Glu Gly Thr Phe Thr Ser Asp Val Ser Ser Tyr Leu Glu Gly
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Gln Cys Pro
        35                  40

<210> SEQ ID NO 158
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 158

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 159
<211> LENGTH: 63
<212> TYPE: PRT
<213> ORGANISM: Artificial Sequence
<220> FEATURE:

<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 159

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 160
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 160

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Cys Pro
    50                  55

<210> SEQ ID NO 161
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 161

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Gln Cys Pro
        35                  40

<210> SEQ ID NO 162
<211> LENGTH: 71
<212> TYPE: PRT
<213> ORGANISM: Artificial Sequence
<220> FEATURE:
<223> OTHER INFORMATION: Synthetic

<400> SEQUENCE: 162

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 163
<211> LENGTH: 111
<212> TYPE: PRT
<213> ORGANISM: Artificial Sequence
<220> FEATURE:
<223> OTHER INFORMATION: Synthetic

<400> SEQUENCE: 163

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Gln Cys Pro
            100                 105                 110

<210> SEQ ID NO 164
<211> LENGTH: 91
<212> TYPE: PRT
<213> ORGANISM: Artificial Sequence
<220> FEATURE:
<223> OTHER INFORMATION: Synthetic

<400> SEQUENCE: 164

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Gln Cys Pro
                85                  90

<210> SEQ ID NO 165
<211> LENGTH: 79
<212> TYPE: PRT
<213> ORGANISM: Artificial Sequence
<220> FEATURE:
<223> OTHER INFORMATION: Synthetic

<400> SEQUENCE: 165

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Gln Cys Pro
65                  70                  75

<210> SEQ ID NO 166
<211> LENGTH: 63
<212> TYPE: PRT
<213> ORGANISM: Artificial Sequence
<220> FEATURE:
<223> OTHER INFORMATION: Synthetic

<400> SEQUENCE: 166

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 167
<211> LENGTH: 54
<212> TYPE: PRT
<213> ORGANISM: Artificial Sequence
<220> FEATURE:
<223> OTHER INFORMATION: Synthetic

<400> SEQUENCE: 167

His Gly Glu Gly Thr Phe Thr Ser Asp Val Ser Ser Tyr Leu Glu Glu
1               5                   10                  15

Gln Ala Ala Cys Phe Ile Ala Trp Leu Val Arg Gly Gly Gly Gly Ala
            20                  25                  30

Gln Pro Gly Ala Gln Pro Gly Ala Gln Pro Gly Ala Gln Pro Gly Ala
        35                  40                  45

Gln Pro Gly Gln Cys Pro
    50

<210> SEQ ID NO 168
<211> LENGTH: 43
<212> TYPE: PRT
<213> ORGANISM: Artificial Sequence
<220> FEATURE:
<223> OTHER INFORMATION: Synthetic

<400> SEQUENCE: 168

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

```
Ala Gln Pro Gly Ala Gln Pro Gly Gln Cys Pro
        35                  40

<210> SEQ ID NO 169
<211> LENGTH: 71
<212> TYPE: PRT
<213> ORGANISM: Artificial Sequence
<220> FEATURE:
<223> OTHER INFORMATION: Synthetic

<400> SEQUENCE: 169

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 170
<211> LENGTH: 63
<212> TYPE: PRT
<213> ORGANISM: Artificial Sequence
<220> FEATURE:
<223> OTHER INFORMATION: Synthetic

<400> SEQUENCE: 170

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 171
<211> LENGTH: 55
<212> TYPE: PRT
<213> ORGANISM: Artificial Sequence
<220> FEATURE:
<223> OTHER INFORMATION: Synthetic

<400> SEQUENCE: 171

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Cys Pro
    50                  55

<210> SEQ ID NO 172
<211> LENGTH: 43
<212> TYPE: PRT
<213> ORGANISM: Artificial Sequence
<220> FEATURE:
```

<223> OTHER INFORMATION: Synthetic

<400> SEQUENCE: 172

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Gln Cys Pro
        35                  40

<210> SEQ ID NO 173
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 173

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Lys
65                  70

<210> SEQ ID NO 174
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 174

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Lys
    50                  55                  60

<210> SEQ ID NO 175
<211> LENGTH: 40
<212> TYPE: PRT
<213> ORGANISM: Artificial Sequence
<220> FEATURE:
<223> OTHER INFORMATION: Synthetic

<400> SEQUENCE: 175

Gly Ala Gln Pro Gly Ala Gln Pro Gly Ala Gln Pro Gly Ala Gln Pro

```
1               5                   10                  15
Gly Ala Gln Pro Gly Ala Gln Pro Gly Ala Gln Pro Gly Ala Gln Pro
                20                  25                  30

Gly Ala Gln Pro Gly Ala Gln Lys
        35                  40
```

<210> SEQ ID NO 176
<211> LENGTH: 32
<212> TYPE: PRT
<213> ORGANISM: Artificial Sequence
<220> FEATURE:
<223> OTHER INFORMATION: Synthetic

<400> SEQUENCE: 176

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Lys
                20                  25                  30
```

<210> SEQ ID NO 177
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 177

```
His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Gln Cys Pro
                100                 105                 110
```

<210> SEQ ID NO 178
<211> LENGTH: 91
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 178

```
His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
                20                  25                  30
```

Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Gln Cys Pro
            85                  90

<210> SEQ ID NO 179
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 179

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
50                  55                  60

Ala Gln Pro Gly Ala Gln Pro Gly Ala Gln Pro Gly Gln Cys Pro
65                  70                  75

<210> SEQ ID NO 180
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 180

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
50                  55                  60

Ala Gln Pro Gly Gln Cys Pro
65                  70

<210> SEQ ID NO 181
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 181

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 182
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 182

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Cys Pro
    50                  55

<210> SEQ ID NO 183
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 183

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly Gly
            20                  25                  30

Ala Gln Pro Gly Ala Gln Pro Gly Gln Cys Pro
        35                  40

<210> SEQ ID NO 184
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 184

His Xaa Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly
            20                  25                  30

<210> SEQ ID NO 185
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 185

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 186
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 186

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 187
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 187

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Gln Cys Pro
    50                  55

<210> SEQ ID NO 188
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 188

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Gln Cys Pro
65                  70

<210> SEQ ID NO 189
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 189

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Gln Cys Pro
    50                  55                  60

<210> SEQ ID NO 190
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 190

His Xaa Glu Gly Thr Phe Thr Ser Asp Val Ser Ser Tyr Leu Glu Glu

| 1 | | | | 5 | | | | | 10 | | | | | 15 | |
|---|---|---|---|---|---|---|---|---|---|---|---|---|---|---|---|
| Gln | Ala | Ala | Lys | Glu | Phe | Ile | Ala | Trp | Leu | Val | Arg | Gly | Gly | Gly | |
| | | | | 20 | | | | | 25 | | | | | 30 | |
| Ala | Gln | Pro | Gly | Ala | Gln | Pro | Gly | Ala | Gln | Pro | Gly | Ala | Gln | Pro | Gly |
| | | | | 35 | | | | | 40 | | | | | 45 | |
| Ala | Gln | Pro | Gly | Gln | Cys | Pro | | | | | | | | | |
| | | | | 50 | | | | | 55 | | | | | | |